(12) United States Patent
Muenzel et al.

(10) Patent No.: US 11,649,269 B2
(45) Date of Patent: May 16, 2023

(54) BIFUNCTIONAL COMPOUNDS COMPRISING INSULIN PEPTIDES AND EGF(A) PEPTIDES

(71) Applicant: Novo Nordisk A/S, Bagsvaerd (DK)

(72) Inventors: Martin Werner Borchsenius Muenzel, Broenshoej (DK); Susanne Hostrup, Vaerloese (DK); Gro Klitgaard Povlsen, Valby (DK); Mathias Norrman, Staffanstorp (SE); Thomas Boerglum Kjeldsen, Virum (DK); Claudia Ulrich Hjoerringgaard, Glostrup (DK); Peter Madsen, Pagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 16 days.

(21) Appl. No.: 17/281,813

(22) PCT Filed: Oct. 4, 2019

(86) PCT No.: PCT/EP2019/076889
§ 371 (c)(1),
(2) Date: Mar. 31, 2021

(87) PCT Pub. No.: WO2020/070276
PCT Pub. Date: Apr. 9, 2020

(65) Prior Publication Data
US 2022/0009989 A1 Jan. 13, 2022

(30) Foreign Application Priority Data
Oct. 5, 2018 (EP) .................................... 18198892

(51) Int. Cl.
*A61K 38/00* (2006.01)
*C07K 14/62* (2006.01)
*C07K 14/485* (2006.01)

(52) U.S. Cl.
CPC ............ *C07K 14/62* (2013.01); *C07K 14/485* (2013.01); *A61K 38/00* (2013.01)

(58) Field of Classification Search
CPC .... C07K 14/62; C07K 14/485; C07K 14/705; A61K 38/00; C12N 9/6454
See application file for complete search history.

(56) References Cited

U.S. PATENT DOCUMENTS

2011/0117011 A1 5/2011 Jackson et al.

FOREIGN PATENT DOCUMENTS

| CN | 104558199 A | 4/2015 |
| WO | 2009022006 A1 | 2/2009 |
| WO | 2011117401 A1 | 9/2011 |
| WO | 2012177741 A1 | 12/2012 |
| WO | 2015127273 A1 | 8/2015 |
| WO | 2016164762 A1 | 10/2016 |
| WO | 2017121850 A1 | 7/2017 |

OTHER PUBLICATIONS

Shan et al., "PCSK9 Binds to Multiple Receptors and Can Be Functionally Inhibited by an EGF-A Peptide," Biochemical and Biophysical Research Communications, 2008, vol. 375, No. 1, pp. 69-73.
Zhang et al., "Calcium-Independent Inhibition of PCSK9 by Affinity-Improved Variants of the LDL Receptor EGF(A) Domain," J. Mol. Biol., 2012, vol. 422, pp. 685-696.

*Primary Examiner* — Aradhana Sasan
*Assistant Examiner* — Mercy H Sabila
(74) *Attorney, Agent, or Firm* — Rosemarie R. Wilk-Orescan

(57) ABSTRACT

The present invention relates to novel covalently linked bi-functional fusion proteins comprising insulin and EGF (A) analogues or derivatives thereof, and their pharmaceutical use. Furthermore, the invention relates to pharmaceutical compositions comprising such bi-functional compounds, and to the use of such compounds for the treatment or prevention of medical conditions relating to diabetes and dyslipidaemia associated with diabetes.

14 Claims, 10 Drawing Sheets

Specification includes a Sequence Listing.

S.c. dosing of Insulin-EGF(A) fusion proteins to SD rats
(90 nmol/kg, mean ± SEM, n=4-5)

S.c. dosing of Insulin-EGF(A) fusion proteins to SD rats
(90 nmol/kg, mean ± SEM, n=4-5)

*4/5 rats dosed with the compound of Example 1 went into hypoglycemia and were euthanized

SEQUENCE LISTING

```
<160> NUMBER OF SEQ ID NOS: 34

<210> SEQ ID NO 1
<211> LENGTH: 40
<212> TYPE: PRT
<213> ORGANISM: ARTIFICIAL
<220> FEATURE:
<223> OTHER INFORMATION: Protein

<400> SEQUENCE: 1

Gly Thr Asn Glu Cys Leu Asp Asn Asn Gly Gly Cys Ser His Val Cys
1               5                   10                  15

Asn Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 2
<211> LENGTH: 21
<212> TYPE: PRT
<213> ORGANISM: ARTIFICIAL
<220> FEATURE:
<223> OTHER INFORMATION: Protein

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: ARTIFICIAL
<220> FEATURE:
<223> OTHER INFORMATION: Protein

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 8
<212> TYPE: PRT
<213> ORGANISM: ARTIFICIAL
<220> FEATURE:
<223> OTHER INFORMATION: Protein

<400> SEQUENCE: 4

Gly Gln Ala Pro Gly Gln Ala Pro
1               5
```

```
<210> SEQ ID NO 5
<211> LENGTH: 8
<212> TYPE: PRT
<213> ORGANISM: ARTIFICIAL
<220> FEATURE:
<223> OTHER INFORMATION: Protein

<400> SEQUENCE: 5

Gly Ala Gln Pro Gly Ala Gln Pro
1               5

<210> SEQ ID NO 6
<211> LENGTH: 12
<212> TYPE: PRT
<213> ORGANISM: ARTIFICIAL
<220> FEATURE:
<223> OTHER INFORMATION: Protein

<400> SEQUENCE: 6

Gly Ala Gln Pro Gly Ala Gln Pro Gly Ala Gln Pro
1               5                   10

<210> SEQ ID NO 7
<211> LENGTH: 16
<212> TYPE: PRT
<213> ORGANISM: ARTIFICIAL
<220> FEATURE:
<223> OTHER INFORMATION: Protein

<400> SEQUENCE: 7

Gly Ala Gln Pro Gly Ala Gln Pro Gly Ala Gln Pro Gly Ala Gln Pro
1               5                   10                  15

<210> SEQ ID NO 8
<211> LENGTH: 24
<212> TYPE: PRT
<213> ORGANISM: ARTIFICIAL
<220> FEATURE:
<223> OTHER INFORMATION: Protein

<400> SEQUENCE: 8

Gly Ala Gln Pro Gly Ala Gln Pro Gly Ala Gln Pro Gly Ala Gln Pro
1               5                   10                  15

Gly Ala Gln Pro Gly Ala Gln Pro
            20

<210> SEQ ID NO 9
<211> LENGTH: 32
<212> TYPE: PRT
<213> ORGANISM: ARTIFICIAL
<220> FEATURE:
<223> OTHER INFORMATION: Protein

<400> SEQUENCE: 9

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

<210> SEQ ID NO 10
<211> LENGTH: 40
<212> TYPE: PRT
<213> ORGANISM: ARTIFICIAL
<220> FEATURE:
<223> OTHER INFORMATION: Protein
```

```
<400> SEQUENCE: 10

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro
            35                  40

<210> SEQ ID NO 11
<211> LENGTH: 48
<212> TYPE: PRT
<213> ORGANISM: ARTIFICIAL
<220> FEATURE:
<223> OTHER INFORMATION: Protein

<400> SEQUENCE: 11

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

<210> SEQ ID NO 12
<211> LENGTH: 76
<212> TYPE: PRT
<213> ORGANISM: ARTIFICIAL
<220> FEATURE:
<223> OTHER INFORMATION: Protein

<400> SEQUENCE: 12

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro
65                  70                  75

<210> SEQ ID NO 13
<211> LENGTH: 8
<212> TYPE: PRT
<213> ORGANISM: ARTIFICIAL
<220> FEATURE:
<223> OTHER INFORMATION: Protein

<400> SEQUENCE: 13

Gly Gln Glu Pro Gly Gln Glu Pro
1               5

<210> SEQ ID NO 14
<211> LENGTH: 16
<212> TYPE: PRT
<213> ORGANISM: ARTIFICIAL
<220> FEATURE:
<223> OTHER INFORMATION: Protein

<400> SEQUENCE: 14

Gly Gln Glu Pro Gly Gln Glu Pro Gly Gln Glu Pro Gly Gln Glu Pro
```

-continued

<210> SEQ ID NO 15
<211> LENGTH: 24
<212> TYPE: PRT
<213> ORGANISM: ARTIFICIAL
<220> FEATURE:
<223> OTHER INFORMATION: Protein

<400> SEQUENCE: 15

Gly Gln Glu Pro Gly Gln Glu Pro Gly Gln Glu Pro Gly Gln Glu Pro
1               5                   10                  15

Gly Gln Glu Pro Gly Gln Glu Pro
            20

<210> SEQ ID NO 16
<211> LENGTH: 32
<212> TYPE: PRT
<213> ORGANISM: ARTIFICIAL
<220> FEATURE:
<223> OTHER INFORMATION: Protein

<400> SEQUENCE: 16

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

<210> SEQ ID NO 17
<211> LENGTH: 77
<212> TYPE: PRT
<213> ORGANISM: ARTIFICIAL
<220> FEATURE:
<223> OTHER INFORMATION: Protein

<400> SEQUENCE: 17

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
                20                  25                  30

Leu Val Ala Gln Arg Arg Cys Glu Gly Ala Gln Pro Gly Ala Gln Pro
            35                  40                  45

Phe Val Glu Gln His Leu Cys Gly Ser His Leu Val Glu Ala Leu Tyr
        50                  55                  60

Leu Val Cys Gly Glu Arg Gly Phe Phe Tyr Thr Pro Lys
65                  70                  75

<210> SEQ ID NO 18
<211> LENGTH: 109
<212> TYPE: PRT
<213> ORGANISM: ARTIFICIAL
<220> FEATURE:
<223> OTHER INFORMATION: Protein

<400> SEQUENCE: 18

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
                20                  25                  30

Leu Val Ala Gln Arg Arg Cys Glu Gly Ala Gln Pro Gly Ala Gln Pro
            35                  40                  45

Gly Ala Gln Pro Gly Ala Gln Pro Gly Ala Gln Pro Gly Ala Gln Pro

```
                50                  55                  60
Gly Ala Gln Pro Gly Ala Gln Pro Gly Ala Gln Pro Gly Ala Gln Pro
 65                  70                  75                  80

Phe Val Asn Gln His Leu Cys Gly Ser His Leu Val Glu Ala Leu Tyr
                 85                  90                  95

Leu Val Cys Gly Glu Arg Gly Phe Phe Tyr Thr Pro Lys
                100                 105
```

<210> SEQ ID NO 19
<211> LENGTH: 77
<212> TYPE: PRT
<213> ORGANISM: ARTIFICIAL
<220> FEATURE:
<223> OTHER INFORMATION: Protein

<400> SEQUENCE: 19

```
Gly Thr Asn Glu Cys Leu Asp Asn Leu Gly Gly Cys Ser His Val Cys
 1               5                  10                  15

Arg Asp Leu Glu Ile Gly Tyr Glu Cys Leu Cys Pro Glu Gly Phe Gln
                 20                  25                  30

Leu Val Ala Gln Arg Arg Cys Glu Gly Ala Gln Pro Gly Ala Gln Pro
             35                  40                  45

Phe Val Asn Gln His Leu Cys Gly Ser His Leu Val Glu Ala Leu Tyr
         50                  55                  60

Leu Val Cys Gly Glu Arg Gly Phe Phe Tyr Thr Pro Lys
 65                  70                  75
```

<210> SEQ ID NO 20
<211> LENGTH: 81
<212> TYPE: PRT
<213> ORGANISM: ARTIFICIAL
<220> FEATURE:
<223> OTHER INFORMATION: Protein

<400> SEQUENCE: 20

```
Gly Thr Asn Glu Cys Leu Asp Asn Leu Gly Gly Cys Ser His Val Cys
 1               5                  10                  15

Arg Asp Leu Glu Ile Gly Tyr Glu Cys Leu Cys Pro Glu Gly Phe Gln
                 20                  25                  30

Leu Val Ala Gln Arg Arg Cys Glu Gly Ala Gln Pro Gly Ala Gln Pro
             35                  40                  45

Gly Ala Gln Pro Phe Val Asn Gln His Leu Cys Gly Ser His Leu Val
         50                  55                  60

Glu Ala Leu Tyr Leu Val Cys Gly Glu Arg Gly Phe Phe Tyr Thr Pro
 65                  70                  75                  80

Lys
```

<210> SEQ ID NO 21
<211> LENGTH: 85
<212> TYPE: PRT
<213> ORGANISM: ARTIFICIAL
<220> FEATURE:
<223> OTHER INFORMATION: Protein

<400> SEQUENCE: 21

```
Gly Thr Asn Glu Cys Leu Asp Asn Leu Gly Gly Cys Ser His Val Cys
 1               5                  10                  15

Arg Asp Leu Glu Ile Gly Tyr Glu Cys Leu Cys Pro Glu Gly Phe Gln
                 20                  25                  30
```

-continued

Leu Val Ala Gln Arg Arg Cys Glu Gly Ala Gln Pro Ala Gln Pro
                35                  40                  45

Gly Ala Gln Pro Gly Ala Gln Pro Phe Val Asn Gln His Leu Cys Gly
    50                  55                  60

Ser His Leu Val Glu Ala Leu Tyr Leu Val Cys Gly Glu Arg Gly Phe
65                  70                  75                  80

Phe Tyr Thr Pro Lys
                85

<210> SEQ ID NO 22
<211> LENGTH: 93
<212> TYPE: PRT
<213> ORGANISM: ARTIFICIAL
<220> FEATURE:
<223> OTHER INFORMATION: Protein

<400> SEQUENCE: 22

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
                20                  25                  30

Leu Val Ala Gln Arg Arg Cys Glu Gly Ala Gln Pro Gly Ala Gln Pro
                35                  40                  45

Gly Ala Gln Pro Gly Ala Gln Pro Gly Ala Gln Pro Gly Ala Gln Pro
            50                  55                  60

Phe Val Asn Gln His Leu Cys Gly Ser His Leu Val Glu Ala Leu Tyr
65                  70                  75                  80

Leu Val Cys Gly Glu Arg Gly Phe Phe Tyr Thr Pro Lys
                85                  90

<210> SEQ ID NO 23
<211> LENGTH: 101
<212> TYPE: PRT
<213> ORGANISM: ARTIFICIAL
<220> FEATURE:
<223> OTHER INFORMATION: Protein

<400> SEQUENCE: 23

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
                20                  25                  30

Leu Val Ala Gln Arg Arg Cys Glu Gly Ala Gln Pro Gly Ala Gln Pro
                35                  40                  45

Gly Ala Gln Pro Gly Ala Gln Pro Gly Ala Gln Pro Gly Ala Gln Pro
            50                  55                  60

Gly Ala Gln Pro Gly Ala Gln Pro Phe Val Asn Gln His Leu Cys Gly
65                  70                  75                  80

Ser His Leu Val Glu Ala Leu Tyr Leu Val Cys Gly Glu Arg Gly Phe
                85                  90                  95

Phe Tyr Thr Pro Lys
                100

<210> SEQ ID NO 24
<211> LENGTH: 117
<212> TYPE: PRT
<213> ORGANISM: ARTIFICIAL
<220> FEATURE:
<223> OTHER INFORMATION: Protein

<400> SEQUENCE: 24

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Cys Glu Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

Gly Ala Gln Pro Gly Ala Gln Pro Phe Val Asn Gln His Leu Cys Gly
                85                  90                  95

Ser His Leu Val Glu Ala Leu Tyr Leu Val Cys Gly Glu Arg Gly Phe
                100                 105                 110

Phe Tyr Thr Pro Lys
            115

<210> SEQ ID NO 25
<211> LENGTH: 145
<212> TYPE: PRT
<213> ORGANISM: ARTIFICIAL
<220> FEATURE:
<223> OTHER INFORMATION: Protein

<400> SEQUENCE: 25

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Cys Glu Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

Gly Ala Gln Pro Gly Ala Gln Pro Gly Ala Gln Pro Gly Ala Gln Pro
                85                  90                  95

Gly Ala Gln Pro Gly Ala Gln Pro Gly Ala Gln Pro Gly Ala Gln Pro
                100                 105                 110

Gly Ala Gln Pro Phe Val Asn Gln His Leu Cys Gly Ser His Leu Val
            115                 120                 125

Glu Ala Leu Tyr Leu Val Cys Gly Glu Arg Gly Phe Phe Tyr Thr Pro
    130                 135                 140

Lys
145

<210> SEQ ID NO 26
<211> LENGTH: 145
<212> TYPE: PRT
<213> ORGANISM: ARTIFICIAL
<220> FEATURE:
<223> OTHER INFORMATION: Protein

<400> SEQUENCE: 26

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu Gly Ala Gln Pro Gly Ala Gln Pro
        35                  40                  45

Gly Ala Gln Pro Gly Ala Gln Pro Gly Ala Gln Pro Gly Ala Gln Pro
50                  55                  60

Gly Ala Gln Pro Gly Ala Gln Pro Gly Ala Gln Pro Gly Ala Gln Pro
65                  70                  75                  80

Gly Ala Gln Pro Gly Ala Gln Pro Gly Ala Gln Pro Gly Ala Gln Pro
            85                  90                  95

Gly Ala Gln Pro Gly Ala Gln Pro Gly Ala Gln Pro Gly Ala Gln Pro
            100                 105                 110

Gly Ala Gln Pro Phe Val Glu Gln His Leu Cys Gly Ser His Leu Val
            115                 120                 125

Glu Ala Leu Tyr Leu Val Cys Gly Glu Arg Gly Phe Phe Tyr Thr Pro
            130                 135                 140

Lys
145

<210> SEQ ID NO 27
<211> LENGTH: 21
<212> TYPE: PRT
<213> ORGANISM: ARTIFICIAL
<220> FEATURE:
<223> OTHER INFORMATION: Protein

<400> SEQUENCE: 27

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 28
<211> LENGTH: 77
<212> TYPE: PRT
<213> ORGANISM: ARTIFICIAL
<220> FEATURE:
<223> OTHER INFORMATION: Protein

<400> SEQUENCE: 28

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu Gly Gln Ala Pro Gly Gln Ala Pro
        35                  40                  45

Phe Val Asn Gln His Leu Cys Gly Ser His Leu Val Glu Ala Leu Tyr
        50                  55                  60

Leu Val Cys Gly Glu Arg Gly Phe Phe Tyr Thr Pro Lys
65                  70                  75

<210> SEQ ID NO 29
<211> LENGTH: 77
<212> TYPE: PRT
<213> ORGANISM: ARTIFICIAL
<220> FEATURE:
<223> OTHER INFORMATION: Protein

<400> SEQUENCE: 29

Gly Thr Asn Glu Cys Leu Asp Asn Leu Gly Gly Cys Ser His Val Cys

```
1               5                   10                  15
Arg Asp Leu Glu Ile Gly Tyr Glu Cys Leu Cys Pro Glu Gly Phe Gln
            20                  25                  30

Leu Val Ala Gln Arg Arg Cys Glu Gly Gln Glu Pro Gly Gln Glu Pro
            35                  40                  45

Phe Val Asn Gln His Leu Cys Gly Ser His Leu Val Glu Ala Leu Tyr
            50                  55                  60

Leu Val Cys Gly Glu Arg Gly Phe Phe Tyr Thr Pro Lys
65                  70                  75

<210> SEQ ID NO 30
<211> LENGTH: 101
<212> TYPE: PRT
<213> ORGANISM: ARTIFICIAL
<220> FEATURE:
<223> OTHER INFORMATION: Protein

<400> SEQUENCE: 30

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu Gly Gln Glu Pro Gly Gln Glu Pro
            35                  40                  45

Gly Gln Glu Pro Gly Gln Glu Pro Gly Gln Glu Pro Gly Gln Glu Pro
            50                  55                  60

Gly Gln Glu Pro Gly Gln Glu Pro Phe Val Asn Gln His Leu Cys Gly
65                  70                  75                  80

Ser His Leu Val Glu Ala Leu Tyr Leu Val Cys Gly Glu Arg Gly Phe
                85                  90                  95

Phe Tyr Thr Pro Lys
            100

<210> SEQ ID NO 31
<211> LENGTH: 85
<212> TYPE: PRT
<213> ORGANISM: ARTIFICIAL
<220> FEATURE:
<223> OTHER INFORMATION: Protein

<400> SEQUENCE: 31

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu Gly Gln Glu Pro Gly Gln Glu Pro
            35                  40                  45

Gly Gln Glu Pro Gly Gln Glu Pro Phe Val Asn Gln His Leu Cys Gly
            50                  55                  60

Ser His Leu Val Glu Ala Leu Tyr Leu Val Cys Gly Glu Arg Gly Phe
65                  70                  75                  80

Phe Tyr Thr Pro Lys
            85

<210> SEQ ID NO 32
<211> LENGTH: 93
<212> TYPE: PRT
<213> ORGANISM: ARTIFICIAL
<220> FEATURE:
```

<223> OTHER INFORMATION: Protein

<400> SEQUENCE: 32

Gly Thr Asn Glu Cys Leu Asp Asn Leu Gly Gly Cys Ser His Val Cys
1               5                   10                  15
Arg Asp Leu Glu Ile Gly Tyr Glu Cys Leu Cys Pro Glu Gly Phe Gln
            20                  25                  30
Leu Val Ala Gln Arg Arg Cys Glu Gly Gln Glu Pro Gly Gln Glu Pro
        35                  40                  45
Gly Gln Glu Pro Gly Gln Glu Pro Gly Gln Glu Pro Gly Gln Glu Pro
    50                  55                  60
Phe Val Asn Gln His Leu Cys Gly Ser His Leu Val Glu Ala Leu Tyr
65                  70                  75                  80
Leu Val Cys Gly Glu Arg Gly Phe Phe Tyr Thr Pro Lys
                85                  90

<210> SEQ ID NO 33
<211> LENGTH: 29
<212> TYPE: PRT
<213> ORGANISM: ARTIFICIAL
<220> FEATURE:
<223> OTHER INFORMATION: Protein

<400> SEQUENCE: 33

Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys
            20                  25

<210> SEQ ID NO 34
<211> LENGTH: 40
<212> TYPE: PRT
<213> ORGANISM: ARTIFICIAL
<220> FEATURE:
<223> OTHER INFORMATION: Protein

<400> SEQUENCE: 34

Gly Thr Asn Glu Cys Leu Asp Asn Leu Gly Gly Cys Ser His Val Cys
1               5                   10                  15
Arg Asp Leu Glu Ile Gly Tyr Glu Cys Leu Cys Pro Glu Gly Phe Gln
            20                  25                  30
Leu Val Ala Gln Arg Arg Cys Glu
        35                  40

BIFUNCTIONAL COMPOUNDS COMPRISING INSULIN PEPTIDES AND EGF(A) PEPTIDES

CROSS-REFERENCE TO RELATED APPLICATIONS

This application is a 35 U.S.C. § 371 National Stage application of International Application PCT/EP2019/076889 (WO 2020/070276), filed Oct. 4, 2019, which claims priority to European Patent Application 18198892.4, filed Oct. 5, 2018; the contents of which are incorporated herein by reference.

TECHNICAL FIELD

The present invention relates to novel bi-functional fusion peptides comprising insulin analogues or derivatives thereof and EGF(A) analogues, and their pharmaceutical use. Furthermore, the invention relates to pharmaceutical compositions comprising such bi-functional fusion peptides, and to the use of such fusion peptides for the treatment or prevention of medical conditions relating to diabetes and dyslipidaemia associated with diabetes.

INCORPORATION-BY-REFERENCE OF THE SEQUENCE LISTING

The present application is filed with a Sequence Listing in electronic form. The entire contents of the sequence listing are hereby incorporated by reference.

BACKGROUND

Diabetes mellitus is a metabolic disorder, in which the ability to utilise glucose is partly or completely lost. More than 5% of the global population live with diabetes, with millions more at risk of developing the disease. Insulin therapy for the treatment of diabetes has been used for decades and involves administering several injections of insulin each day. Such therapy usually involves administration of a long-acting basal injection once or twice daily, and an injection of a fast-acting insulin at mealtime (i.e. prandial insulin). Patients with Type 2 diabetes mellitus, in addition to hyperglycemia, often suffer from various metabolic dysfunctions, such as e.g. dyslipidemia, obesity and cardiovascular complications for which current insulin therapy only has limited beneficial effect. Diabetic dyslipidaemia, characterised by elevated LDL-c (low density lipoprotein cholesterol), low HDL and elevated triglycerides, is a well-established driver for cardiovascular disease (CVD).

Statins have been used for the treatment of dyslipidemia for decades and its administration shows substantial and consistent reduction of cardiovascular events with an acceptable safety profile. Despite the availability and widespread use of statins and other lipid lowering agents, many patients do not reach their target LDL-C levels and remain at high risk for developing CVD.

PCSK9 (Proprotein Convertase Subtilisin/Kexin type 9) promotes hepatic LDL-R (LDL receptor) degradation, thereby reducing hepatic LDL-R surface expression and consequently reducing clearance of LDL particles. Conversely, blocking PCSK9 increases the clearance of LDL-C as well as of other atherogenic lipoproteins, such as intermediate-density lipoproteins and remnant particles. This additional clearance may have therapeutic benefits beyond that provided by LDL reduction alone.

The EGF(A) (Epidermal Growth Factor-like domain A) sequence (40 amino acids) of the LDL-R (LDL-R-(293-332)) is well recognized as the site for PCSK9 binding. The isolated wild-type EGF(A) peptide has been shown to inhibit the binding of PCSK9 to the LDL-R with an $IC_{50}$ in the low µM range (Biochemical and Biophysical Research Communications 375 (2008) 69-73). This poor binding affinity prevents a practical pharmaceutical use of the EGF(A) peptide.

WO2012177741 and J. Mol. Biol. (2012) 422, 685-696, allegedly disclose analogues of EGF(A) and Fc-Fusion thereof. WO 2015/127273 allegedly discloses fusion of an anti-PCSK9 and a GLP-1.

WO2017121850 allegedly discloses EGF(A) analogues with fatty acid substituents.

Two anti-PCSK9 antibodies, alirocumab (Praluent®, Sanofi-Aventis) and evolocumab (Repatha®, Amgen Europe BV, have recently been approved for the treatment of high LDL-C levels, being administered by subcutaneous injection every two weeks.

Insulin therapy is well-established for regulating blood glucose levels in patients with diabetes. It is also well-known that patients with a high risk of CVD and are at risk of developing microvascular complications (like nephropathy, retinopathy and neuropathy). With current therapies, still about 50% of people with diabetes die of cardiovascular disease. Thus, there is currently a strong need to provide a treatment that can combine the effects of blood glucose lowering together with reduction of LDL cholesterol.

SUMMARY

In the broadest aspect, the present invention relates to combining insulin with EGF(A).

In another aspect, the compounds of the present invention comprise an insulin peptide or an analogue thereof, an EGF(A) peptide or an analogue thereof, a spacer and a substituent.

In another aspect, the compounds of the present invention are fusion proteins comprising an insulin peptide or an analogue thereof, an EGF(A) peptide or an analogue thereof, a spacer and a substituent.

In another aspect, the fusion proteins of the present invention comprise an insulin peptide, an EGF(A) peptide, a spacer and a substituent, wherein,
   i. said insulin peptide is human insulin (SEQ ID NO: 2 and 3) or an analogue of human insulin
   ii. said EGF(A) peptide is an analogue of the EGF(A) domain of LDL-R (293-332) (SEQ ID NO:1)
   iii. said spacer is a peptide linker comprising segments of (GAQP)n or (GQAP)n, wherein n=1-20, and connecting the N-terminal of the insulin analogue B-chain with the C-terminal of the EGF(A) analogue.
   iv. said substituent is of formula (I): Acy-$AA2_m$-$AA3_p$-, wherein Acy is a fatty diacid comprising from about 16 to about 20 carbon atoms, AA2 is an acidic amino acid residue and wherein m is an integer in the range from 1 to 10 and AA3 is a neutral, alkyleneglycol-containing amino acid residue and p is an integer in the range from 1 to 10, and wherein the maximum number of AA2 and AA3 residues is 10 and wherein the AA2 and AA3 residues may appear in any order, or a pharmaceutically acceptable salt, amide, or ester thereof.

Since people with diabetes requiring insulin administration are in the high CVD risk group, including a LDLc lowering property in the insulin compound provides improved therapy for diabetic patients, in particular providing cholesterol lowering, treating dyslipidaemia and lowering the risk of CVD.

In one aspect, the bi-functional fusion proteins of the present invention lower blood glucose levels and bind PCSK9 thereby enhancing the expression of functional LDL-R in the liver.

In one aspect, the present invention provides novel bi-functional fusion proteins able to both activate the insulin receptor and bind PCSK9, i.e., combine the effects of blood glucose lowering together with reduction of LDL cholesterol.

In another aspect, the bi-functional fusion peptides of the present invention lower blood glucose levels and binds PCSK9 thereby enhancing the expression of functional LDL-R in the liver.

In another aspect the fusion peptides of the present invention reduce blood glucose levels.

In another aspect the fusion peptides of the present invention reduce LDL cholesterol.

In another aspect, the invention relates to a pharmaceutical composition comprising a fusion peptide according to the invention.

In another aspect, the invention relates to a fusion peptide according to the invention for use as a medicament.

In another aspect, the invention relates to a fusion peptide according to the invention for use in the treatment of diabetes and dyslipidaemia associated with diabetes.

In another aspect, the invention relates to medical use(s) of the fusion peptides according to the invention.

The invention may also solve further problems that will be apparent from the disclosure of the exemplary embodiments.

DESCRIPTION

Figure 1:
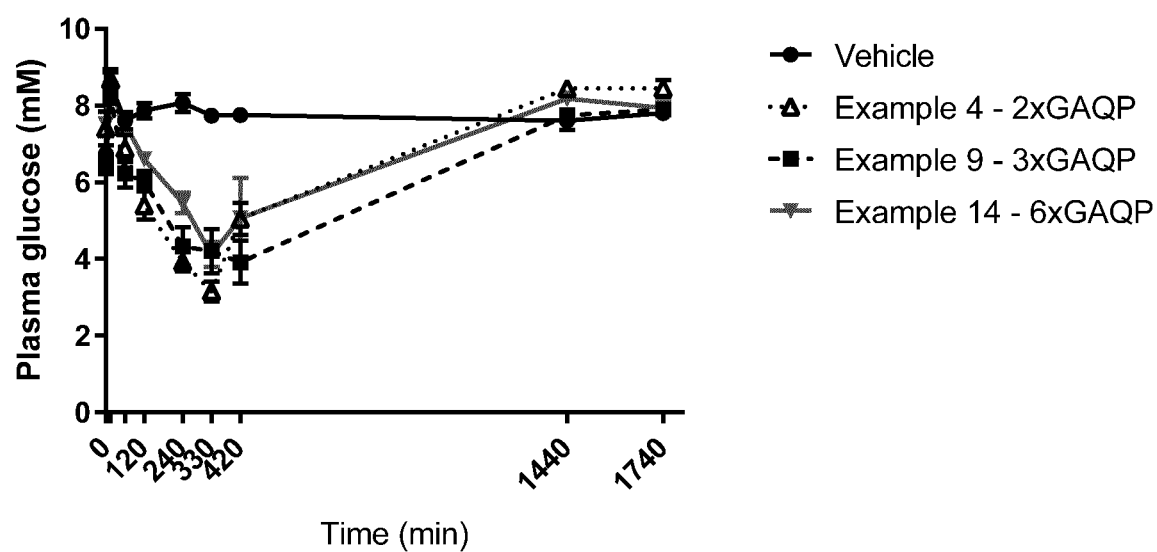
FIG. 1 shows the blood glucose lowering effects of the compounds of examples 4, 9, and 14 of the invention, all with the octadecanedioyl-gGlu-2×OEG side chain and with different lengths of GQAP/GAQP spacers.

The present invention relates to bi-functional compounds which activate the insulin receptor and bind to PCSK9.

In one embodiment, the present invention relates to a fusion protein comprising an insulin peptide and an EGF(A) peptide.

In one embodiment, the invention relates to a fusion protein comprising an insulin analogue and an EGF(A) analogue, wherein said insulin analogue is an analogue of human insulin (SEQ ID NOs: 2 and 3) and said EGF(A) analogue is an analogue of the EGF(A) domain of LDL-R (293-332) (SEQ ID NO: 1).

In another embodiment, the EGF(A) peptide is an analogue of the peptide of SEQ ID NO: 1.

In one embodiment, the insulin analogue is fused with the C-terminal amino acid of the EGF(A) peptide analogue, via the N-terminal amino acid residue of the insulin analogue B-chain.

In one embodiment, the invention relates to a fusion protein comprising an insulin peptide, an EGF(A) peptide, a spacer and a substituent, wherein,
i. said insulin peptide is human insulin (SEQ ID NOs: 2 and 3) or an analogue of human insulin
ii. said EGF(A) peptide is an analogue of the EGF(A) domain of LDL-R (293-332) (SEQ ID NO:1)
iii. said spacer is a peptide linker comprising segments of (GAQP)n or (GQAP)n, wherein n=1-20, and connecting the N-terminal of the insulin analogue B-chain with the C-terminal of the EGF(A) analogue
iv. said substituent is of formula (I): Acy-$AA2_m$-$AA3_p$-, wherein Acy is a fatty diacid comprising from about 16 to about 20 carbon atoms, AA2 is an acidic amino acid residue and wherein m is an integer in the range from 1 to 10 and AA3 is a neutral, alkyleneglycol-containing amino acid residue and p is an integer in the range from 1 to 10, and
wherein the maximum number of AA2 and AA3 residues is 10 and
wherein the AA2 and AA3 residues may appear in any order,
or a pharmaceutically acceptable salt, amide, or ester thereof.

In one embodiment, the insulin analogue is fused with the C-terminal amino acid of the EGF(A) peptide analogue, via the B1 amino acid residue of the insulin analogue N-terminal B-chain.

In one embodiment, the insulin analogue is fused with the C-terminal amino acid of the EGF(A) peptide analogue, via the N-terminal amino acid residue of the insulin analogue B-chain, via a spacer.

In one embodiment, the insulin analogue is fused with the C-terminal amino acid of the EGF(A) peptide analogue, via the N-terminal amino acid residue of the insulin analogue B-chain via a spacer comprising segments of (GAQP)n or (GQAP)n, wherein n=2-19.

Since people with diabetes requiring insulin administration are in the high CVD risk group, including a LDLc lowering property in the insulin fusion peptide will provide improved therapy for diabetic patients and lower their CVD risk.

In one embodiment, the fusion peptides of the present invention reduce blood glucose levels.

In another embodiment, the fusion peptides of the present invention show superior blood glucose reductions relative to comparator fusion peptides comprising (GQEP)n.

In one embodiment, the fusion peptides of the present invention combine the effects of blood glucose lowering together with reduction of LDL cholesterol.

In another embodiment, the invention relates to a pharmaceutical composition comprising a fusion peptide according to the invention.

In another embodiment, the invention relates to a pharmaceutical composition comprising a fusion peptide of the invention and a pharmaceutically acceptable excipient.

In another embodiment, the invention relates to a fusion peptide according to the invention for use as a medicament.

In another embodiment, the invention relates to a fusion peptide according to the invention for use in the treatment of diabetes and dyslipidaemia associated with diabetes.

In another embodiment, the invention relates to medical use of the fusion peptides according to the invention.

General Definitions

The term "compound" is used herein to refer to a molecular entity, and "compounds" may thus have different structural elements besides the minimum element defined for each compound or group of compounds. It follows that a compound may be a fusion compound/peptide or a derivative thereof, as long as the compound comprises the defined structural and/or functional elements. The term "compound" is also meant to cover pharmaceutically relevant forms hereof, i.e. the invention relates to a compound as defined herein or a pharmaceutically acceptable salt, amide, or ester thereof.

The term "peptide" or "polypeptide", as e.g. used in the context of the invention, refers to a compound which comprises a series of amino acids interconnected by amide (or peptide) bonds. In a particular embodiment the peptide consists of amino acids interconnected by peptide bonds.

The term "analogue" generally refers to a peptide, the sequence of which has one or more amino acid changes when compared to a reference amino acid sequence. Analogues "comprising" certain specified changes may comprise further changes, when compared to their reference sequence. In particular embodiments, an analogue "has" or "comprises" specified changes. In other particular embodiments, an analogue "consists of" the changes. When the term "consists" or "consisting" is used in relation to an analogue e.g. an analogue consists or consisting of a group of specified amino acid mutations, it should be understood that the specified amino acid mutations are the only amino acid mutations in the analogue. In contrast an analogue "comprising" a group of specified amino acid mutations may have additional mutations. In the context of this application, the term "analogue" also designates analogues of EGF(A) human insulin fusion proteins.

The term "derivative" generally refers to a compound which may be prepared from a native peptide or an analogue thereof by chemical modification, in particular by covalent attachment of one or more substituents. A derivative can also be referred to as an acylated analogue.

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification).

In general, amino acid residues (peptide/protein sequences) as used herein, may be identified by their full name, their one-letter code, and/or their three-letter code. These three ways are fully equivalent and interchangeable. In what follows, each amino acid of the peptides of the invention for which the optical isomer is not stated is to be understood to mean the L-isomer (unless otherwise specified). Amino acids are molecules containing an amino group and a carboxylic acid group, and, optionally, one or more additional groups, often referred to as a side chain. Herein, the term "amino acid residue" is an amino acid from which, formally, a hydroxy group has been removed from a carboxy group and/or from which, formally, a hydrogen atom has been removed from an amino group.

The terms "fusion" and "fused" are used in relation to compound comprising two individually defined peptide/protein sequences which are connected by a peptide bond or by a peptide spacer (also connected by peptide bonds).

Insulin

The term "human insulin" as used herein means the human insulin hormone whose structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

The human insulin A-chain has the following sequence: GIVEQCCTSICSLYQLENYCN (SEQ ID NO: 2), while the B-chain has the following sequence: FVNQHLCGSHLVEALYLVCGERGFFYTPKT (SEQ ID NO: 3).

In the human body, the hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

"An insulin" according to the invention is herein to be understood as human insulin or an insulin from another species such as porcine or bovine insulin.

The term "insulin peptide", "insulin compound" or "insulin" as used herein means a peptide which is either human insulin or an analogue or a derivative thereof with insulin activity, i.e., which activates the insulin receptor.

Insulin Analogue

The term "insulin analogue" as used herein means the modified human insulin wherein one or more amino acid residues of the insulin have been substituted by other amino acid residues and/or wherein one or more amino acid residues have been deleted from the insulin and/or wherein one or more amino acid residues have been added and/or inserted to the insulin.

The term "mutation" as used herein, means substitution or deletion of amino acids within the sequence of human insulin. The term mutation does not include additions, elongations or extensions to the sequence of human insulin. Mutations in the insulin molecule are denoted stating the chain (A or B), the position, and the one or three letter code for the amino acid residue substituting the native amino acid residue.

Any mutation to the insulin analogue as used herein, means a mutation to the insulin peptide alone and does not include any spacer peptide attached to the insulin peptide/analogue.

By "connecting peptide" or "C-peptide" is meant a connection moiety "C" of the B-C-A polypeptide sequence of a single chain proinsulin-molecule. In the human insulin chain, the C-peptide connects position 30 of the B chain and position 1 of the A chain and is 35 amino acid residue long. In human insulin, the connecting peptide includes two terminal dibasic amino acid sequences, e.g., Arg-Arg and Lys-Arg which serve as cleavage sites for cleavage off of the connecting peptide from the A and B chains to form the two-chain insulin molecule.

By "desB30" or "B(1-29)" is meant a natural insulin B chain or an analogue thereof lacking the B30 amino acid and "A(1-21)" means the natural insulin A chain. Thus, e.g., desB30 human insulin is an analogue of human insulin where the amino acid in position 30 in the B chain is deleted.

Herein terms like "A1", "A2" and "A3" etc. indicates the amino acid in position 1, 2 and 3 etc., respectively, in the A chain of insulin (counted from the N-terminal end). Similarly, terms like B1, B2 and B3 etc. indicates the amino acid in position 1, 2 and 3 etc., respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are A21Ala, A21Gly and A21Gln, respectively.

In one embodiment, the analogue of human insulin or derivative of the invention have the ability to reduce blood glucose levels.

In one embodiment, the analogue of human insulin or derivative of the invention activates the insulin receptor.

In one embodiment, the analogue of human insulin or derivative of the invention lowers blood glucose.

In one embodiment, the fusion peptide of the present invention comprises an analogue of human insulin or a derivative thereof.

In one embodiment, the fusion peptide of the present invention comprises an analogue of human insulin comprising up to 12 mutations.

In one embodiment, the fusion peptide of the present invention comprises an analogue of human insulin comprising up to 10 mutations.

In one embodiment, the fusion peptide of the present invention comprises an analogue of human insulin comprising 1-6 mutations.

In one embodiment, the fusion peptide of the present invention comprises an analogue of human insulin comprising 1-3 mutations.

In one embodiment, the fusion peptide of the present invention comprises an analogue of human insulin comprising one mutation.

In one embodiment, the fusion peptide of the present invention comprises an analogue of human insulin comprising two mutations.

In one embodiment, the fusion peptide of the present invention comprises an analogue of human insulin comprising three mutations.

In one embodiment, the fusion peptide of the present invention comprises an analogue of human insulin comprising four mutations.

In one embodiment, the fusion peptide of the present invention comprises an analogue of human insulin comprising five mutations.

In one embodiment, the fusion peptide of the present invention comprises an analogue of human insulin comprising six mutations.

In one embodiment, the fusion peptide of the present invention comprises an analogue of human insulin comprising seven mutations.

In one embodiment, the fusion peptide of the present invention comprises an analogue of human insulin comprising eight mutations.

In one embodiment, the fusion peptide of the present invention comprises an analogue of human insulin comprising nine mutations.

In one embodiment, the fusion peptide of the present invention comprises an analogue of human insulin comprising 10 mutations.

In one embodiment, the fusion peptide of the present invention comprises human insulin.

In one embodiment, the fusion peptide of the present invention comprises an insulin analogue comprising desB30.

In one embodiment, the fusion peptide of the present invention comprises an insulin analogue comprising A14E.

In one embodiment, the fusion peptide of the present invention comprises an insulin analogue comprising B3E.

In one embodiment, the fusion peptide of the present invention comprises an insulin analogue comprising A14E, desB30.

In one embodiment, the fusion peptide of the present invention comprises an insulin analogue comprising B3E, desB30.

In one embodiment, the fusion peptide of the present invention comprises an insulin analogue comprising desB30 and further 9 mutations in said insulin analogue.

In one embodiment, the fusion peptide of the present invention comprises an insulin analogue comprising desB30 and further 8 mutations in said insulin analogue.

In one embodiment, the fusion peptide of the present invention comprises an insulin analogue comprising desB30 and further 7 mutations in said insulin analogue.

In one embodiment, the fusion peptide of the present invention comprises an insulin analogue comprising desB30 and further 6 mutations in said insulin analogue.

In one embodiment, the fusion peptide of the present invention comprises an insulin analogue comprising desB30 and further 5 mutations in said insulin analogue.

In one embodiment, the fusion peptide of the present invention comprises an insulin analogue comprising desB30 and further 4 mutations in said insulin analogue.

In one embodiment, the fusion peptide of the present invention comprises an insulin analogue comprising desB30 and further 3 mutations in said insulin analogue.

In one embodiment, the fusion peptide of the present invention comprises an insulin analogue comprising desB30 and further 2 mutations in said insulin analogue.

In one embodiment, the fusion peptide of the present invention comprises an insulin analogue comprising desB30 and further one mutation in said insulin analogue.

EGF(A)

The term "EGF(A) compound" or "EGF(A) peptide" is used herein to generally refer to a fusion protein comprising an EGF(A) peptide, encompassing wt-LDL-R (293-332) as defined by SEQ ID NO: 1 and analogues hereof. The term EGF(A) compound encompasses derivatives of EGF-(A) peptide and analogue thereof i.e. EGF(A) peptide analogues with an acyl moiety as described herein is a typical example of an EGF(A) compound. The term "EGF(A) analogue" herein refers to a modified EGF(A) domain of LDL-R (293-332) (SEQ ID NO: 1).

The terms "EGF(A) domain of the LDL-R", "LDL-R (293-332)", "native LDL-R (293-332), "EGF(A) (293-332)", "wild-type EGF(A)", "wt-EGF(A)" or "native EGF(A)" as used herein refer to a peptide consisting of the sequence SEQ ID NO: 1, which is:

Gly-Thr-Asn-Glu-Cys-Leu-Asp-Asn-Asn-Gly-Gly-Cys-Ser-His-Val-Cys-Asn-Asp-Leu-Lys-Ile-Gly-Tyr-Glu-Cys-Leu-Cys-Pro-Asp-Gly-Phe-Gln-Leu-Val-Ala-Gln-Arg-Arg-Cys-Glu.

In this formula the numbering of the amino acid residues follows the numbering for the EGF(A) domain of the LDL-R (LDL-R-(293-332)), wherein the first (N-terminal) amino acid residue is numbered or accorded position no. 293, and the subsequent amino acid residues towards the C-terminus are numbered 294, 295, 296 and so on, until the last (C-terminal) amino acid residue, which in the EGF(A) domain of the LDL-R is Glu with number 332.

The numbering is done differently in the sequence listing, where the first amino acid residue of SEQ ID NO: 1 (Gly) is assigned no. 1, and the last (Glu) no. 40. The same applies for the other sequences of the sequence listing, i.e. the N-terminal amino acid assigned is no. 1 irrespective of its positioning relative to 293Gly or 293 substituting amino acid residue by reference to LDL-R(293-332). However, herein the numbering of amino acid positions is with reference to LDL-R(293-332), as explained above.

EGF(A) Analogue

The term "EGF(A) analogue" generally refers to a peptide, the sequence of which has one or more amino acid changes when compared to a reference amino acid sequence.

The terms "EGF(A) domain of LDL-R (293-332)", "EGF (A) domain of LDL-R (293-332) analogue of SEQ ID NO: 1", "LDL-R(293-332) analogue", "EGF(A) analogue" or "analogue of SEQ ID NO: 1" as used herein may be referred to as a peptide, the sequence of which comprises mutations, i.e. amino acid substitutions or deletions relative to sequence SEQ ID NO: 1.

Any mutation to the EGF(A) analogue as used herein, means a mutation to the EGF(A) peptide alone and does not include any spacer peptide attached to the EGF(A) peptide/analogue.

In one embodiment, the EGF(A) domain of LDL-R (293-332) according to SEQ ID NO:1, or analogue thereof, is capable of inhibiting PCSK9 binding to human Low Density Lipoprotein Receptor (LDL-R).

In one embodiment, the EGF(A) domain of LDL-R (293-332) according to SEQ ID NO:1, or analogue thereof, has the ability to inhibit PCSK9 binding to the LDL-R.

In one embodiment, the EGF(A) domain of LDL-R (293-332) according to SEQ ID NO:1, or analogue thereof, has the ability to inhibit PCSK9 binding to the LDL-R and reduce LDL levels in the blood.

In one embodiment, the EGF(A) domain of LDL-R (293-332) according to SEQ ID NO:1, or analogue thereof, reduces LDL blood levels.

In one embodiment, the fusion peptide of the present invention comprises an EGF(A) domain of LDL-R (293-332) analogue of SEQ ID NO: 1, wherein said EGF (A) analogue comprises 1-15 amino acid mutations compared to SEQ ID NO.: 1.

In one embodiment, the fusion peptide of the present invention comprises an EGF(A) domain of LDL-R (293-332) analogue of SEQ ID NO: 1, wherein said EGF (A) analogue comprises 1-10 amino acid mutations compared to SEQ ID NO.: 1.

In one embodiment, the fusion peptide of the present invention comprises an EGF(A) domain of LDL-R (293-332) analogue of SEQ ID NO: 1, wherein said EGF (A) analogue comprises 1-8 amino acid mutations compared to SEQ ID NO.: 1.

In one embodiment, the fusion peptide of the present invention comprises an EGF(A) domain of LDL-R (293-332) analogue of SEQ ID NO: 1, wherein said EGF (A) analogue comprises 1-6 amino acid mutations compared to SEQ ID NO.: 1.

In one embodiment, the fusion peptide of the present invention comprises an EGF(A) domain of LDL-R (293-332) analogue of SEQ ID NO: 1, wherein said EGF (A) analogue comprises 1-5 mutations.

In one embodiment, the fusion peptide of the present invention comprises an EGF(A) domain of LDL-R (293-332) analogue of SEQ ID NO: 1, wherein said EGF (A) analogue comprises one mutation.

In one embodiment, the fusion peptide of the present invention comprises an EGF(A) domain of LDL-R (293-332) analogue of SEQ ID NO: 1, wherein said EGF (A) analogue comprises two mutations.

In one embodiment, the fusion peptide of the present invention comprises an EGF(A) domain of LDL-R (293-332) analogue of SEQ ID NO: 1, wherein said EGF (A) analogue comprises three mutations.

In one embodiment, the fusion peptide of the present invention comprises an EGF(A) domain of LDL-R (293-332) analogue of SEQ ID NO: 1, wherein said EGF (A) analogue comprises four mutations.

In one embodiment, the fusion peptide of the present invention comprises an EGF(A) domain of LDL-R (293-332) analogue of SEQ ID NO: 1, wherein said EGF (A) analogue comprises five mutations.

In one embodiment, the fusion peptide of the present invention comprises an EGF(A) domain of LDL-R (293-332) analogue of SEQ ID NO: 1, wherein said EGF (A) analogue comprises six mutations.

In one embodiment, the fusion peptide of the present invention comprises an EGF(A) domain of LDL-R (293-332) analogue of SEQ ID NO: 1, wherein said EGF (A) analogue comprises seven mutations.

In one embodiment, the fusion peptide of the present invention comprises an EGF(A) domain of LDL-R (293-332) analogue of SEQ ID NO: 1, wherein said EGF (A) analogue comprises eight mutations.

In one embodiment, the fusion peptide of the present invention comprises an EGF(A) domain of LDL-R (293-332) analogue of SEQ ID NO: 1, wherein said EGF (A) analogue comprises nine mutations.

In one embodiment, the fusion peptide of the present invention comprises an EGF(A) domain of LDL-R (293-332) analogue of SEQ ID NO: 1, wherein said EGF (A) analogue comprises 10 mutations.

In other words, the peptide analogues may be described by reference to the native LDL-R(293-332) EGF(A) peptide, namely as an analogue thereof in which a number of amino acid residues have been changed when compared to native LDL-R(293-332) EGF(A) (SEQ ID NO: 1). These changes may represent, independently, one or more amino acid mutations.

The EGF(A) analogue incorporated in fusion peptides of the invention, may be referred to as the following LDL-R (293-332) EGF(A) analogue: (301Leu, 309Arg, 312Glu, 321Glu) LDL-R(293-332) EGF(A), or (Leu301, Arg309, Glu312, Glu321)-LDL-R(293-332) EGF(A) or (301L,309R, 312E,321E) LDL-R(293-332) or (L301,R309,E312,E321) LDL-R(293-332). This means that when this analogue is aligned with native LDL-R(293-332), it has i) a Leu at the position in the analogue which corresponds, according to the alignment, to position 301 in native LDL-R(293-332) EGF (A), ii) an Arg at the position in the analogue which corresponds to position 309 in native LDL-R(293-332) EGF(A), iii) a Glu at the position in the analogue which corresponds to position 312 in native LDL-R(293-332) EGF(A), iv) a Glu at the position in the analogue which corresponds to position 321 in native LDL-R(293-332) EGF(A).

Analogues "comprising" certain specified changes may comprise further changes, when compared to SEQ ID NO: 1.

The EGF(A) peptide analogue within the fusion peptide of the invention comprises the amino acid substitution of amino acid residue 301 from Asn to Leu, also described by Asn301Leu, 301Leu or simply 301L.

In one embodiment, the fusion peptide of the present invention comprises an EGF(A) analogue of SEQ ID NO: 1, wherein said EGF (A) analogue comprises 301Leu.

In one embodiment, the fusion peptide of the present invention comprises an EGF(A) analogue of SEQ ID NO: 1, wherein said EGF (A) analogue comprises 309R.

In one embodiment, the fusion peptide of the present invention comprises an EGF(A) analogue of SEQ ID NO: 1, wherein said EGF (A) analogue comprises 312E.

In one embodiment, the fusion peptide of the present invention comprises an EGF(A) analogue of SEQ ID NO: 1, wherein said EGF (A) analogue comprises 321E.

In one embodiment, the fusion peptide of the present invention comprises an EGF(A) analogue of SEQ ID NO: 1, wherein said EGF (A) analogue comprises 301L and 309R.

In one embodiment, the fusion peptide of the present invention comprises an EGF(A) analogue of SEQ ID NO: 1, wherein said EGF (A) analogue comprises 301L, 309R and 312E.

In one embodiment, the fusion peptide of the present invention comprises an EGF(A) analogue of SEQ ID NO: 1, wherein said EGF (A) analogue comprises 301L, 309R, 312E and 321E.

In one embodiment, the fusion peptide of the present invention comprises an EGF(A) analogue of SEQ ID NO: 1, wherein the EGF(A) peptide analogue comprises the amino acid mutations represented by any of the groups i-vii as listed below:

i. 301Leu
ii. 301Leu and 309Arg
iii. 301Leu and 312Glu
iv. 301Leu and 321Glu
v. 301Leu, 309Arg, 312Glu
vi. 301Leu, 309Arg and 321Glu
vii. 301Leu, 309Arg, 312Glu and 321Glu.

EGF(A) Insulin Fusion Proteins

The compounds or fusion peptides of the present invention comprise an insulin peptide, an EGF(A) peptide and a spacer, wherein, i. said insulin peptide is human insulin (SEQ ID NO:2 and 3) or an analogue of human insulin,
ii. said EGF(A) peptide is an analogue of the EGF(A) domain of LDL-R (293-332) (SEQ ID NO:1) and
iii. said spacer is a peptide linker connecting the N-terminal of the insulin analogue B-chain with the C-terminal of the EGF(A) analogue.

The compounds or fusion peptides of the present invention further comprise a substituent attached to an amino acid residue of the fusion protein.

The names of the EGF(A) insulin fusion proteins are given as analogues and derivative relative to the EGF(A) and human insulin proteins as elaborated above. The naming of the spacer connecting the two proteins and the substituents attached to the fusion protein is elaborated below.

The compounds of the present invention may be called interchangeably "compounds of the invention", "compounds of the present invention", "bi-functional compounds", "fusion proteins of the invention", "fusion proteins of the present invention".

Spacer

Frequently, fusion peptides/proteins include a spacer to ensure that any functionality residing in the ends of the two peptides/proteins is not disturbed by the proximity of the other peptides/proteins.

In one embodiment, the spacer is a peptide, which is herein referred to as a spacer peptide or a peptide spacer or a peptide linker. Various spacer peptides are known in the art and may be placed between the insulin analogue and the EGF(A) analogue to obtain fusion compounds.

When two peptide segments are to be fused the order may influence the functionality of the resulting fusion compound, and derivatives comprising it.

In one embodiment of the invention, the order of the EGF(A) analogue and the insulin analogue starting from the N-terminal is the EGF(A) analogue followed by the insulin analogue, optionally separated by a spacer peptide. In one embodiment, the C-terminal of the EGF(A) analogue is fused with the N-terminal of the insulin analogue B-chain.

In one embodiment, the spacer is a peptide segment consisting of 4-80 amino acids connected via peptide bonds.

In one embodiment, the spacer comprises one or more of the following amino acid residues: Ala (A), Gly (G), Pro (P), Gln (Q).

Surprisingly, the present inventors found that the amino acid composition of the spacer impacted the ability of the compounds to reduce blood glucose levels. Compounds of the invention comprising the uncharged spacers (GQAP)n or (GAQP)n, showed superior blood reduction relative to comparator compounds comprising the charged spacers such as (GQEP)n. Furthermore, it was also found that the length of the spacer impacted the ability of the compounds to reduce blood glucose levels.

TABLE 1

Examples of spacers comprised in the compounds/fusion peptides of the invention and spacers comprised in the comparator compounds

| Spacer # | Short name: | Amino acid sequence |
|---|---|---|
| 1 | [GQAP]2 | GQAPGQAP (SEQ ID NO: 4) |
| 2 | [GAQP]2 | GAQPGAQP (SEQ ID NO: 5) |
| 3 | [GAQP]3 | GAQPGAQPGAQP (SEQ ID NO: 6) |
| 4 | [GAQP]4 | GAQPGAQPGAQPGAQP (SEQ ID NO: 7) |
| 5 | [GAQP]6 | GAQPGAQPGAQPGAQPGAQPGAQP (SEQ ID NO: 8) |
| 6 | [GAQP]8 | GAQPGAQPGAQPGAQPGAQPGAQPGAQPGAQP (SEQ ID NO: 9) |
| 7 | [GAQP]10 | GAQPGAQPGAQPGAQPGAQPGAQPGAQPGAQPGAQPGAQP (SEQ ID NO: 10) |
| 8 | [GAQP]12 | GAQPGAQPGAQPGAQPGAQPGAQPGAQPGAQPGAQPGAQPGAQPGAQP (SEQ ID NO: 11) |
| 9 | [GAQP]19 | GAQPGAQPGAQPGAQPGAQPGAQPGAQPGAQPGAQPGAQPGAQPGAQPGAQPGAQPGAQPGAQPGAQPGAQPGAQP (SEQ ID NO: 12) |

TABLE 1-continued

Examples of spacers comprised in the compounds/fusion peptides of the invention and spacers comprised in the comparator compounds

| Comparator spacer # | Short name: | Amino acid sequence |
|---|---|---|
| 10 | [GQEP]2 | GQEPGQEP (SEQ ID NO: 13) |
| 11 | [GQEP]4 | GQEPGQEPGQEPGQEP (SEQ ID NO: 14) |
| 12 | [GQEP]6 | GQEPGQEPGQEPGQEPGQEPGQEP (SEQ ID NO: 15) |
| 13 | [GQEP]8 | GQEPGQEPGQEPGQEPGQEPGQEPGQEPGQEP (SEQ ID NO: 16) |

The spacer within the EGF(A)-insulin fusion protein derivative of Example 4 is named [GAQP]2, meaning that the spacer connecting the C-terminal residue of the EGF(A) peptide with the N-terminal residue of the insulin B-chain has the sequence $(GAQP)_2$, which also can be denoted GAQPGAQP or 2×GAQP or [GAQP]2 or 2×(GAQP). The amino acid residues may be identified by their full name, their one-letter code, and/or their three-letter code. These three ways are fully equivalent and interchangeable.

Similarly, the spacer within the EGF(A)-insulin fusion protein derivative of Example 2 is named [GAQP]10, meaning that the spacer connecting the C-terminal residue of the EGF(A) peptide with the N-terminal residue of the insulin B-chain has the sequence $(GAQP)_{10}$, which also can be denoted 10×GAQP, [GAQP]10, 10×(GAQP) or GAQP-GAQPGAQPGAQPGAQPGAQPGAQPGAQPGAQP-GAQP.

In one embodiment, the fusion proteins of the present invention show superior blood glucose reductions relative to comparator compounds comprising (GQEP)n.

In one embodiment, the fusion proteins of the present invention wherein the spacer comprises (GAQP)n or (GQAP)n show superior blood glucose reductions relative to comparator compounds comprising (GQEP)n.

In another aspect, the fusion proteins of the present invention wherein the spacer comprises (GAQP)n or (GQAP)n, wherein n=1-20 show superior blood glucose reductions relative to comparator compounds comprising (GQEP)n.

In another aspect, the fusion proteins of the present invention wherein the spacer comprises (GAQP)n or (GQAP)n, wherein n=2-19 show superior blood glucose reductions relative to comparator compounds comprising (GQEP)n.

In another embodiment, the fusion proteins of the present invention wherein the spacer comprises (GAQP)n, wherein n=2-10 show superior blood glucose reductions relative to comparator compounds comprising (GQEP)n.

In another embodiment, the fusion proteins of the present invention wherein the spacer comprises (GAQP)n, wherein n=2-10 show superior blood glucose reductions relative to both comparator compounds comprising (GQEP)n and compounds comprising (GAQP)n, n=12-19.

In one embodiment, the fusion proteins of the present invention comprise a spacer comprising (GAQP)n or (GQAP)n, wherein n=1-20.

In one embodiment, the fusion proteins of the present invention comprise a spacer comprising (GAQP)n or (GQAP)n, wherein n=2-19.

In one embodiment, the fusion proteins of the present invention comprise a spacer comprising (GAQP)n or (GQAP)n, wherein n=2-12.

In one embodiment, the fusion peptides of the present invention comprise a spacer comprising (GAQP)n or (GQAP)n, wherein n=2-10.

In one embodiment, the fusion peptides of the present invention comprise a spacer comprising (GAQP)n or (GQAP)n, wherein n=2-8.

In one embodiment, the fusion peptides of the present invention comprise a spacer comprising (GAQP)n or (GQAP)n, wherein n=2-6.

In one embodiment, the fusion peptides of the present invention comprise a spacer comprising (GAQP)n or (GQAP)n, wherein=2-4.

In one embodiment, the fusion peptides of the present invention comprise a spacer comprising (GAQP)n or (GQAP)n, wherein n=4-6.

In one embodiment, the fusion peptides of the present invention comprise a spacer comprising (GAQP)n or (GQAP)n, wherein n=2.

In one embodiment, the fusion peptides of the present invention comprise a spacer comprising (GAQP)n or (GQAP)n, wherein n=3.

In one embodiment, the fusion peptides of the present invention comprise a spacer comprising (GAQP)n or (GQAP)n, wherein n=4.

In one embodiment, the fusion peptides of the present invention comprise a spacer comprising (GAQP)n or (GQAP)n, wherein n=5.

In one embodiment, the fusion peptides of the present invention comprise a spacer comprising (GAQP)n or (GQAP)n, wherein n=6.

In one embodiment, the fusion peptides of the present invention comprise a spacer comprising (GAQP)n or (GQAP)n, wherein n=7.

In one embodiment, the fusion peptides of the present invention comprise a spacer comprising (GAQP)n or (GQAP)n, wherein n=8.

In one embodiment, the fusion peptides of the present invention comprise a spacer comprising (GAQP)n or (GQAP)n, wherein n=9.

In one embodiment, the fusion peptides of the present invention comprise a spacer comprising (GAQP)n or (GQAP)n, wherein n=10.

In one embodiment, the fusion peptides of the present invention comprise a spacer comprising (GAQP)n or (GQAP)n, wherein n=11.

In one embodiment, the fusion peptides of the present invention comprise a spacer comprising (GAQP)n or (GQAP)n, wherein n=12.

In one embodiment, the fusion peptides of the present invention comprise a spacer comprising (GAQP)n or (GQAP)n, wherein n=13.

In one embodiment, the fusion peptides of the present invention comprise a spacer comprising (GAQP)n or (GQAP)n, wherein n=14.

In one embodiment, the fusion peptides of the present invention comprise a spacer comprising (GAQP)n or (GQAP)n, wherein n=15.

In one embodiment, the fusion peptides of the present invention comprise a spacer comprising (GAQP)n or (GQAP)n, wherein n=16.

In one embodiment, the fusion peptides of the present invention comprise a spacer comprising (GAQP)n or (GQAP)n, wherein n=17.

In one embodiment, the fusion peptides of the present invention comprise a spacer comprising (GAQP)n or (GQAP)n, wherein n=18.

In one embodiment, the fusion peptides of the present invention comprise a spacer comprising (GAQP)n or (GQAP)n, wherein n=19.

In one embodiment, the fusion peptides of the present invention comprise a spacer comprising (GAQP)n or (GQAP)n, wherein n=20.

In one embodiment, the fusion peptides of the present invention comprise a spacer consisting of (GAQP)n or (GQAP)n, wherein n=2-19 or [(GAQP)n or (GQAP)n], wherein n=2-10.

In one embodiment, the fusion peptides of the present invention comprise a spacer consisting of (GAQP)n or (GQAP)n, wherein n=2-19 or [(GAQP)n or (GQAP)n], wherein n=2-6.

Substituent

In one embodiment, a substituent/acyl moiety is attached to the fusion protein of the present invention (i.e., bi-functional insulin EGF(A) fusion compound or bi-functional compound).

It is desirable that the substituent has none or minimal effect on the functionality of the EGF(A) peptides and the expected effect on the insulin functionality, i.e., reduction of insulin receptor affinity similar to the effect of attaching an acyl moiety to an insulin without an EGF(A) peptide.

In one embodiment the acyl moiety is attached via a Lys/K amino acid residue within the insulin analogue sequence.

In one embodiment, the substituent attached to the compound of the present invention has the general formula (I): Acy-AA2$_m$-AA3$_p$-, wherein Acy is a fatty diacid comprising from about 16 to about 20 carbon atoms, AA2 is an acidic amino acid residue and wherein m is an integer in the range from 1 to 10 and AA3 is a neutral, alkyleneglycol-containing amino acid residue and p is an integer in the range from 1 to 10, and wherein the maximum number of AA2 and AA3 residues is 10 and wherein the AA2 and AA3 residues may appear in any order, or a pharmaceutically acceptable salt, amide, or ester thereof.

In one embodiment, the substituent has formula (I) Acy-AA2$_m$-AA3$_p$-, wherein said Acy comprises a fatty diacid group selected from 1,16-hexadecanedioic acid, 1,18-octadecanedioic acid, and 1,20-eicosanedioic acid.

In one embodiment, the substituent has formula (I) Acy-AA2$_m$-AA3$_p$-, wherein said Acy comprises a fatty diacid group 1,16-hexadecanedioic acid.

In one embodiment, the substituent has formula (I) Acy-AA2$_m$-AA3$_p$-, wherein said Acy comprises a fatty diacid group 1,18-octadecanedioic acid.

In one embodiment, the substituent has formula (I) Acy-AA2$_m$-AA3$_p$-, wherein said Acy comprises a fatty diacid group 1,20-eicosanedioic acid.

In one embodiment, the substituent has formula (I) Acy-AA2$_m$-AA3$_p$-, wherein said AA2$_m$ comprises gGlu, which represents a gamma glutamic acid residue represented by the following structure:

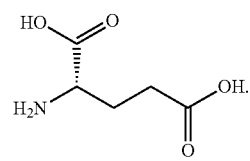

In one embodiment, the substituent has formula (I) Acy-AA2$_m$-AA3$_p$-, wherein said AA3$_p$ comprises [2-(2-aminoethoxy)ethoxy]acetyl or amino acid residue 8-amino-3,6- dioxaoctanoic acid —NH(CH$_2$)$_2$O(CH$_2$)$_2$OCH$_2$CO— and is represented by the following structure:

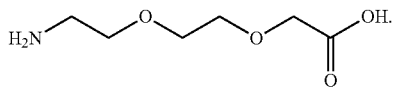 [SMILES: NCCOCCOCC(=O)O]

In one embodiment, the substituent has formula (I) Acy-AA2$_m$-AA3$_p$-, and wherein AA2$_m$-AA3$_p$- is represented independently by gGlu-OEG or gGlu-OEG-OEG.

In one embodiment, the substituent has formula (I) Acy-AA2$_m$-AA3$_p$-, and wherein AA2$_m$-AA3$_p$- is represented by gGlu-OEG.

In one embodiment, the substituent has formula (I) Acy-AA2$_m$-AA3$_p$-, and wherein AA2$_m$-AA3$_p$- is represented by gGlu-OEG-OEG.

In one embodiment, the substituent has formula (I) Acy-AA2$_m$-AA3$_p$- is represented independently by:
 i. C16 diacid-gGlu,
 ii. C18 diacid-gGlu-OEG,
 iii. C18 diacid-gGlu-2×OEG or
 iv. C20 diacid-gGlu-2×OEG.

In one embodiment, the substituent has formula (I) Acy-AA2$_m$-AA3$_p$- is represented by C16 diacid-gGlu.

In one embodiment, the substituent has formula (I) Acy-AA2$_m$-AA3$_p$- is represented by C18 diacid-gGlu-OEG.

In one embodiment, the substituent has formula (I) Acy-AA2$_m$-AA3$_p$- is represented by C18 diacid-gGlu-2×OEG.

In one embodiment, the substituent has formula (I) Acy-AA2$_m$-AA3$_p$- is represented by C20 diacid-gGlu-2×OEG.

leneglycol based chains, i.e., chains that are based on the repeating unit —CH$_2$CH$_2$O—, —CH$_2$CH$_2$CH$_2$O— or —CH$_2$CH$_2$CH$_2$CH$_2$O—. The alkyleneglycol moiety is monodisperse (with well-defined length/molecular weight). Monoalkyleneglycol moieties comprise —OCH$_2$CH$_2$O—, —OCH$_2$CH$_2$CH$_2$O— or —OCH$_2$CH$_2$CH$_2$CH$_2$O— containing different groups at each end.

As mentioned herein, the order by which AA2 and AA3 appears in the acyl moiety with the formula (I) (Acy-AA2$_m$-AA3$_p$-) can be interchanged independently. Consequently, the formula Acy-AA2$_m$-AA3$_p$- also covers moieties like, e.g., the formula Acy-AA2$_m$-AA3$_p$-, the formula Acy-AA2-AA3$_n$-AA2-, and the formula Acy-AA3$_p$-AA2$_m$-, wherein AcyAA2, AA3, n, m and p are as defined herein.

As mentioned herein, the connections between the moieties Acy, AA2 and/or AA3 are formally obtained by amide bond (peptide bond) formation (—CONH—) by removal of water from the parent compounds from which they formally are build. This means that in order to get the complete formula for the acyl moiety with the formula (I) (Acy-AA2$_m$-AA3$_p$-, wherein Acy, AA2, AA3, m and p are as defined herein), one has, formally, to take the compounds given for the terms Acy, AA2 and AA3 and remove a hydrogen and/or hydroxyl from them and, formally, to connect the building blocks so obtained at the free ends.

For the naming of the substituent, in some instances the naming is done according to IUPAC nomenclature, and in other instances the naming is done as peptide nomenclature.

As an example, the acyl moiety of the compound of example 2 of the following structure:

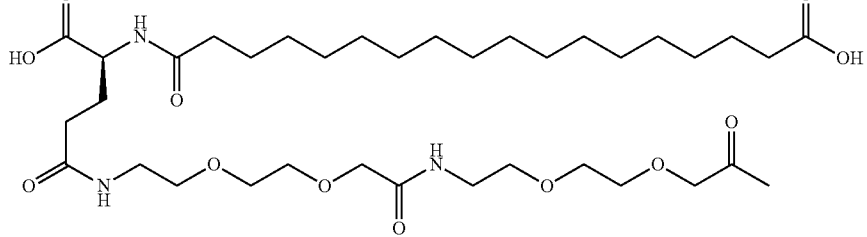

In another embodiment, the acyl moiety attached to the fusion peptides of the present invention has the general formula Acy-AA2$_m$-AA3$_p$- (I), wherein AA2 is selected from L- or D-gGlu, L- or D-Glu, L- or D-Asp, L- or D-homoGlu.

The acidic amino acid residue designated AA2 is an amino acid with a molecular weight of up to about 200 Da comprising two carboxylic acid groups and one primary or secondary amino group.

The neutral, alkyleneglycol-containing amino acid residue designated AA3 is an alkyleneglycol moiety, optionally an oligo- or polyalkyleneglycol moiety containing a carboxylic acid functionality at one end and an amino group functionality at the other end. Herein, the term alkyleneglycol moiety covers mono-alkyleneglycol moieties as well as oligo-alkyleneglycol moieties. Mono- and oligoalkyleneglycols comprises mono- and oligoethyleneglycol based, mono- and oligopropyleneglycol based and mono- and oligobutycan for example be named "octadecanedioyl-gGlu-2× OEG", "octadecanedioyl-gGlu-(OEG)$_2$", "octadecanedioyl-γGlu-2×OEG", "octadecanedioyl-γGlu-(OEG)$_2$", "1,18-octadecanedioyl-gGlu-2×OEG", "(C18 diacid)-gGlu-2× OEG", "C18d-gGlu-2×OEG" or the like, wherein γGlu (and gGlu) is short hand notation for the amino acid gamma glutamic acid in the L-configuration, and "2×" means that the residue following is repeated 2 times.

Gamma Glu, γGlu and gGlu are short hand notation for the amino acid gamma glutamic acid, H$_2$N—CH(CO$_2$H)—CH$_2$CH$_2$—CO$_2$H (connected via the alpha amino group and via the gamma (side chain) carboxy group), in the L-configuration.

OEG is short hand notation for the amino acid residue 8-amino-3,6-dioxa-octanoic acid, NH$_2$(CH$_2$)$_2$O(CH$_2$)$_2$OCH$_2$CO$_2$H.

In one embodiment, the substituent of formula Acy-AA2$_m$-AA3$_p$-, is represented by:
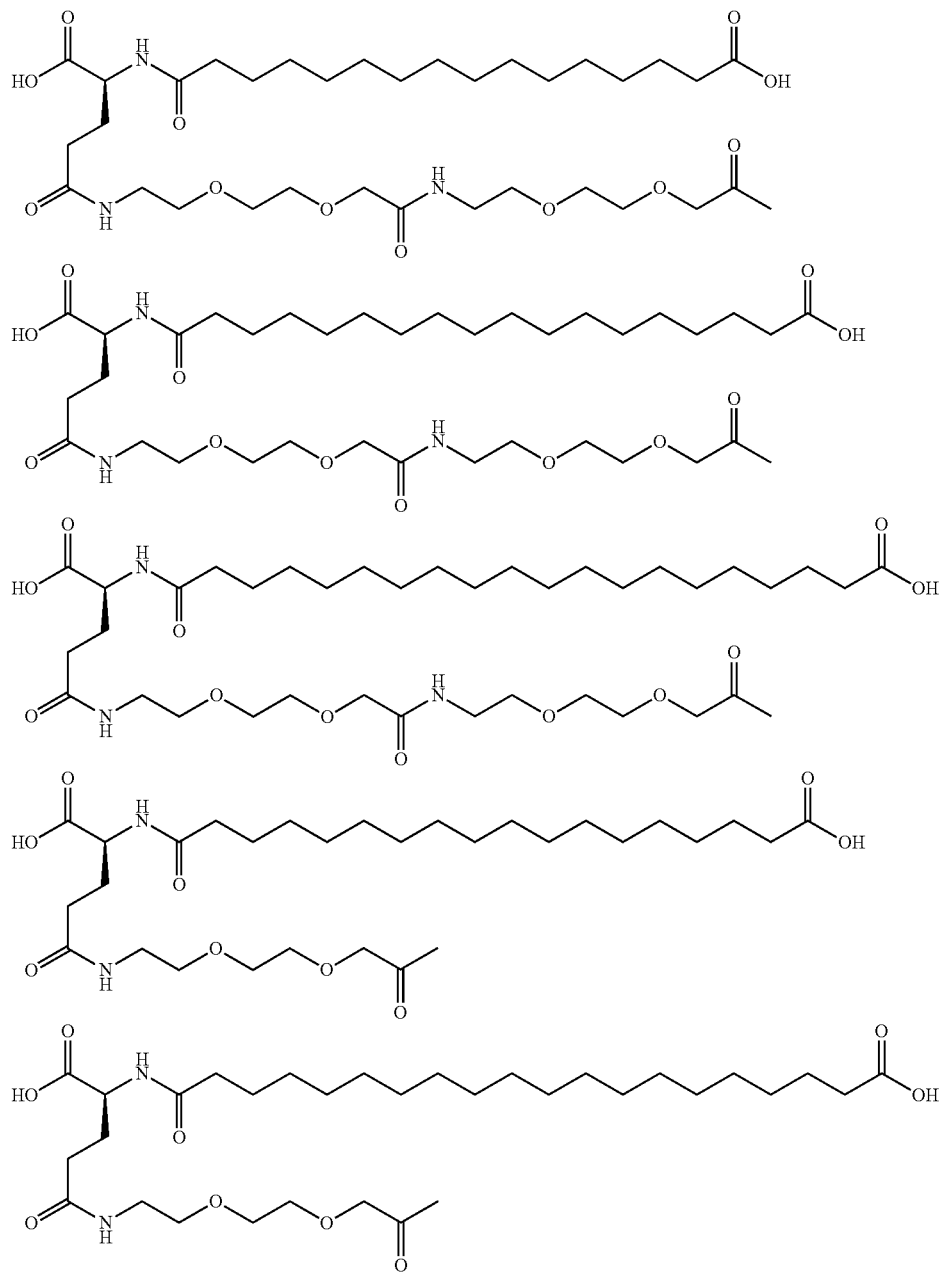
In one embodiment, the substituent of formula Acy-AA2$_m$-AA3$_p$-, is represented by:
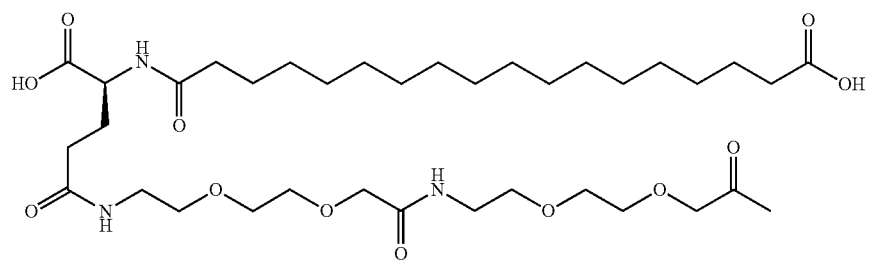 [SMILES: CC(=O)COCCOCCNC(=O)COCCOCCNC(=O)CC[C@H](NC(=O)CCCCCCCCCCCCCCCCC(=O)O)C(=O)O]

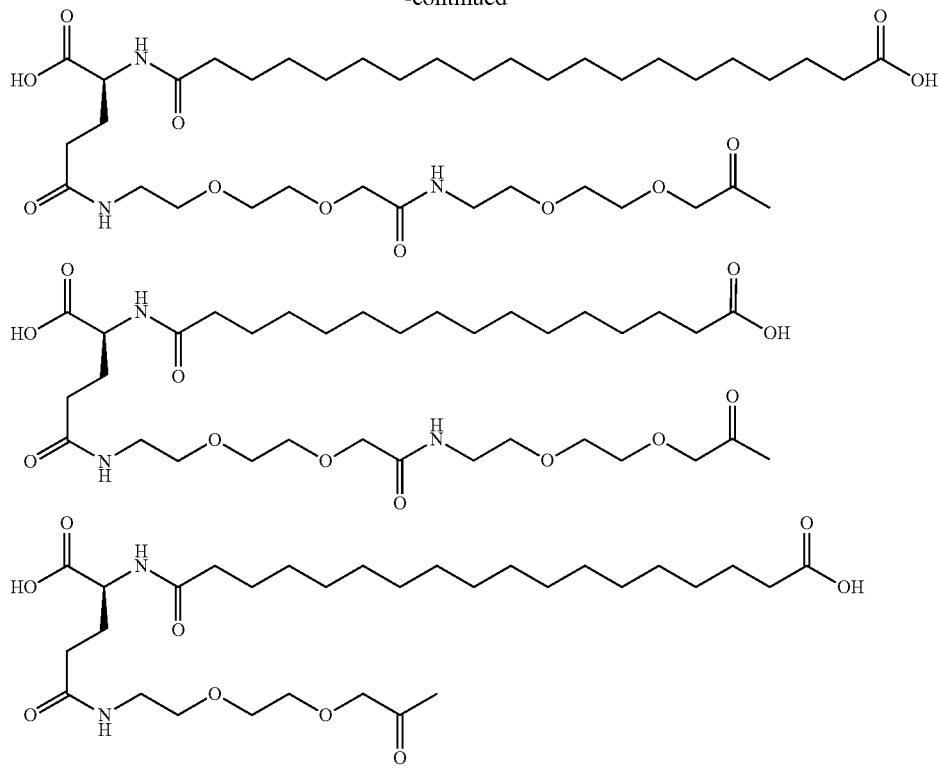

In one embodiment, the substituent of formula Acy-AA2$_m$-AA3$_p$-, is represented by:

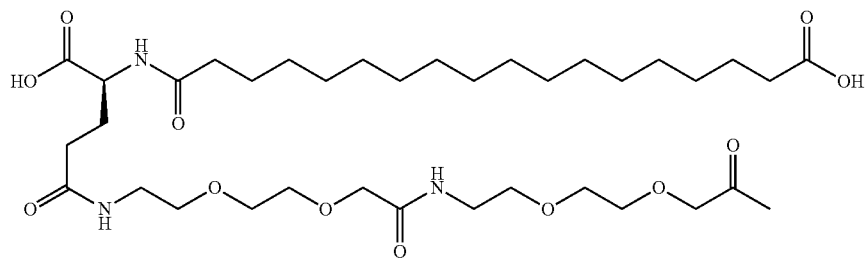 [SMILES: CC(=O)COCCOCCNC(=O)COCCOCCNC(=O)CC[C@H](NC(=O)CCCCCCCCCCCCCCCCC(=O)O)C(=O)O]

In one embodiment, the substituent of formula Acy-AA2$_m$-AA3$_p$-, is represented by:

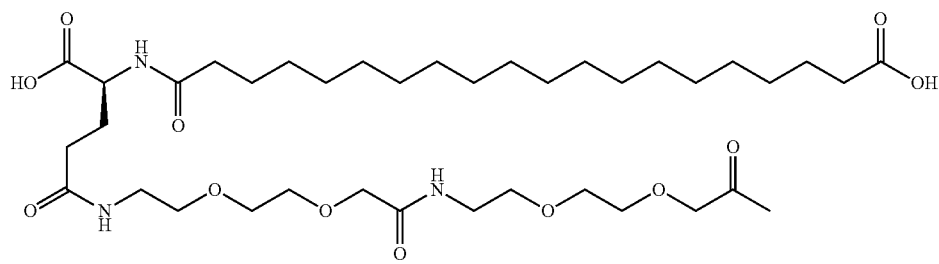 [SMILES: CC(=O)COCCOCCNC(=O)COCCOCCNC(=O)CC[C@H](NC(=O)CCCCCCCCCCCCCCCCCCC(=O)O)C(=O)O]

Any of the above non-limiting examples of the substituent of formula Acy-AA2$_m$-AA3$_p$- can be attached to an epsilon amino group of a lysine residue present in any of the compounds of the invention thereby giving further specific examples of acylated compounds of this invention. The desired group of the formula Acy-AA2$_m$-AA3$_p$- can be introduced by any convenient method and many methods are disclosed in the prior art for such reactions.

Combining the nomenclature elaborated above, the EGF (A)-insulin fusion compound derivative of Example 1 is named "EGF(A)(301L, 309R, 312E, 321E)-[GAQP]2-Insulin(B3E, B29K(hexadecanedioyl-gGlu-2×OEG), desB30)"

to indicate that the EGF(A) peptide contains the substitutions 301L, 309R, 312E, 321E relative to native EGF(A), the insulin peptide contains the substitutions B3E and desB30, and the lysine in the insulin B29 position has been derivatised (acylated) with the hexadecanedioyl-gGlu-2×OEG moiety. The spacer connecting the C-terminal residue of the EGF(A) peptide with the N-terminal residue of the insulin B-chain has the sequence (GAQP)$_2$, which also can be denoted GAQPGAQP or 2×GAQP or [GAQP]2.

Similarly, the EGF(A)-insulin fusion protein derivative of Example 2 is named EGF(A)(301L, 309R, 312E, 321E)-[GAQP]10-Insulin(B29K(octadecanedioyl-gGlu-2×OEG), desB30) to indicate that the EGF(A) peptide contains the substitutions 301L, 309R, 312E, 321E relative to native EGF(A), the insulin peptide contains the substitution desB30, and the lysine in the insulin B29 position has been derivatised (acylated) with the octadecanedioyl-gGlu-2× OEG moiety. The spacer connecting the C-terminal residue of the EGF(A) peptide with the N-terminal residue of the insulin B-chain has the sequence (GAQP)$_{10}$, which also can be denoted 10×GAQP, [GAQP]10 or GAQPGAQPGAQPGAQPGAQPGAQPGAQPGAQPGAQPGAQP.

Throughout this application, both formulas and names of preferred compounds of the invention are given.

In one embodiment, the invention relates to compounds selected from the group of fusion proteins of examples independently selected from 1-18.

In one embodiment, the invention relates to compounds selected from the group of fusion proteins of examples independently selected from 1 and 3-17.

In one embodiment, the invention relates to compounds selected from the group of fusion proteins of examples independently selected from 1 and 3-16.

In one embodiment, the invention relates to compounds selected from the group of fusion proteins of examples independently selected from 1 and 3-12.

In one embodiment, the invention relates to compounds selected from the group of fusion proteins of examples independently selected from 1 and 3-8.

In one embodiment the invention relates to fusion peptide of example 1: EGF(A)(301L, 309R, 312E, 321E)-[GAQP]2-Insulin(B3E, B29K(hexadecanedioyl-gGlu-2×OEG), desB30) and represented by Chem.1.

In one embodiment the invention relates to fusion peptide of example 3: EGF(A)(301L, 309R, 312E, 321E)-[GAQP]2-Insulin(B3E, B29K(octadecanedioyl-gGlu-2×OEG), desB30) and represented by Chem.3.

TABLE 2

Examples of compounds of the invention

| Ex. No: | EGF(A) analogue | Spacer | Insulin analogue | Substituent |
|---|---|---|---|---|
| 1(SEQ ID NO: 17 and 2) | 301L, 309R, 312E, 321E | [GAQP]2 | B3E, desB30 | C16d-gGlu-2xOEG |
| 2(SEQ ID NO: 18 and 2) | 301L, 309R, 312E, 321E | [GAQP]10 | desB30 | C18d-gGlu-2xOEG |
| 3(SEQ ID NO: 17 and 2) | 301L, 309R, 312E, 321E | [GAQP]2 | B3E, desB30 | C18d-gGlu-2xOEG |
| 4(SEQ ID NO: 19 and 2) | 301L, 309R, 312E, 321E | [GAQP]2 | desB30 | C18d-gGlu-2xOEG |
| 5(SEQ ID NO: 17 and 2) | 301L, 309R, 312E, 321E | [GAQP]2 | B3E, desB30 | C18d-gGlu-OEG |
| 6(SEQ ID NO: 17 and 2) | 301L, 309R, 312E, 321E | [GAQP]2 | B3E, desB30 | C20d-gGlu-2xOEG |
| 7(SEQ ID NO: 19 and 2) | 301L, 309R, 312E, 321E | [GAQP]2 | desB30 | C20d-gGlu-2xOEG |
| 8(SEQ ID NO: 30 and 2) | 301L, 309R, 312E, 321E | [GQAP]2 | desB30 | C18d-gGlu-2xOEG |
| 9(SEQ ID NO: 20 and 2) | 301L, 309R, 312E, 321E | [GAQP]3 | desB30 | C18d-gGlu-2xOEG |
| 10(SEQ ID NO: 20 and 29) | 301L, 309R, 312E, 321E | [GAQP]3 | A14E, desB30 | C18d-gGlu-2xOEG |
| 11(SEQ ID NO: 21 and 29) | 301L, 309R, 312E, 321E | [GAQP]4 | A14E, desB30 | C18d-gGlu-2xOEG |
| 12(SEQ ID NO: 21 and 2) | 301L, 309R, 312E, 321E | [GAQP]4 | desB30 | C18d-gGlu-2xOEG |
| 13(SEQ ID NO: 22 and 29) | 301L, 309R, 312E, 321E | [GAQP]6 | A14E, desB30 | C18d-gGlu-2xOEG |
| 14(SEQ ID NO: 22 and 2) | 301L, 309R, 312E, 321E | [GAQP]6 | desB30 | C18d-gGlu-2xOEG |
| 15(SEQ ID NO: 22 and 29) | 301L, 309R, 312E, 321E | [GAQP]6 | A14E, desB30 | C18d-gGlu-OEG |
| 16(SEQ ID NO: 22 and 29) | 301L, 309R, 312E, 321E | [GAQP]6 | A14E, desB30 | C20d-gGlu-2xOEG |
| 17(SEQ ID NO: 23 and 2) | 301L, 309R, 312E, 321E | [GAQP]8 | desB30 | C18d-gGlu-2xOEG |
| 18(SEQ ID NO: 24 and 2) | 301L, 309R, 312E, 321E | [GAQP]12 | desB30 | C18d-gGlu-2xOEG |
| 19(SEQ ID NO: 27 and 2) | 301L, 309R, 312E, 321E | [GAQP]19 | desB30 | C18d-gGlu-2xOEG |
| 20(SEQ ID NO: 27 and 29) | 301L, 309R, 312E, 321E | [GAQP]19 | A14E, desB30 | C18d-gGlu-2xOEG |
| 21(SEQ ID NO: 28 and 2) | 301L, 309R, 312E, 321E | [GAQP]19 | B3E, desB30 | C18d-gGlu-2xOEG |
| 22(SEQ ID NO: 27and 2) | 301L, 309R, 312E, 321E | [GAQP]19 | desB30 | C20d-gGlu-2xOEG |
| 23(SEQ ID NO: 27 and 29) | 301L, 309R, 312E, 321E | [GAQP]19 | A14E, desB30 | C20d-gGlu-2xOEG |
| 24(SEQ ID NO: 28 and 29) | 301L, 309R, 312E, 321E | [GAQP]19 | B3E, desB30 | C20d-gGlu-2xOEG |

In one embodiment, the invention relates to compounds selected from the group of fusion proteins of examples 1 to 24.

In one embodiment, the invention relates to compounds selected from the group of fusion proteins of example 1.

In one embodiment, the invention relates to compounds selected from the group of fusion proteins of examples independently selected from 2-5, 8-15 and 17-21.

In one embodiment, the invention relates to compounds selected from the group of fusion proteins of examples independently selected from 6, 7, 16, 22, 23 and 24. In one embodiment, the invention relates to compounds selected from the group of fusion proteins of examples independently selected from 1-4, 5-14 and 16-24.

In one embodiment the invention relates to fusion peptide of example 4: EGF(A)(301L, 309R, 312E, 321E)-[GAQP]2-Insulin(B29K(octadecanedioyl-gGlu-2×OEG), desB30) and represented by Chem.4.

In one embodiment the invention relates to fusion peptide of example 5: EGF(A)(301L, 309R, 312E, 321E)-[GAQP]2-Insulin(B3E, B29K(octadecanedioyl-gGlu-OEG), desB30) and represented by Chem.5.

In one embodiment the invention relates to fusion peptide of example 6: EGF(A)(301L, 309R, 312E, 321E)-[GAQP]2-Insulin(B3E, B29K(eicosanedioyl-gGlu-2×OEG), desB30) and represented by Chem.6.

In one embodiment the invention relates to fusion peptide of example 7: EGF(A)(301L, 309R, 312E, 321E)-[GAQP]2-Insulin(B29K(eicosanedioyl-gGlu-2×OEG), desB30) and represented by Chem.7.

In one embodiment the invention relates to fusion peptide of example 8: EGF(A)(301L, 309R, 312E, 321E)-[GQAP]2-Insulin(B29K(octadecanedioyl-gGlu-2×OEG), desB30) and represented by Chem.8.

In one embodiment the invention relates to fusion peptide of example 9: EGF(A)(301L, 309R, 312E, 321E)-[GAQP]3-Insulin(B29K(octadecanedioyl-gGlu-2×OEG), desB30) and represented by Chem.9.

In one embodiment the invention relates to fusion peptide of example 10: EGF(A)(301L, 309R, 312E, 321E)-[GAQP]3-Insulin(A14E, B29K(octadecanedioyl-gGlu-2×OEG), desB30) and represented by Chem.10.

In one embodiment the invention relates to fusion peptide of example 11: EGF(A)(301L, 309R, 312E, 321E)-[GAQP]4-Insulin(A14E, B29K(octadecanedioyl-gGlu-2×OEG), desB30) and represented by Chem.11.

In one embodiment the invention relates to fusion peptide of example 12: EGF(A)(301L, 309R, 312E, 321E)-[GAQP]4-Insulin(B29K(octadecanedioyl-gGlu-2×OEG), desB30) and represented by Chem.12.

In one embodiment the invention relates to fusion peptide of example 13: EGF(A)(301L, 309R, 312E, 321E)-[GAQP]6-Insulin(A14E, B29K(octadecanedioyl-gGlu-2×OEG), desB30) and represented by Chem.13.

In one embodiment the invention relates to fusion peptide of example 14: EGF(A)(301L, 309R, 312E, 321E)-[GAQP]6-Insulin(B29K(octadecanedioyl-gGlu-2×OEG), desB30) and represented by Chem.14.

In one embodiment the invention relates to fusion peptide of example 15: EGF(A)(301L, 309R, 312E, 321E)-[GAQP]6-Insulin(A14E, B29K(octadecanedioyl-gGlu-OEG), desB30) and represented by Chem.15.

In one embodiment the invention relates to fusion peptide of example 16: EGF(A)(301L, 309R, 312E, 321E)-[GAQP]6-Insulin(A14E, B29K(eicosanedioyl-gGlu-2×OEG), desB30 and represented by Chem.16.

In one embodiment the invention relates to fusion peptide of example 17: EGF(A)(301L, 309R, 312E, 321E)-[GAQP]8-Insulin(B29K(octadecanedioyl-gGlu-2×OEG), desB30 and represented by Chem.17.

In one embodiment the invention relates to fusion peptide of example 18: EGF(A)(301L, 309R, 312E, 321E)-[GAQP]2-Insulin(B29K(octadecanedioyl-gGlu-2×OEG), desB30) and represented by Chem.18.

In one embodiment the invention relates to fusion peptide of example 19: EGF(A)(301L, 309R, 312E, 321E)-[GAQP]19-Insulin(B29K(octadecanedioyl-gGlu-2×OEG), desB30) and represented by Chem.19.

In one embodiment the invention relates to fusion peptide of example 20: EGF(A)(301L, 309R, 312E, 321E)-[GAQP]19-Insulin(A14E, B29K(octadecanedioyl-gGlu-2×OEG), desB30) and represented by Chem.20.

In one embodiment the invention relates to fusion peptide of example 21: EGF(A)(301L, 309R, 312E, 321E)-[GAQP]19-Insulin(B3E, B29K(octadecanedioyl-gGlu-2×OEG), desB30) and represented by Chem.21.

In one embodiment the invention relates to fusion peptide of example 22: EGF(A)(301L, 309R, 312E, 321E)-[GAQP]19-Insulin(B29K(eicosanedioyl-gGlu-2×OEG), desB30) and represented by Chem.22.

In one embodiment the invention relates to fusion peptide of example 23: EGF(A)(301L, 309R, 312E, 321E)-[GAQP]19-Insulin(A14E, B29K(eicosanedioyl-gGlu-2×OEG), desB30) and represented by Chem.23.

In one embodiment the invention relates to fusion peptide of example 24: EGF(A)(301L, 309R, 312E, 321E)-[GAQP]19-Insulin(B3E, B29K(eicosanedioyl-gGlu-2×OEG), desB30) and represented by Chem.24.

Intermediate Products

The invention furthermore relates to an intermediate product in the form of a novel backbone, to which the substituents of the invention are attached, which leads to the fusion peptides of the invention.

The invention also relates to an intermediate product in the form of the novel backbone of the fusion peptides of the present invention, selected from the group consisting of:
 i. Backbone of examples 1, 3, 5 and 6 (SEQ ID NO: 17 and 2)
 ii. Backbone of example 2 (SEQ ID NO: 18 and 2)
 iii. Backbone of example 4 and 7 (SEQ ID NO: 19 and 2)
 iv. Backbone of example 8 (SEQ ID NO: 28 and 2)
 v. Backbone of example 9 (SEQ ID NO: 20 and 2)
 vi. Backbone of example 10 (SEQ ID NO: 20 and 27)
 vii. Backbone of example 11 (SEQ ID NO: 21 and 27)
 viii. Backbone of example 12 (SEQ ID NO: 21 and 2)
 ix. Backbone of example 13 15 and 16 (SEQ ID NO: 22 and 27)
 x. Backbone of example 14 (SEQ ID NO: 22 and 2)
 xi. Backbone of example 17 (SEQ ID NO: 23 and 2)
 xii. Backbone of example 18 (SEQ ID NO: 24 and 2)
 xiii. Backbone of example 19 and 22 (SEQ ID NO: 25 and 2)
 xiv. Backbone of example 20 and 23 (SEQ ID NO: 25 and 27)
 xv. Backbone of example 21 (SEQ ID NO: 26 and 2)
 xvi. Backbone of example 24 (SEQ ID NO: 26 and 2).

Bi-Functionality

Different functionalities are associated with the two analogues, the insulin analogue and the EGF(A) analogue. When combining the two analogues in fusion compound derivatives of the invention, it is preferred that the analogues remain functional i.e., that the insulin analogue has the ability to activate the insulin receptor and that the EGF(A) analogue binds to PCSK9. The functionalities of such compounds may be tested as described below.

Insulin Function

The relative binding affinity of insulin analogues for the human insulin receptor (IR) can be determined by competition binding in a scintillation proximity assay (SPA) as described in Example 25.

In one embodiment the fusion peptides of the invention have the ability to bind to the insulin receptor.

The lipogenesis assay described in Example 26 can be used as a measure of the functional (agonistic) activity of an insulin analogue.

In one embodiment the fusion peptides of the invention comprising an insulin analogue have the ability to bind to and activate the insulin receptor.

In one embodiment the fusion peptides of the invention have the ability to reduce blood glucose levels.

The fusion peptides of the present invention can be tested for pharmacokinetic parameters and/or insulin related pharmacodynamic properties as described in Examples 29 and 30.

The fusion peptides of the invention can be tested by subcutaneous administration to rats, e.g. comparing with comparator fusion compounds and/or similar B29K acylated insulin analogues according to this protocol.

In one embodiment, the fusion peptides of the present invention lower blood glucose levels.

In another embodiment, the fusion peptides of the present invention show comparable blood glucose reductions relative to similar B29K acylated insulin analogues.

The fusion peptides of the present invention comprise spacers with uncharged spacers (GQAP)n or (GAQP)n, with surprising superior blood glucose reduction relative to comparator compounds comprising charged spacers (GQEP)n.

Figure 2:
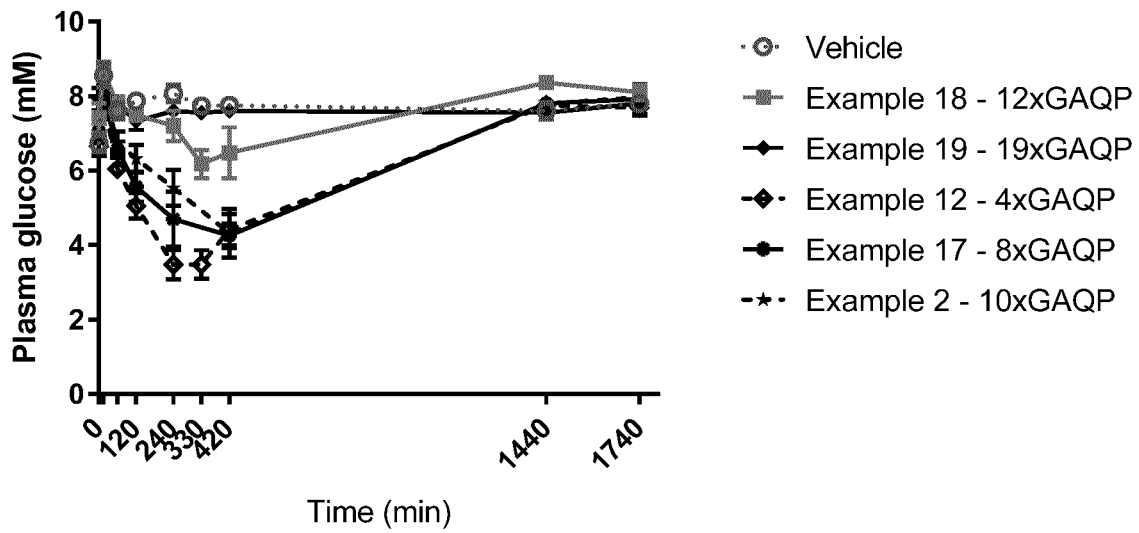
FIG. 2 shows the blood glucose lowering effects of the compounds of examples 2, 12, 17, 18, and 19 of the invention, all with the octadecanedioyl-gGlu-2×OEG side chain and with different lengths of GQAP/GAQP spacers.

It was found that the fusion peptides of the invention comprising a spacer (GQAP)n or (GAQP)n, wherein n=2-10 are equipotent with regards to glucose lowering effect, while the effect is not as pronounced for spacers wherein n is above 10 (FIGS. 1-2).

It was found that the fusion peptides of the invention comprising spacer (GQAP)n or (GAQP)n, wherein n=2-8, show superior blood glucose lowering effects than all the comparator compounds tested, comprising (GQEP)n, wherein n=2-8 (FIGS. 3-11).

Figure 13:
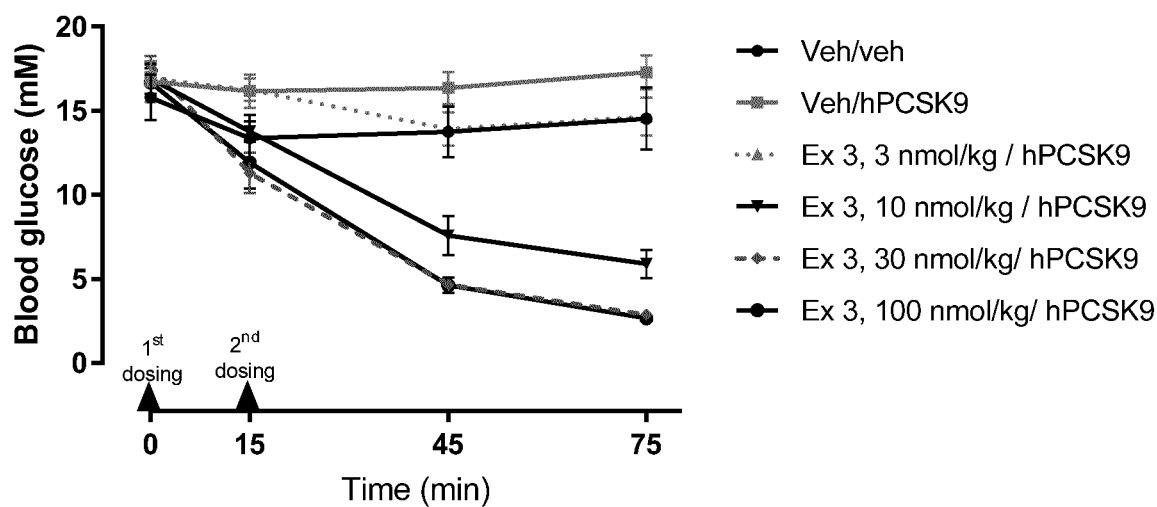
FIG. 13 shows dose-response of the compound of example 3 (0, 3, 10, 30 and 100 nmol/kg), i.v. dosed at t=0 min followed by i.v. dosing of vehicle or hPCSK9 at t=15 min. Blood glucose profiles following dosing of vehicle or compound of example 3 to diabetic mice.

It was found that the fusion peptides of the invention comprising spacer (GQAP)n or (GAQP)n, wherein n=2 show dose dependent blood glucose lowering (FIG. 13).

EGF(A) Function

EGF (A) peptide analogues have the ability to bind to PCSK9. Such binding may be assessed using the assay described in example 27 herein.

In one embodiment, the fusion proteins of the present invention are PCSK9 inhibitors.

In one embodiment, the fusion protein of the invention inhibits PCSK9 binding to human Low Density Lipoprotein Receptor (LDL-R).

In one embodiment, the invention provides a fusion protein comprising an EGF(A) peptide analogue of SEQ ID NO:1, wherein the fusion protein is capable of inhibiting PCSK9 binding to human Low Density Lipoprotein Receptor (LDL-R).

In one embodiment, the fusion proteins of the invention have the ability to inhibit PCSK9 binding to the LDL-R.

In one embodiment, the fusion proteins of the invention have the ability to inhibit PCSK9 binding to the LDL-R and reduce LDL levels in the blood.

In one embodiment, the fusion proteins of the invention reduce LDL blood levels.

In one embodiment, the fusion proteins of the present have an improved ability to bind to PCSK9 compared to native LDL-R(293-332) ((SEQ ID NO: 1, native EGF-(A)). In one embodiment, the fusion proteins of the present invention have comparable ability to bind to PCSK9 relative to LDL-R(293-332) EGF(A) analogue: (301Leu, 309Arg, 312Glu, 321Glu) (comparator fusion protein 9).

In one embodiment the $K_i$ of the fusion proteins of the invention as described herein as measured in the PCSK9-LDL-R binding competitive ELISA assay is below 20 nM, such as below 15 nM, or such as below 10 nM, or such as below 5 nM.

In another embodiment the $K_i$ of the fusion proteins of the invention as described herein as measured in the PCSK9-LDL-R binding competitive ELISA assay is below 5 nM.

Functionality of EGF-(A) analogue within the fusion proteins of the invention and derivatives hereof may be further characterized by their ability to improve LDL uptake, such as described in example 28 herein.

In one embodiment the fusion proteins of the invention increase LDL uptake in the presence of PCSK9.

In one embodiment the fusion proteins of the invention are capable of reversing or reducing PCSK9 mediated reduction of LDL uptake.

In one embodiment the fusion proteins of the invention have an EC50, as measured in the LDL uptake assay, below 1500 nM, such as below 1000 nM, such as below 500 nM or such as below 200 nM.

In one embodiment the fusion proteins of the invention have an EC50, as measured in the LDL uptake assay, below 1500 nM.

In one embodiment the fusion proteins of the invention have an EC50, as measured in the LDL uptake assay, below 500 nM.

In one embodiment the fusion proteins of the invention have an EC50, as measured in the LDL uptake assay, below 200 nM.

Figure 12:
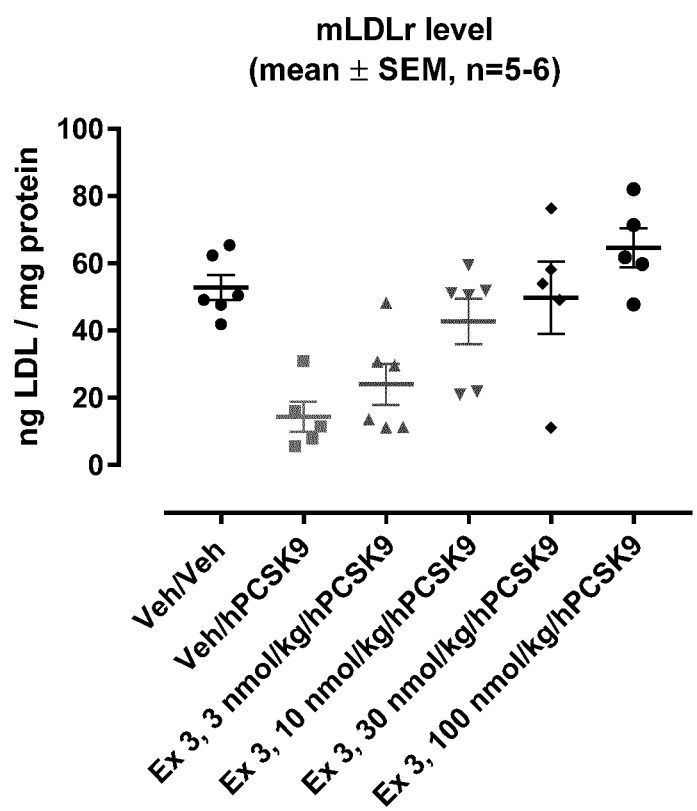
FIG. 12 shows dose-response of the compound of example 3 (0, 3, 10, 30 and 100 nmol/kg), i.v. dosed at t=0 min followed by i.v. dosing of vehicle or hPCSK9 at t=15 min. Liver LDL-r protein expression after dosing of vehicle or compound of example 3 followed by vehicle or hPCSK9 dosing to diabetic mice.
Figure 14:
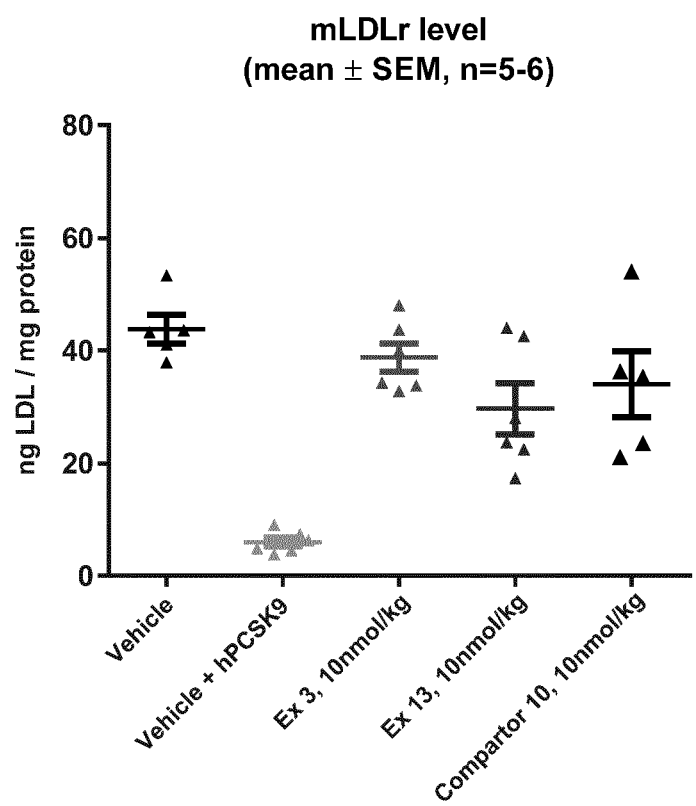
FIG. 14 shows dosing to diabetic mice of compounds of example 3 and 13 (0 and 10 nmol/kg), i.v. dosed at t=0 min followed by i.v. dosing of vehicle or hPCSK9 at t=15 min. Liver LDL-r protein expression after dosing of vehicle, compounds of example 3 and 13 or EGF(A) derivative (comparator compound 10) followed by hPCSK9 dosing to diabetic mice.

It was found that hPCSK9 administered to mice resulted in an almost complete down regulation of the hepatic LDL receptor protein (FIG. 12). The insulin-EGF(A) fusion protein effectively prevented this PCSK9-mediated down regulation of the LDLr protein in a dose-dependent way. Furthermore, it was shown that two insulin-EGF(A)fusion proteins were able to prevent the hPCSK9-mediated down regulation of LDLr protein similar to what was seen with the EGF(A) derivative alone (FIG. 14).

Bi-Functionality

In order to demonstrate bi-functionality or dual activity, selected compounds of the invention were tested in the in vivo model described in example 31. Dual-activity meaning an increase in the LDL receptor expression level in mouse liver by inhibiting the action of intravenously injected hPCSK9 with an insulin-EGF(A) based anti-PCSK9 peptide and glucose lowering effect by the insulin part of the molecule.

The selected compounds were found to lower blood glucose and prevent the hPCSK9-mediated down regulation of LDLr protein similar to what was seen with an EGF(A) derivative alone.

In one embodiment, the fusion protein of the present invention activates the insulin receptor.

In one embodiment, the fusion protein of the present invention lowers blood glucose.

In one embodiment, the fusion protein of the present invention showed superior blood glucose reduction compared to comparator fusion proteins.

In one embodiment, the fusion protein of the present invention showed improved blood glucose reduction compared to comparator fusion proteins.

In one embodiment, the fusion protein of the present invention binds to PCSK9.

In one embodiment, the fusion protein of the present invention inhibits PCKS9 binding to the LDL-R.

In one embodiment, the fusion protein of the present invention shows an improved ability to bind PCSK9 compared to wild type EGF(A).

In one embodiment, the fusion protein of the present invention has a Ki below 20 nM, when measured in the PCSK9-LDL-R binding competitive ELISA assay.

In one embodiment, the fusion protein of the present invention has a Ki below 5 nM, when measured in the PCSK9-LDL-R binding competitive ELISA assay.

In one embodiment, the fusion protein of the present invention increases LDL uptake.

In one embodiment, the fusion protein of the present invention has an EC50 below 1000 nM when measured in the LDL uptake assay.

In one embodiment, the fusion protein of the present invention has an EC50 below 500 nM when measured in the LDL uptake assay.

In one embodiment, the fusion protein of the present invention has an EC50 below 200 nM when measured in the LDL uptake assay.

As described above, the bi-functional fusion proteins of the present invention have been found, in in vitro assays, to bind to both the insulin receptor and PCSK9 resulting in activation of the insulin response and prevention of PCSK9 binding and thereby degradation of the LDLR. Furthermore, the inventors surprisingly found a combined effect on glucose lowering (insulin effect) and enhancement of hepatic LDLR expression (PCSK9i effect) in vivo.

Furthermore, it was surprisingly found that the fusion proteins of the present invention comprising an uncharged spacer show superior blood glucose reduction relative to comparator fusion proteins comprising charged spacers (GQEP)n and even further that the level of reduction is dependent on the length of said uncharged spacer.

Pharmaceutical Composition

The invention also relates to pharmaceutical compositions comprising a fusion protein of the invention, including e.g. an analogue of the invention, or a pharmaceutically acceptable salt, amide, or ester thereof, and one or more pharmaceutically acceptable excipient (s). Such compositions may be prepared as is known in the art.

The term "excipient" broadly refers to any component other than the active therapeutic ingredient(s). The excipient may be an inert substance, an inactive substance, and/or a not medicinally active substance. The excipient may serve various purposes, e.g. as a carrier, vehicle, diluent, tablet aid, and/or to improve administration, and/or absorption of the active substance. Non-limiting examples of excipients are: solvents, diluents, buffers, preservatives, tonicity regulating agents, chelating agents, and stabilisers. The formulation of pharmaceutically active ingredients with various excipients is known in the art, see e.g. Remington: The Science and Practice of Pharmacy (e.g. 21st edition (2005), and any later editions).

A composition of the invention may be in the form of a liquid formulation, i.e. aqueous formulation comprising water. A liquid formulation may be a solution, or a suspension. Alternatively, it may be a solid formulation, e.g. a freeze-dried or spray-dried composition.

A pharmaceutical composition of the invention may further comprise a second active ingredient, such as a therapeutic agent, which may simplify administration in case of combination treatments.

A composition of the invention may be for parenteral administration, e.g. performed by subcutaneous, intramuscular, intraperitoneal, or intravenous injection.

Pharmaceutical Indications

Diabetes

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by B-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

Other Indications

In one embodiment, a fusion protein according to the invention is used for the preparation of a medicament for the treatment or prevention of hyperglycemia including stress induced hyperglycemia, type 2 diabetes, impaired glucose tolerance, type 1 diabetes.

In another embodiment, a fusion protein according to the invention is used as a medicament for delaying or preventing disease progression in type 2 diabetes.

In one embodiment of the invention, the fusion protein is for use as a medicament for the treatment or prevention of hyperglycemia including stress induced hyperglycemia, type 2 diabetes, impaired glucose tolerance, type 1 diabetes.

In a further embodiment the invention is related to a method for the treatment or prevention of hyperglycemia including stress induced hyperglycemia, type 2 diabetes, impaired glucose tolerance, type 1 diabetes, the method comprising administering to a patient in need of such treatment an effective amount for such treatment of a fusion protein according to the invention.

In one embodiment, a fusion protein of the invention or a composition thereof may be used in a patient with diabetes for:

(i) improving lipid parameters, such as prevention and/or treatment of dyslipidemia, lowering total serum lipids; lowering LDL-C, increasing HDL; lowering small, dense LDL; lowering VLDL; lowering triglycerides; lowering cholesterol; lowering plasma levels of lipoprotein a (Lp(a)); In another embodiment, the present invention relates to a method for treatment in a patient with diabetes for:

i. improving lipid parameters, such as prevention and/or treatment of dyslipidemia, lowering total serum lipids; increasing HDL-C; lowering LDL-C, lowering small, dense LDL-C; lowering VLDL-C; lowering triglycerides; lowering cholesterol; lowering plasma levels of lipoprotein a (Lp(a)); wherein a pharmaceutically active amount of a fusion protein according to the invention, e.g. a peptide analogue or a derivative according to the invention, is administered to a patient with diabetes.

In one embodiment, the invention relates to the use of a fusion protein as described herein for use in the manufacture of a medicament.

The invention also relates to a fusion protein of the invention, or a pharmaceutical composition thereof for use as a medicament or in the manufacture of a medicament.

Mode of Administration

The term "treatment" is meant to include both the prevention and minimization of the referenced disease, disorder, or condition (i.e., "treatment" refers to both prophylactic and therapeutic administration of a fusion protein of the present invention or composition comprising a fusion protein of the present invention unless otherwise indicated or clearly contradicted by context.

The route of administration may be any route which effectively transports a fusion protein of this invention to the desired or appropriate place in the body, such as parenterally, for example, subcutaneously, intramuscularly or intravenously. Alternatively, a fusion protein of this invention can be administered orally, pulmonary, rectally, transdermally, buccally, sublingually, or nasally.

While certain features of the invention have been illustrated and described herein, many modifications, substitutions, changes, and equivalents will now occur to those of ordinary skill in the art. It is, therefore, to be understood that the appended embodiments are intended to cover all such modifications and changes as fall within the true spirit of the invention.

EMBODIMENTS

1. A fusion protein comprising an insulin peptide, an EGF (A) peptide, a spacer and a substituent, wherein, i. said insulin peptide is human insulin (SEQ ID NOs 2-3) or an analogue of human insulin
ii. said EGF(A) peptide is an analogue of the EGF(A) domain of LDL-R (293-332) (SEQ ID NO:1)
iii. said spacer is a peptide linker comprising segments of (GAQP)n or (GQAP)n, n=2-19, and connecting the N-terminal of the insulin analogue B-chain with the C-terminal of the EGF(A) analogue.
iv. said substituent is of formula (I): Acy-AA2$_m$-AA3$_p$-, wherein
Acy is a fatty diacid comprising from about 16 to about 20 carbon atoms,
AA2 is an acidic amino acid residue and wherein m is an integer in the range from 1 to 10 and
AA3 is a neutral, alkyleneglycol-containing amino acid residue and p is an integer in the range from 1 to 10, and
wherein the maximum number of AA2 and AA3 residues is 10 and
wherein the AA2 and AA3 residues may appear in any order,
or a pharmaceutically acceptable salt, amide, or ester thereof.

2. The fusion protein according to embodiment 1, wherein EGF(A) peptide analogue is fused to the N-terminal of the insulin analogue B-chain via the C-terminal amino acid residue of the EGF(A) analogue.
3. The fusion protein according to any of the previous embodiments, wherein the EGF(A) analogue comprises 1-15 amino acid mutation(s) compared to SEQ ID NO.:1.
4. The fusion protein according to any of the previous embodiments, wherein the EGF(A) analogue comprises 1-13 amino acid mutation(s) compared to SEQ ID NO.:1.
5. The fusion protein according to any of the previous embodiments, wherein the EGF(A) analogue comprises 1-11 amino acid mutation(s) compared to SEQ ID NO.:1.
6. The fusion protein according to any of the previous embodiments, wherein the EGF(A) analogue comprises 1-9 amino acid mutation(s) compared to SEQ ID NO.:1.
7. The fusion protein according to any of the previous embodiments, wherein the EGF(A) analogue comprises 1-7 amino acid mutation(s) compared to SEQ ID NO.:1.
8. The fusion protein according to any of the previous embodiments, wherein the EGF(A) analogue comprises 1-5 amino acid mutation(s) compared to SEQ ID NO.:1.
9. The fusion protein according to any of the previous embodiments, wherein the EGF(A) analogue comprises 1-3 amino acid mutation(s) compared to SEQ ID NO.:1.
10. The fusion protein according to any of the previous embodiments, wherein the EGF(A) analogue comprises one or two amino acid mutation(s) compared to SEQ ID NO.:1.
11. The fusion protein according to any of the previous embodiments, wherein the EGF(A) analogue comprises eight amino acid mutation(s) compared to SEQ ID NO.:1.
12. The fusion protein according to any of the previous embodiments, wherein the EGF(A) analogue comprises seven amino acid mutation(s) compared to SEQ ID NO.:1.
13. The fusion protein according to any of the previous embodiments, wherein the EGF(A) analogue comprises six amino acid mutation(s) compared to SEQ ID NO.:1.
14. The fusion protein according to any of the previous embodiments, wherein the EGF(A) analogue comprises five amino acid mutation(s) compared to SEQ ID NO.:1.
15. The fusion protein according to any of the previous embodiments, wherein the EGF(A) analogue comprises four amino acid mutation(s) compared to SEQ ID NO.:1.
16. The fusion protein according to any of the previous embodiments, wherein the EGF(A) analogue comprises three amino acid mutation(s) compared to SEQ ID NO.:1.
17. The fusion protein according to any of the previous embodiments, wherein the EGF(A) analogue comprises two amino acid mutation(s) compared to SEQ ID NO.:1.
18. The fusion protein according to any of the previous embodiments, wherein the EGF(A) analogue comprises 301L.
19. The fusion protein according to any of the previous embodiments, wherein the EGF(A) analogue comprises 309R.
20. The fusion protein according to any of the previous embodiments, wherein the EGF(A) analogue comprises 312E.
21. The fusion protein according to any of the previous embodiments, wherein the EGF(A) analogue comprises 321E.
22. The fusion protein according to any of the previous embodiments, wherein the EGF(A) analogue comprises one of the following combinations below:
a. 301Leu and 309Arg
b. 301Leu, 309Arg and 312Glu
c. 301Leu, 309Arg, 312Glu and 321Glu
23. The fusion protein according to embodiment 22, wherein the EGF(A) analogue comprises 301L and 309R.
24. The fusion protein according to embodiment 22, wherein the EGF(A) analogue comprises 301L, 309R and 312E.
25. The fusion protein according to embodiment 22, wherein the EGF(A) analogue comprises 301L, 309R, 312E and 321E.
26. The fusion protein according to embodiment 22, wherein the EGF(A) analogue is 301L, 309R, 312E, 321E.
27. The fusion protein according to any of the previous embodiments, wherein the insulin analogue/derivative is an analogue/derivative of human insulin comprising 0-10 mutations.
28. The fusion protein according to embodiment 27, wherein the insulin comprises 1-10 mutations.
29. The fusion protein according to embodiment 28, wherein the insulin comprises 1-8 mutations.
30. The fusion protein according to embodiment 28, wherein the insulin comprises 1-6 mutations.
31. The fusion protein according to embodiment 28, wherein the insulin comprises five mutations.
32. The fusion protein according to embodiment 28, wherein the insulin comprises 1~4 mutations.
33. The fusion protein according to embodiment 28, wherein the insulin comprises four mutations.
34. The fusion protein according to embodiment 28, wherein the insulin comprises 1-3 mutations.
35. The fusion protein according to embodiment 28, wherein the insulin comprises one or two mutations.
36. The fusion protein according to embodiment 28, wherein the insulin comprises one mutation.
37. The fusion protein according to any of the previous embodiments, wherein the insulin analogue comprises one of the following combinations below:
a. A14E
b. B3E
c. desB30
d. A14E, desB30
e. B3E, desB30
38. The fusion protein according to embodiment 37, wherein said the insulin analogue comprises desB30.
39. The fusion protein according to embodiment 37, wherein said the insulin analogue comprises B3E.

40. The fusion protein according to embodiment 37, wherein said the insulin analogue comprises A14E, desB30.
41. The fusion protein according to embodiment 37, wherein said the insulin analogue comprises B3E, desB30.
42. The fusion protein according to embodiment 37, wherein said the insulin analogue is A14E, desB30.
43. The fusion protein according to embodiment 37, wherein said the insulin analogue is B3E, desB30.
44. The fusion protein according to embodiment 37, wherein said insulin analogue is insulin desB30 human insulin.
45. The fusion protein according to any of the previous embodiments, wherein the fusion protein activates the insulin receptor and binds to PCSK9.
46. The fusion protein according to any one of the previous embodiments, wherein said fusion protein comprises a spacer connecting the EGF(A) analogue and the insulin analogue/derivative.
47. The fusion protein according to any one of the previous embodiments, wherein the spacer comprises amide bonds.
48. The fusion protein according to any one of the previous embodiments, wherein the spacer comprises 4-80 amino acid residues.
49. The fusion protein according to any one of the previous embodiments, wherein the spacer comprises one or more of the following amino acid residues: Ala(A), Gly(G), Pro(P) and/or Gln(Q).
50. The fusion protein according to any one of the previous embodiments, wherein the spacer comprises (GAQP)n or (GQAP)n, wherein n=1-20.
51. The fusion protein according to embodiment 50, wherein the spacer comprises (GAQP)n or (GQAP)n, wherein n=2-19.
52. The fusion protein according to embodiment 50, wherein the spacer comprises (GAQP)n or (GQAP)n, wherein n=2-12.
53. The fusion protein according to embodiment 50, wherein the spacer comprises (GAQP)n or (GQAP)n, wherein n=2-10.
54. The fusion protein according to embodiment 50, wherein the spacer comprises (GAQP)n or (GQAP)n, wherein n=2-8.
55. The fusion protein according to embodiment 50, wherein the spacer comprises (GAQP)n or (GQAP)n, wherein n=2-6.
56. The fusion protein according to embodiment 50, wherein the spacer comprises (GAQP)n or (GQAP)n, wherein n=2-4.
57. The fusion protein according to embodiment 50, wherein the spacer comprises (GAQP)n or (GQAP)n, wherein n=2.
58. The fusion protein according to embodiment 50, wherein the spacer comprises (GAQP)n or (GQAP)n, wherein n=3.
59. The fusion protein according to embodiment 50, wherein the spacer comprises (GAQP)n or (GQAP)n, wherein n=4.
60. The fusion protein according to embodiment 50, wherein the spacer comprises (GAQP)n or (GQAP)n, wherein n=5.
61. The fusion protein according to embodiment 50, wherein the spacer comprises (GAQP)n or (GQAP)n, wherein n=6.
62. The fusion protein according to embodiment 50, wherein the spacer comprises (GAQP)n or (GQAP)n, wherein n=7.
63. The fusion protein according to embodiment 50, wherein the spacer comprises (GAQP)n or (GQAP)n, wherein n=8.
64. The fusion protein according to embodiment 50, wherein the spacer comprises (GAQP)n or (GQAP)n, wherein n=10.
65. The fusion protein according to embodiment 50, wherein the spacer comprises (GAQP)n or (GQAP)n, wherein n=12.
66. The fusion protein according to embodiment 50, wherein the spacer comprises (GAQP)n or (GQAP)n, wherein n=14.
67. The fusion protein according to embodiment 50, wherein the spacer comprises (GAQP)n or (GQAP)n, wherein n=16.
68. The fusion protein according to embodiment 50, wherein the spacer comprises (GAQP)n or (GQAP)n, wherein n=18.
69. The fusion protein according to embodiment 50, wherein the spacer comprises (GAQP)n or (GQAP)n, wherein n=19.
70. The fusion protein according to embodiment 50, wherein the spacer comprises (GAQP)n or (GQAP)n, wherein n=20.
71. The fusion protein according to any of the previous embodiments, wherein said fusion protein comprises one substituent.
72. The fusion protein according to any one of the preceding embodiments, wherein said the substituent is attached via a Lys/K amino acid residue.
73. The fusion protein according to any one of the preceding embodiments, wherein said the substituent is attached to the Lys/K amino acid residue B29K within the insulin sequence of said fusion protein.
74. The fusion protein according to any one of the preceding embodiments, wherein the order by which AA2 and AA3 appears in the formula can be interchanged independently.
75. The fusion protein according to any one of the preceding embodiments, wherein the Acy of formula (I): Acy-AA2$_m$-AA3$_p$-, comprises a fatty diacid group selected from: 1,16-hexadecanedioic acid, 1,18-octadecanedioic acid and 1,20-eicosanedioic acid.
76. The fusion protein according to embodiment 75, wherein the Acy comprises a fatty diacid group 1,16-hexadecanedioic acid.
77. The fusion protein according to embodiment 75, wherein the Acy comprises a fatty diacid group 1,18-octadecanedioic acid.
78. The fusion protein according to embodiment 75, wherein the Acy comprises a fatty diacid group 1,20-eicosanedioic acid.
79. The fusion protein according to any one of the preceding embodiments, wherein said AA2$_m$ of formula (I): Acy-AA2$_m$-AA3$_p$-, comprises gGlu, which represents a gamma glutamic acid residue represented by the following structure:

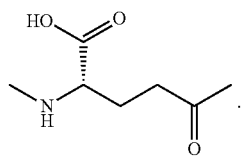

80. The fusion protein according to any one of the preceding embodiments, wherein said $AA3_p$ of formula (I): Acy-$AA2_m$-$AA3_p$-, comprises 1×OEG or [2-(2-aminoethoxy)ethoxy]acetyl or amino acid residue 8-amino-3,6-dioxaoctanoic acid —$NH(CH_2)_2O(CH_2)_2OCH_2CO$— and is represented by the following structure:

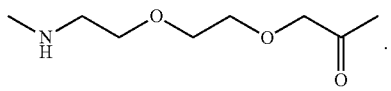

81. The fusion protein according to any one of the preceding embodiments, wherein said AA3p of formula (I): Acy-$AA2_m$-$AA3_p$-, comprises 2×OEG.

82. The fusion protein according to any one of the preceding embodiments, wherein $AA2_m$-$AA3_p$- of formula (I): Acy-$AA2_m$-$AA3_p$-, is represented independently by gGlu-OEG or gGlu-OEG-OEG.

83. The fusion protein according to embodiment 82, wherein $AA2_m$-$AA3_p$- of formula (I): Acy-$AA2_m$-$AA3_p$-, is represented by gGlu-OEG.

84. The fusion protein according to embodiment 82, wherein $AA2_m$-$AA3_p$- of formula (I): Acy-$AA2_m$-$AA3_p$-, is represented by gGlu-OEG-OEG.

85. The fusion protein according to any one of the preceding embodiments, wherein said substituent Acy-$AA2_m$-$AA3_p$- is represented by the following:

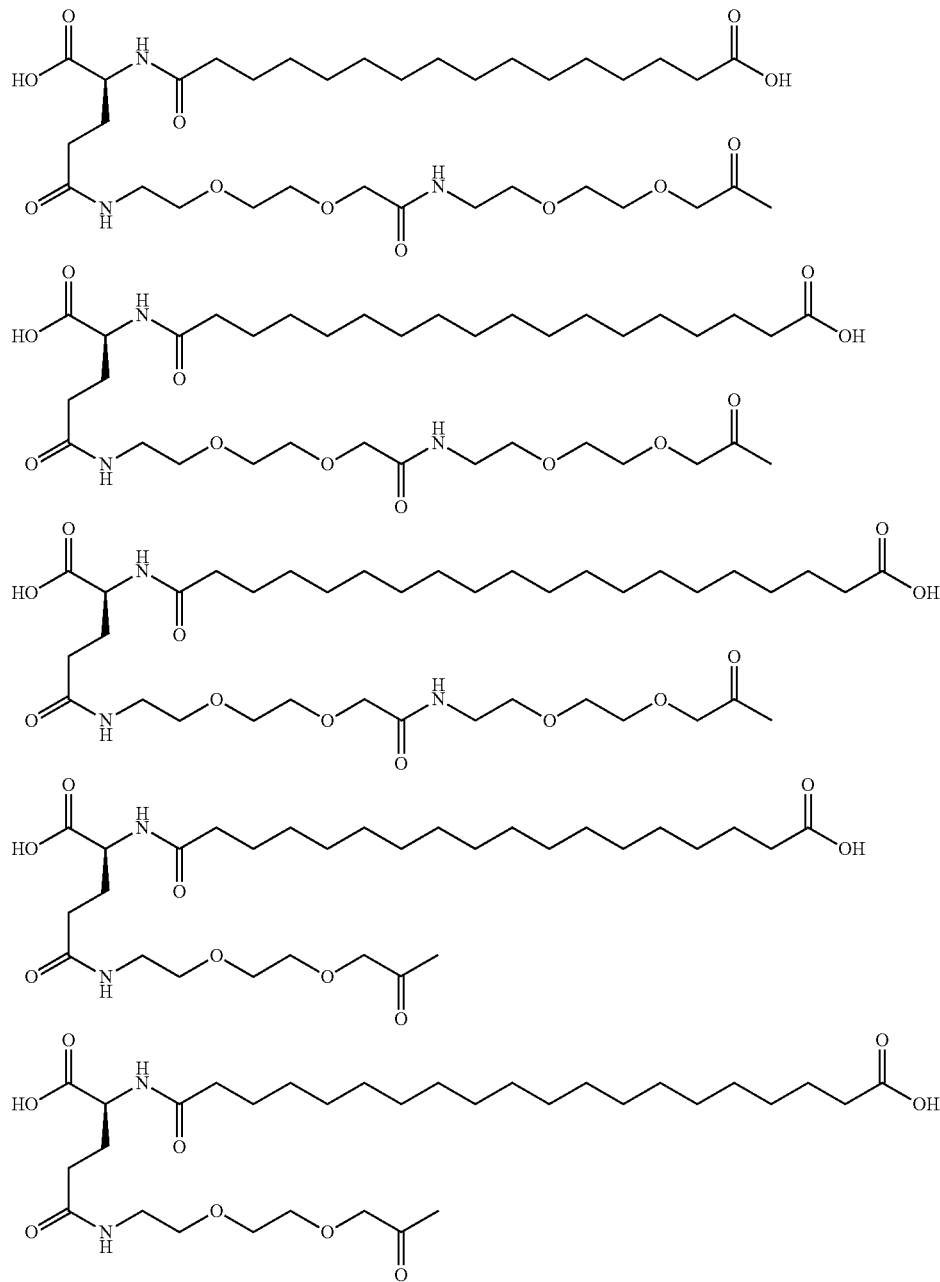

86. The fusion protein according to embodiment 85, wherein said substituent Acy-AA2$_m$-AA3$_p$- is selected from the following:

[Chemical structure diagrams]

87. The fusion protein according to any one of the preceding embodiments, wherein said substituent Acy-AA2$_m$-AA3$_p$- is represented independently by:
  i. C16 diacid-gGlu-2×OEG
  ii. C18 diacid-gGlu-OEG
  iii. C18 diacid-gGlu-2×OEG
  iv. C20 diacid-gGlu-2×OEG
88. The fusion protein according to embodiment 87, wherein said substituent Acy-AA2$_m$-AA3$_p$- is represented independently by C16 diacid-gGlu-2×OEG.
89. The fusion protein according to embodiment 87, wherein said substituent Acy-AA2$_m$-AA3$_p$- is represented independently by C18 diacid-gGlu-OEG.
90. The fusion protein according to embodiment 87, wherein said substituent Acy-AA2$_m$-AA3$_p$- is represented independently by C18 diacid-gGlu-2×OEG.
91. The fusion protein according to embodiment 87, wherein said substituent Acy-AA2$_m$-AA3$_p$- is represented independently by C20 diacid-gGlu-2×OEG.
92. The fusion protein according to any of the previous embodiments, wherein the fusion protein activates the insulin receptor.
93. The fusion protein according to any of the previous embodiments, wherein the fusion protein has the ability to lower blood glucose.
94. The fusion protein according to any of the previous embodiments, wherein the fusion protein showed superior blood glucose reduction compared to comparator fusion proteins.
95. The fusion protein according to any of the previous embodiments, wherein the fusion protein showed improved blood glucose reduction compared to comparator fusion proteins.
96. The fusion protein according to any of the previous embodiments, wherein the fusion protein binds to PCSK9.
97. The fusion protein according to any of the previous embodiments, wherein the fusion protein inhibits PCKS9 binding to the LDL-R.
98. The fusion protein according to any of the previous embodiments, wherein the fusion protein has an improved ability to bind PCSK9 compared to wild type EGF(A).
99. The fusion protein according to any of the previous embodiments, wherein the Ki of the fusion protein, when measured in the PCSK9-LDL-R binding competitive ELISA assay is below 20 nM.
100. The fusion protein according to any of the previous embodiments, wherein the Ki of the fusion protein, when measured in the PCSK9-LDL-R binding competitive ELISA assay is below 5 nM.
101. The fusion protein according to any of the previous embodiments, wherein the fusion protein increases LDL uptake.
102. The fusion protein according to any of the previous embodiments, wherein the fusion protein has an EC50 below 1000 nM when measured in the LDL uptake assay.
103. The fusion protein according to any of the previous embodiments, wherein the fusion protein has an EC50 below 500 nM when measured in the LDL uptake assay.
104. The fusion protein according to any of the previous embodiments, wherein the fusion protein has an EC50 below 200 nM when measured in the LDL uptake assay.
105. The fusion protein according to any of the previous embodiments, wherein said fusion protein is represented by fusion proteins of examples 1-24.
106. The fusion protein according to any of the previous embodiments, wherein said fusion protein is represented by fusion proteins of example 1.
107. The fusion protein according to any of the previous embodiments, wherein said fusion protein is represented by fusion proteins of examples 1-24.
108. The fusion protein according to any of the previous embodiments, wherein said fusion protein is represented by fusion proteins of examples 2-5, 8-15 and 17-21.
109. The fusion protein according to any of the previous embodiments, wherein said fusion protein is represented by fusion proteins of examples 6, 7, 16, 22, 23 and 24.
110. The fusion protein according to any of the previous embodiments, wherein said fusion protein is represented by fusion proteins of examples 1-4, 5-14 and 16-24.
111. The fusion protein according to any of the previous embodiments, wherein said fusion protein is represented by fusion proteins of examples 1-18.

112. The fusion protein according to any of the previous embodiments, wherein said fusion protein is represented by fusion proteins of examples 1 and 3-17.
113. The fusion protein according to any of the previous embodiments, wherein said fusion protein is represented by fusion proteins of examples 1 and 3-16.
114. The fusion protein according to any of the previous embodiments, wherein said fusion protein is represented by fusion proteins of examples 1 and 3-12.
115. The fusion protein according to any of the previous embodiments, wherein said fusion protein is represented by fusion proteins of examples 1 and 3-8.
116. The fusion protein according to any of the previous embodiments, for use as a medicament.
117. The fusion protein according to any of the previous embodiments, for use in the prevention or treatment of a cardiovascular disease in diabetic patients.
118. The fusion protein according to any of the previous embodiments, for use in a method for improving lipid parameters in patients with diabetes.
119. An intermediate product in the form of the novel backbone of the fusion proteins of the invention, selected from the group consisting of:
   i. Backbone of examples 1, 3, 5 and 6 (SEQ ID NO: 17 and 2)
   ii. Backbone of example 2 (SEQ ID NO: 18 and 2)
   iii. Backbone of example 4 and 7 (SEQ ID NO: 19 and 2)
   iv. Backbone of example 8 (SEQ ID NO: 28 and 2)
   v. Backbone of example 9 (SEQ ID NO: 20 and 2)
   vi. Backbone of example 10 (SEQ ID NO: 20 and 27)
   vii. Backbone of example 11 (SEQ ID NO: 21 and 27)
   viii. Backbone of example 12 (SEQ ID NO: 21 and 2)
   ix. Backbone of example 13 15 and 16 (SEQ ID NO: 22 and 27)
   x. Backbone of example 14 (SEQ ID NO: 22 and 2)
   xi. Backbone of example 17 (SEQ ID NO: 23 and 2)
   xii. Backbone of example 18 (SEQ ID NO: 24 and 2)
   xiii. Backbone of example 19 and 22 (SEQ ID NO: 25 and 2)
   xiv. Backbone of example 20 and 23 (SEQ ID NO: 25 and 27)
   xv. Backbone of example 21 (SEQ ID NO: 26 and 2)
   xvi. Backbone of example 24 (SEQ ID NO: 26 and 2).
120. The fusion protein according to any of embodiments 1-115, for use in the treatment or prevention of diabetes, diabetes of Type 1, diabetes of Type 2, impaired glucose tolerance, hyperglycemia and/or dyslipidemia.
121. The fusion protein according to any of embodiments 1-115, for use in a method of treatment in a patient with diabetes for improving lipid parameters in a, such as prevention and/or treatment of dyslipidemia, lowering total serum lipids, increasing HDL-C, lowering LDL-C, lowering small, dense LDL-C, lowering VLDL-C, lowering triglycerides, lowering cholesterol, lowering plasma levels of lipoprotein a (Lp(a)) or inhibiting generation of apolipoprotein A (apo(A)).
122. A pharmaceutical composition comprising a fusion protein according to any of embodiments 1-118, and a pharmaceutically acceptable excipient.
123. The pharmaceutical composition according to embodiment 122, for subcutaneous administration.
124. A pharmaceutical composition for the treatment of diabetes in a patient in need of such treatment, comprising a therapeutically effective amount of a fusion protein according to any one of embodiments 1-118, together with a pharmaceutically acceptable carrier.
125. The pharmaceutical composition of embodiment 122, for use as a medicament.
126. The pharmaceutical composition of embodiment 122, for use in the treatment of patients with diabetes and high risk of cardiovascular disease.
127. Use of a fusion protein according to any one of embodiments 1-118, for the manufacture of a medicament for the treatment or prevention of diabetes, diabetes of Type 1, diabetes of Type 2, impaired glucose tolerance, hyperglycemia, dyslipidemia.
128. A method for improving lipid parameters comprising a step of administering a pharmaceutically active amount of a fusion protein according to any of the previous embodiments 1-115, in a patient with diabetes.
129. A method for improving lipid parameters a patient with diabetes comprising a step of administering a pharmaceutically active amount of a fusion protein according to any of the previous embodiments 1-118, such as prevention and/or treatment of dyslipidemia, lowering total serum lipids; increasing HDL; lowering LDL-C; lowering small, dense LDL-C; lowering VLDL-C; non_HDL-C; lowering triglycerides; lowering cholesterol; lowering plasma levels of lipoprotein a (Lp(a)).
130. An insulin analogue according to any of the previous embodiments 1-118, for use in a method of treatment in a patient with diabetes for: improving lipid parameters, such as prevention and/or treatment of dyslipidemia, lowering total serum lipids, increasing HDL-C, lowering LDL-C, lowering small, dense LDL-C, lowering VLDL-C, lowering triglycerides, lowering cholesterol, lowering plasma levels of lipoprotein a (Lp(a)) or inhibiting generation of apolipoprotein A (apo(A)); and prevention and/or treatment of cardiovascular diseases.
131. A method for prevention and/or treatment of a cardiovascular disease in diabetes patients, comprising a step of administering a pharmaceutically active amount of a fusion protein according to any of the previous embodiments 1-118.
132. A method for the treatment or prevention of diabetes, diabetes of Type 1, diabetes of Type 2, impaired glucose tolerance, hyperglycemia, dyslipidemia, which method comprises administration to a subject in need thereof a therapeutically effective amount of a fusion protein according to any one of embodiments 1-118.

EXAMPLES

List of Abbreviations

AcOH: acetic acid
ADO: 8-amino-3,6-dioxaoctanoic acid
ALP Achromobactor lyticus protease
API: Active Pharmaceutical Ingredient
AUC area under the curve;
AUC/D dose-normalised area under the curve;
BG: Blood Glucose
BHK: baby hamster kidney
Boc: t-butyloxycarbonyl
$C_{max}$ maximal plasma concentration;
$C_{max}$/D dose-normalised maximal plasma concentration;
C-peptide connecting peptide
Clt: 2-chlorotrityl
collidine: 2,4,6-trimethylpyridine
D dose;
DCM: dichloromethane
DIC: diisopropylcarbodiimide
DIPEA=DIEA N,N-disopropylethylamine DMAP: 4-dimethylaminopyridine
DMF: N,N-dmethylformamide
DMSO: dimethylsulfoxide
DTT: DL-dithiothreitol
EC50: Half maximal effective concentration
EDC: N-(3-Dimethylaminopropyl)-N'-ethylcarbodiimide
EDTA: Ethylenediaminetetraacetic acid
EGF: Epidermal growth factor-like
EGF(A): Epidermal growth factor-like domain A
eps: epsilon
F bioavailability (fraction absorbed);
Fmoc: 9-fluorenylmethyloxycarbonyl
γGlu (gGlu) gamma L-glutamyl;
HCl hydrochloric acid
HDL: High density lipoprotein
HEPES: 4-(2-hydroxyethyl)-1-piperazineethanesulfonic acid
HFIP 1,1,1,3,3,3-hexafluoro-2-propanol or hexafluoroisopropanol
HI: human insulin
hLDL-R: human LDL receptor
hPCSK9: human PCSK9
HPLC: High Performance Liquid Chromatography
HSA: Human Serum Albumin
$IC_{50}$: half maximum inhibitory concentration
IGF-1R insulin-like growth factor 1 receptor
IP: intra peritoneal
IR: Insulin receptor
i.v. intravenously
LC liquid chromatography
LCMS or LC-MS: Liquid Chromatography Mass Spectroscopy
LDL-R or LDLr: LDL receptor
LDL: low density lipoprotein
LDL-C: LDL cholesterol
MALDI-TOF matrix-assisted laser desorption ionisation time-of-flight
MeCN: acetonitrile
MeOH: methanol
MRT mean residence time;
MS mass spectrometry
Mtt: 4-methyltrityl
NMP: N-methyl pyrrolidone
OEG [2-(2-aminoethoxy)ethoxy]ethylcarbonyl;
OSu: O-succinimidyl esters (hydroxysuccinimide esters)
OtBu: tert butyl ester
Oxyma Puree: Cyano-hydroxyimino-acetic acid ethyl ester
% extrap percentage of extrapolated profile.
Pbf: 2,2,4,6,7-pentamethyldihydrobenzofuran-5-sulfonyl
PBS: Phosphate Buffered Saline
PD pharmacodynamics (e.g. blood/plasma glucose lowering effect)
PK pharmacodynamics (blood/plasma insulin concentrations versus time profiles)
Pra: L-Propargylglycine
rhLDL-R: recombinant human LDL receptor
RP: Reverse Phase
RP-HPLC: Reverse Phase High Performance Liquid Chromatography
RT: Room Temperature
s.c.: Subcutaneously
SD: Standard Deviation
SEM: Standard Error of Mean
SPA: scintillations proximity assay
SPPS: Solid Phase Peptide Synthesis
T ½ terminal halflife;
tBu: tert-butyl
$T_{max}$ time to maximal plasma exposure;
TCTU: O-(6-Chlorobenzotriazol-1-yl)-N,N,N',N'-tetramethyluronium tetrafluoroborate
TFA: trifluoroacetic acid
THPTA: tris-hydroxypropyltriazolylmethylamine
TIS or TIPS: triisopropylsilane
TRIS: tris(hydroxymethyl)aminomethane or 2-amino-2-hydroxymethyl-propane-1,3-diol
TBS-T: Tris buffered saline
Trt: triphenylmethyl (trityl)
TSTU O—(N-succinimidyl)-1,1,3,3-tetramethyluronium tetrafluoroborate
UPLC: Ultra Performance Liquid Chromatography
wt. wild type The invention is further illustrated with reference to the following examples, which are not intended to be in any way limiting to the scope of the invention as claimed.

The analogues, i.e the two-chain non-acylated insulin EGF(A) fusion proteins can either be expressed in e-coli or in yeast as further described below.

Recombinant Expression of EGF(A) Insulin Fusion Compound Analogues in E. coli and Purification EGF(A) Insulin fusion protein analogues can be well expressed in E. coli as inclusion bodies (IB).

The cDNA of Insulin-EGF(A) fusion protein analogues was sub-cloned into a pET11b derived vector, and then the plasmids were transformed into a BL21 (DE3) derived host strain. Fermentation was carried out on fed-batch process in chemical defined medium.

The insulin-EGF(A) fusion protein analogues were further purified as below:

Cells were harvested and lysed in 20 mM pH8.0 Tris buffer with 150 mM NaCl using cell disruptor. The insoluble fraction, containing the IBs of the fusion protein, was collected and washed by 20 mM pH 8.0 Tris buffer with 500 mM NaCl and $H_2O$ sequentially. Then, 20 mM Tris, 6 M urea, 10 mM DTT, pH 9.0 was used to solubilize the IBs to a concentration of 10 mg/mL at room temperature (20-25° C.). After solubilization, the solution was diluted 10 times by 20 mM glycine, 1 mM cysteine, 10 mM CaCl2), pH 10.5 for refolding, which would be completed in 6-10 hours at room temperature. Following the clarification (centrifugation or depth-filtration), Q Sepharose Big-beads (20 mM Tris, 10 mM $CaCl_2$, 10% EtOH, pH 8.0) was used to capture the protein. Thereafter, the elution pool was treated by ALP at the ratio of 1:1000 for 3-4 hours at room temperature. The cleaved protein was then applied to the Source 30RPC for separation. As a final polishing step, Source 30Q (20 mM Tris, 10 mM $CaCl_2$, 10% EtOH, pH 8.0) using a shallow NaCl gradient was employed. For the analogues with longer spacer (i.e. repeats>=6), pH 8.5 should be used to facilitate binding at both anion exchange steps.

Recombinant Expression of EGF(A) Insulin Fusion Compounds in Yeast and Purification The EGF(A) insulin fusion analogues are expressed and cultivated by wellknown techniques e.g. as disclosed in WO2017/032798. More specifically, the insulin-EGF(A) fusion proteins are prepared and purified as follows:

Capture of the Precursor on SP Sepharose BB:

The yeast supernatant was loaded with a flow of 10-20 cv/h onto a column packed with SP Sepharose BB. A wash with 0.1 M citric acid pH 3.5 and a wash with 40% EtOH were performed. The analogue was eluted with 0.2 M Na-Acetate pH 5.5/35% EtOH.

Reshuffling of Disulphide Bridges:

The SP-pool was adjusted to pH 9. Reshuffling reagents were added to final concentration; cysteine 2.5 mM, cystine 0.25 mM and $CaCl_2$) 25 mM and followed on UPLC.

ALP Digestion:

Reshuffling pool was adjusted to pH 9 and ALP enzyme was added 1:100 (w/w). Reaction followed on UPLC. ALP cleavage pool was adjusted to pH 2.5 and diluted 2× in order to be prepared for RPHPLC purification.

RPHPLC Purification:

Purification was performed by RPHPLC C18 as below:
Column: 15 um C18 50×250 mm 200 Å

Buffers:
A: 25 mM $CaCl_2$, 0.2% Formic acid, 5% EtOH,
B: 0.2% Formic acid, 50% EtOH
The gradient:20-55% B-buffer.
Gradient: 20 CV
Flow 20 CV/h
Load g ~5 g/l resin
Fractions were analysed by UPLC, pooled and freeze dried.

General Remarks

The following examples and general procedures refer to final products identified in the specification and in the synthesis schemes. The preparation of the compounds of the present invention is described in detail using the following examples, but the chemical reactions described are disclosed in terms of their general applicability to the preparation of compounds of the invention.

Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, i.e. by appropriate protection of interfering groups, by changing to other conventional reagents, or by routine modification of reaction conditions.

Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

Analytical Methods:
LC-MS Method 1 (electrospray):
System: Waters Acquity UPLC SQD 2000
Column: Acquity UPLC BEH 1.7μ C18 100 Å 2.1×50 mm
  Detector:UV: PDA, SQD 2000
  Ionisation method: ES+
  Scanning range: 500-2000
  Cone Voltage: 60 V
  Scantime 0.5
  Linear gradient: 10% to 90% B
  Gradient run-time: 3 min
  Total run-time: 4 min
  Flow rate: 0.3 ml/min
  Column temperature: 40° C.
  PDA: 210-400 nm
  Solvent A: 99.90% H2O, 0.1% TFA
  Solvent B: 99.90% CH3CN, 0.1% TFA
  Solvent C: NA
LC-MS Method 2 (Electrospray):
System: Waters Acquity UPLC H-Class SQD2 2000
Column: Acquity UPLC BEH 1.7 C18 100 2.1×50 mm. Part no:186002350
  Detector:UV: PDA, SQD 2000
  Ionisation method: ES+
  Scanning range: 500-2000
  Cone Voltage: 60 V
  Scantime 0.5
  Linear gradient: 10% to 80% B
  Gradient run-time: 2.50 min
  Total run-time: 4 min
  Flow rate: 0.3 ml/min (0-2.51 min) and 0.8 ml/min (2.51-4.00 min)
  Column temperature: 40 C
  PDA: 210-400 nm
  Solvent A: 99.90% H2O, 0.1% TFA
  Solvent B: 99.90% CH3CN, 0.1% TFA
  Solvent C: NA
LC-MS Method 3 (TOF):
System:Agilent 1290 infinity series UPLC
Column: Eclipse C18+2.1×50 mm 1.8 u
Detector: Agilent Technologies LC/MSD TOF 6230 (G6230A)
  Ionisation method: Agilent Jet Stream source
  Scanning range: m/z min. 100, m/z max. 3200
  linear reflector mode
  positive mode
  Linear gradient: 5% to 95% B
  Gradient run-time: 6 minutes 0-4.5 min 5-95% B, 4.5-5 95% B, 5-5.5 95-5% B 5.5-6 5% B
  Flow rate: 0.40 ml/min fixed
  Column temperature: 40° C.
  Solvent A: 99.90% H2O, 0.02% TFA
  Solvent B: 99.90% CH3CN, 0.02% TFA
  Solvent C: NA
  Calculated Mass is the average molecular weight of the desired compound.
  For compounds with m □3000 found mass (average) is the result of a deconvolution using Masshunter Workstation Software Version B.05.00 Build 5.0.519.13 SP1 (Agilent).
LC-MS Method 4 (TOF):
System:Agilent 1290 infinity series UPLC
Column: Phenomenex Aeris widepore 3.6μ C4 50×2.1 mm
Detector: Agilent Technologies LC/MSD TOF 6230 (G6230A)
  Ionisation method: Agilent Jet Stream source
  Scanning range: m/z min. 100, m/z max. 3200
  linear reflector mode
  positive mode
  Step gradient: 5% to 90% B
  Gradient run-time: 10 minutes: 0-1 min 5-20% B, 1-7 min 20-90% B, 7-8 min 90% B 8-8.5 min 90-5% B 8.5-10 min 5% B
  Flow rate: 0.40 ml/min fixed
  Column temperature: 40° C.
  Solvent A: 99.90% H2O, 0.02% TFA
  Solvent B: 99.90% CH3CN, 0.02% TFA
  Solvent C: NA
  Calculated Mass is the average molecular weight of the desired compound.
  For compounds with m □3000 found mass (average) is the result of a deconvolution using Masshunter Workstation Software Version B.05.00 Build 5.0.519.13 SP1 (Agilent).

Synthesis of Substituents:

Substituents were synthesized either in solution or on solid phase as described in e.g. WO 2009/115469.

General Procedure for Acylation of Insulin-EGF(A) Fusion Proteins of the Invention:

The insulin-EGF(A) fusion protein is dissolved in an aqueous buffer, optionally added an organic co-solvent (e.g. EtOH, acetonitrile, DMSO, or NMP), and pH is adjusted to 11.2. A solution of the activated side chain in NMP (100 mg/mL) is added dropwise while keeping pH around 11.2 by addition of 1M NaOH, and the progress of the reaction is monitored by LC-MS. At completion of the reaction TFA, acetic acid or 1M HCl is added to the mixture. After dilution with water the mixture is purified by preparative HPLC. Pure fractions are pooled and lyophilised to afford the compound of the invention.

This general procedure is further illustrated in example 1 below. All other compounds of the invention were prepared similarly.

Example 1

EGF(A)(301L, 309R, 312E, 321E)-[GAQP]2-Insulin (B3E, B29K(hexadecanedioyl-gGlu-2×OEG), desB30) (SEQ ID NO: 17 and 2)

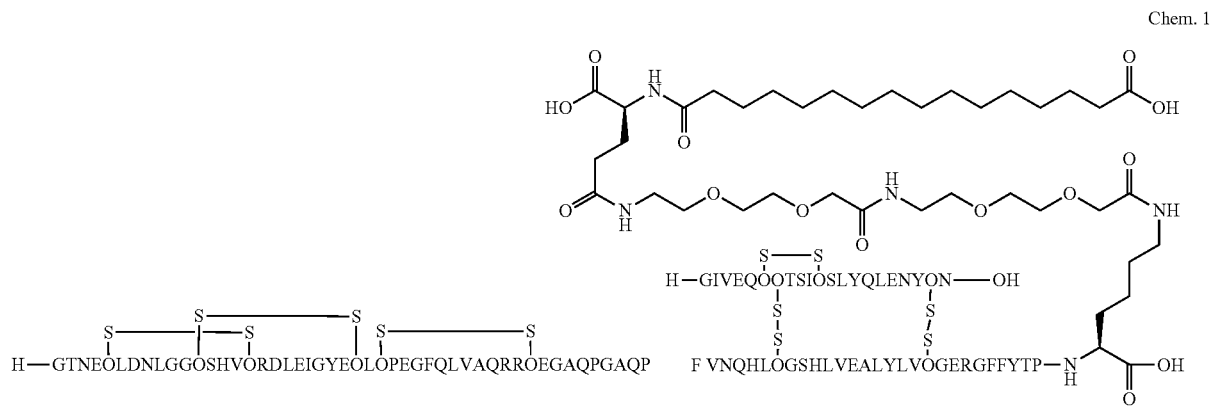

Chem. 1

A solution of EGF(A)(301L, 309R, 312E, 321E)-[GAQP]2-Insulin(B3E, desB30) (48 mL, 2.44 mg/mL, 117 mg) was dissolved in a buffer consisting of 20 mM Tris, pH 8.0, 10 mM CaCl$_2$), 10% EtOH, 50 mM NaCl. pH was raised to 11.1 with 1 M NaOH. A solution of hexadecanedioyl-Glu-2× OEG-OSu (24 mg in 0.5 mL NMP) was added dropwise while keeping pH at a constant 11.1 using 1M NaOH. After end reaction, the mixture was added TFA to pH 1.6. Acetonitrile (14 mL) was added to the mixture and thereafter with water to 100 mL. The mixture was purified by RP-HPLC.

Column: Phenomenex Gemini, 5 μM 5 u C18 110 Å, 30×250 mm
Flow: 20 mL/min
Buffer A: 0.1% TFA in milliQ water
Buffer B: 0.1% TFA in acetonitrile
Gradient: 20% B to 50% B, linear
Gradient time: 40 min
Fraction size: 6 mL Pure fractions were pooled and lyophilised to afford 56 mg of the title compound.

LC-MS 38 (electrospray): m/z=1873.28 (M+6)/6. Calc: 1873.27.
Rt=1.67 min

Example 2

EGF(A)(301L, 309R, 312E, 321E)-[GAQP]10-Insulin (B29K(octadecanedioyl-gGlu-2×OEG), desB30) (SEQ ID NO: 18 and 2)

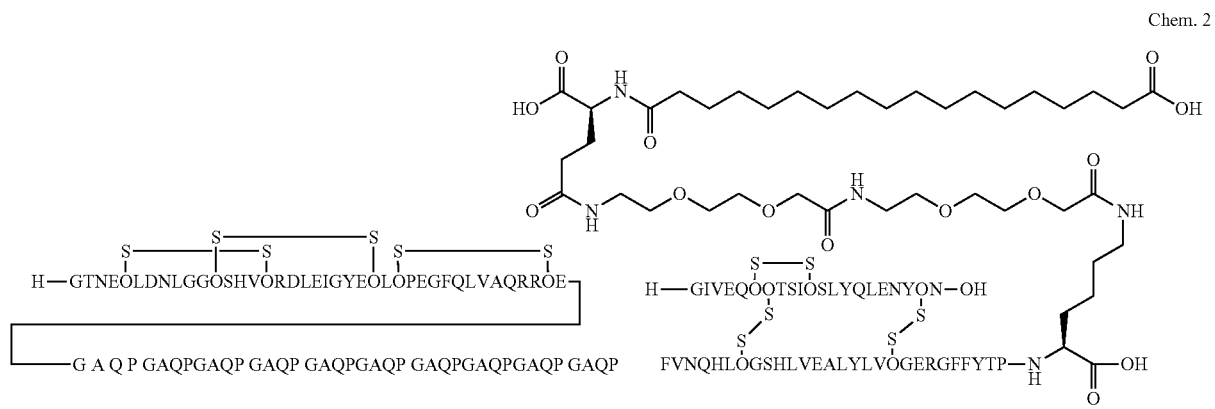

Chem. 2

LC-MS 38 (electrospray): m/z=1597.35 (M+9)/9. Calc: 1597.00.
Rt=1.75 min

Example 3
EGF(A)(301L, 309R, 312E, 321E)-[GAQP]2-Insulin (B3E, B29K(octadecanedioyl-gGlu-2×OEG), desB30) (SEQ ID NO: 17 and 2)
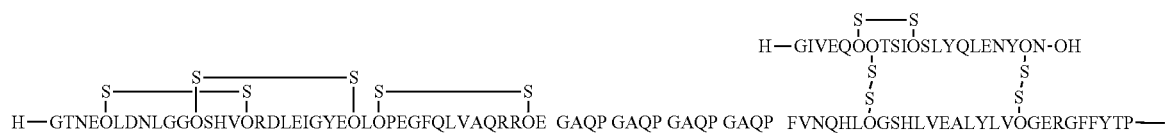
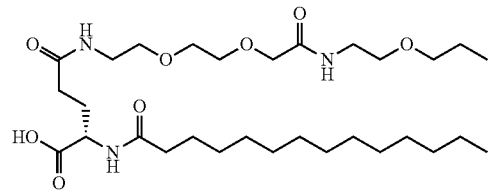
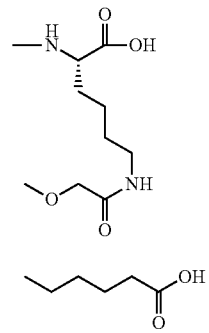
LC-MS 27 (TOF): m/z=11552.89. Calc: 11552.00.
Example 4
EGF(A)(301L, 309R, 312E, 321E)-[GAQP]2-Insulin (B29K(octadecanedioyl-gGlu-2×OEG), desB30) (SEQ ID NO: 19 and 2)
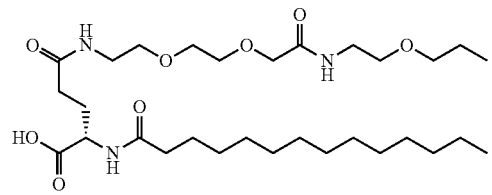

-continued
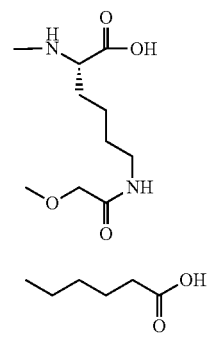
LC-MS METHOD 1 (electrospray): m/z=1924.39 (M+6)/6. Calc: 1923.83.
Rt=2.13 min
Example 5
EGF(A)(301L, 309R, 312E, 321E)-[GAQP]2-Insulin (B3E, B29K(octadecanedioyl-gGlu-OEG), desB30) (SEQ ID NO: 17 and 2)
Chem. 5
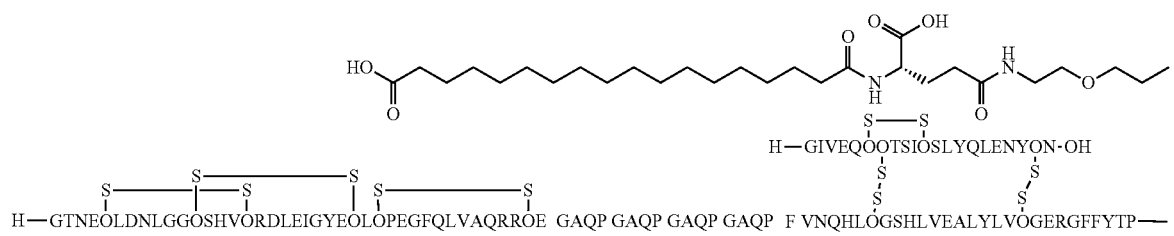
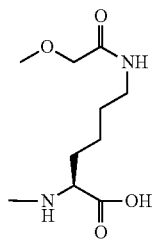
LC-MS METHOD 2 (electrospray): m/z=1902.01 (M+6)/6. Calc: 1902.1.
Rt=1.8 min

Example 6
EGF(A)(301L, 309R, 312E, 321E)-[GAQP]2-Insulin (B3E, B29K(eicosanedioyl-gGlu-2×OEG), desB30) (SEQ ID NO: 17 and 2)
Chem. 6
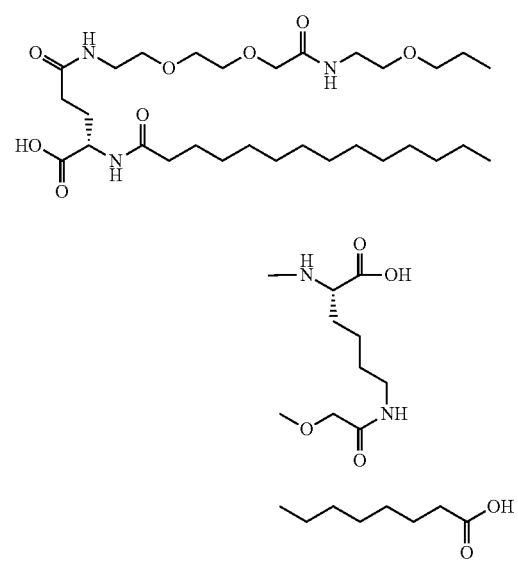
LC-MS METHOD 2 (electrospray): m/z=1930.74 (M+6)/6. Calc: 1931.02.
Rt=1.89 min.
Example 7
EGF(A)(301L, 309R, 312E, 321E)-[GAQP]2-Insulin (B29K(eicosanedioyl-gGlu-2×OEG), desB30) (SEQ ID NO: 19 and 2)
Chem. 7
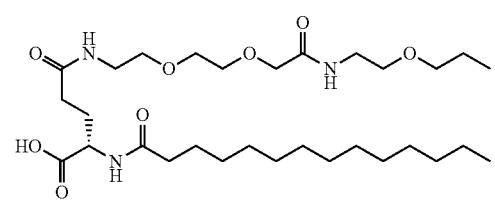

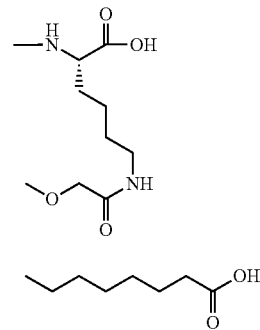
LC-MS METHOD 1 (electrospray): m/z=1928.67 (M+6)/6. Calc: 1928.51.
Rt=2.27 min
Example 8
EGF(A)(301L, 309R, 312E, 321E)-[GQAP]2-Insulin (B29K(octadecanedioyl-gGlu-2×OEG), desB30) (SEQ ID NO: 28 and 2)
Chem. 8
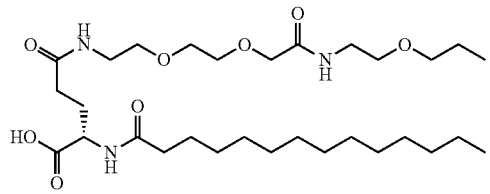
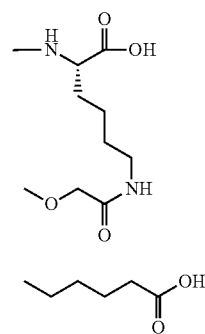
LC-MS METHOD 1 (electrospray): m/z=1924.33 (M+6)/6. Calc: 1923.83.
Rt=1.87 min

Example 9
EGF(A)(301L, 309R, 312E, 321E)-[GAQP]13-Insulin (B29K(octadecanedioyl-gGlu-2×OEG), desB30) (SEQ ID NO: 20 and 2)
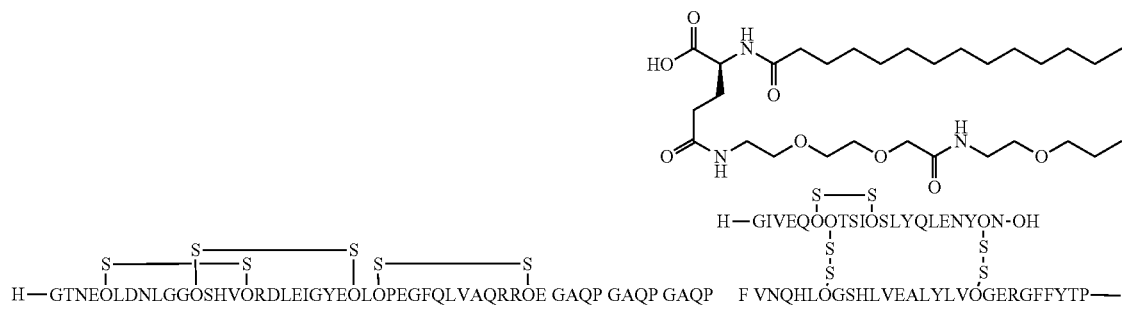
Chem. 9
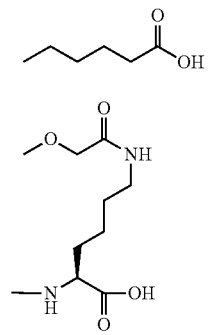
LC-MS METHOD 1 (electrospray): m/z=1983.44 (M+6)/6. Calc: 1982.72.
Rt=2.00 min
Example 10
EGF(A)(301L, 309R, 312E, 321E)-[GAQP]3-Insulin (A14E, B29K(octadecanedioyl-gGlu-2×OEG), desB30) (SEQ ID NO: 20 and 27)
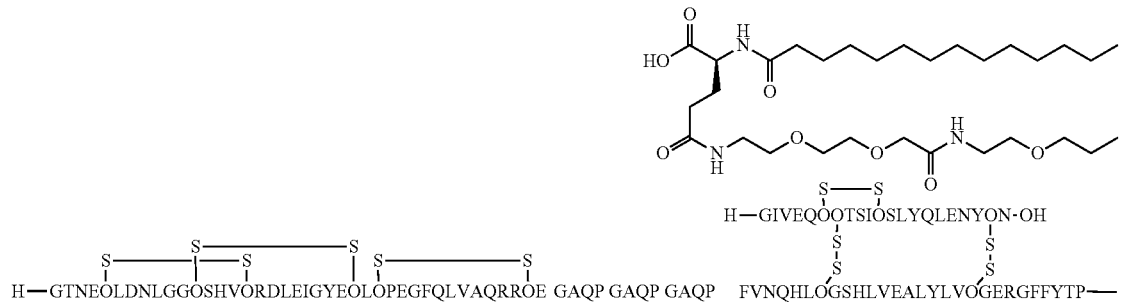
Chem. 10

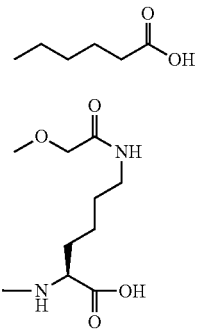
LC-MS METHOD 2 (electrospray): m/z=1977.18 (M+6)/6. Calc: 1977.05.
Rt=1.8 min
Example 11
EGF(A)(301L, 309R, 312E, 321E)-[GAQP]4-Insulin (A14E, B29K(octadecanedioyl-gGlu-2×OEG), desB30) (SEQ ID NO: 21 and 27)
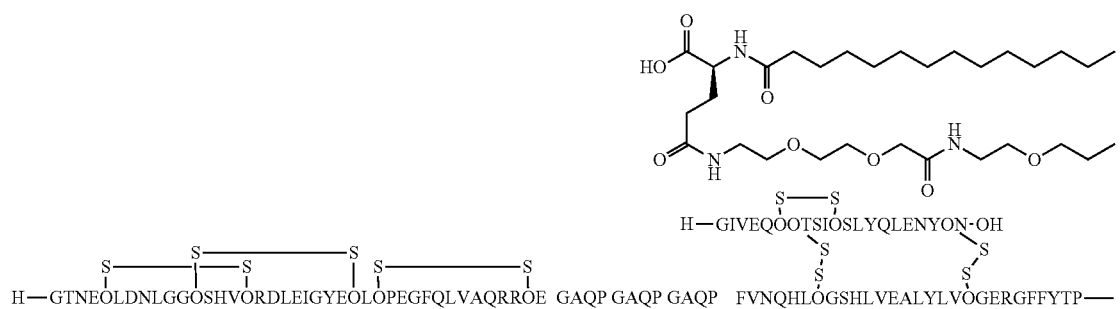
Chem. 11
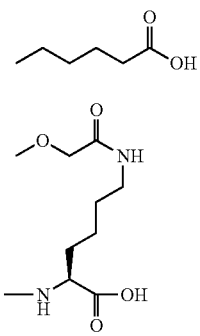
LC-MS METHOD 2 (electrospray): m/z=1527.13 (M+8)/8. Calc: 1527-2.
Rt=1.78 min

Example 12
EGF(A)(301L, 309R, 312E, 321E)-[GAQP]4-Insulin (B29K(octadecanedioyl-gGlu-2×OEG), desB30) (SEQ ID NO: 21 and 2)
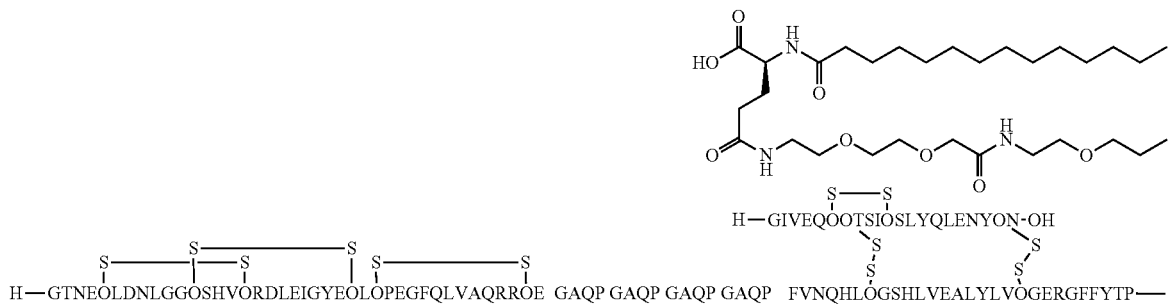
Chem. 12
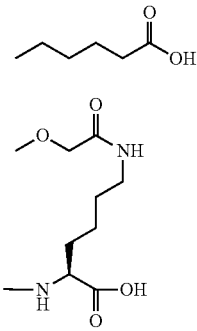
LC-MS METHOD 2 (electrospray): m/z=1749.96 (M+7)/7. Calc: 1750.10.
Rt=1.71 min
Example 13
EGF(A)(301L, 309R, 312E, 321E)-[GAQP]6-Insulin (A14E, B29K(octadecanedioyl-gGlu-2×OEG), desB30) (SEQ ID NO: 22 and 27)
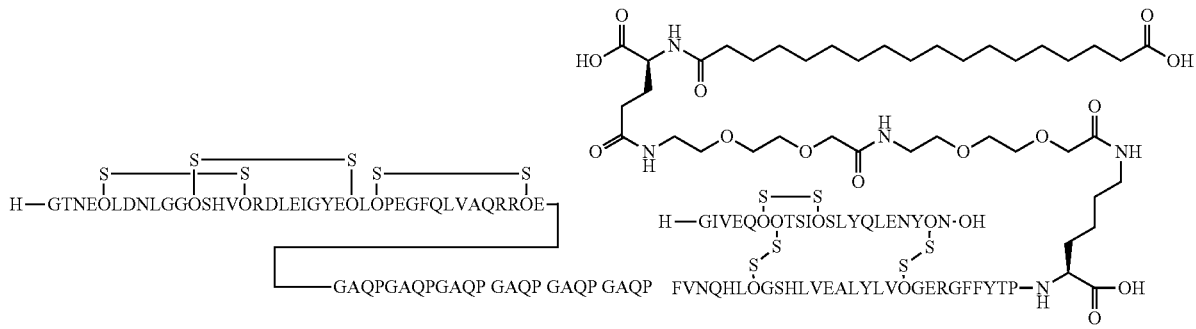
Chem. 13
LC-MS METHOD 2 (electrospray): m/z=1845.9 (M+7)/7. Calc: 1846.2.
Rt=1.74 min

Example 14
EGF(A)(301L, 309R, 312E, 321E)-[GAQP]6-Insulin (B29K(octadecanedioyl-gGlu-2×OEG), desB30) (SEQ ID NO: 22 and 2)
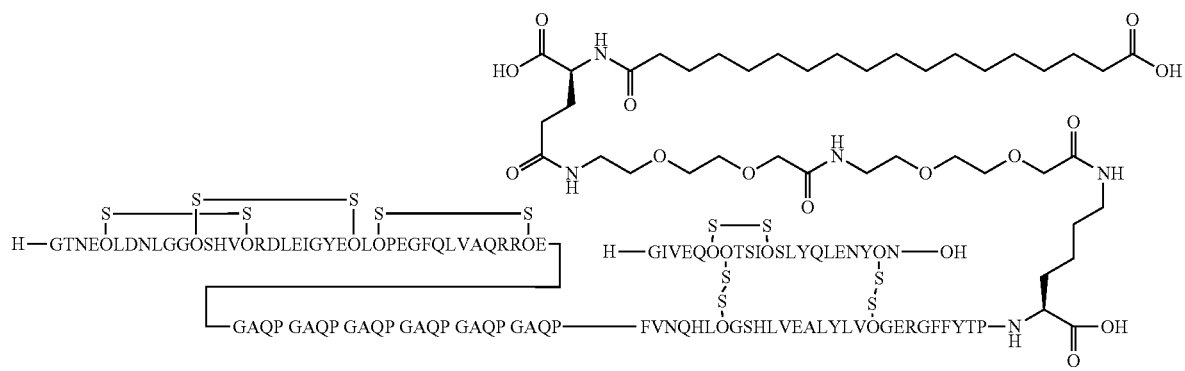
Chem. 14
LC-MS METHOD 1 (electrospray): m/z=1851.01 (M+7)/7. Calc: 1851.07.
Rt=2.07 min
Example 15
EGF(A)(301L, 309R, 312E, 321E)-[GAQP]6-Insulin (A14E, B29K(octadecanedioyl-gGlu-OEG), desB30) (SEQ ID NO: 22 and 27)
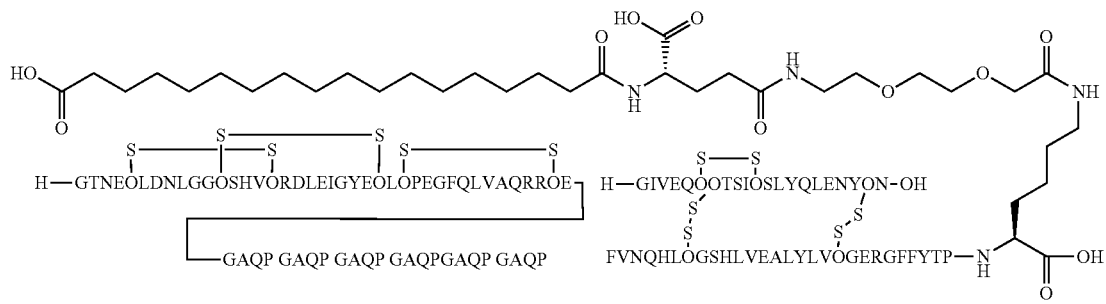
Chem. 15
LC-MS METHOD 4 (TOF): m/z=12771.82; Calc: 12771.26.

Example 16
EGF(A)(301L, 309R, 312E, 321E)-[GAQP]6-Insulin (A14E, B29K(eicosanedioyl-gGlu-2×OEG), desB30 (SEQ ID NO: 22 and 27)
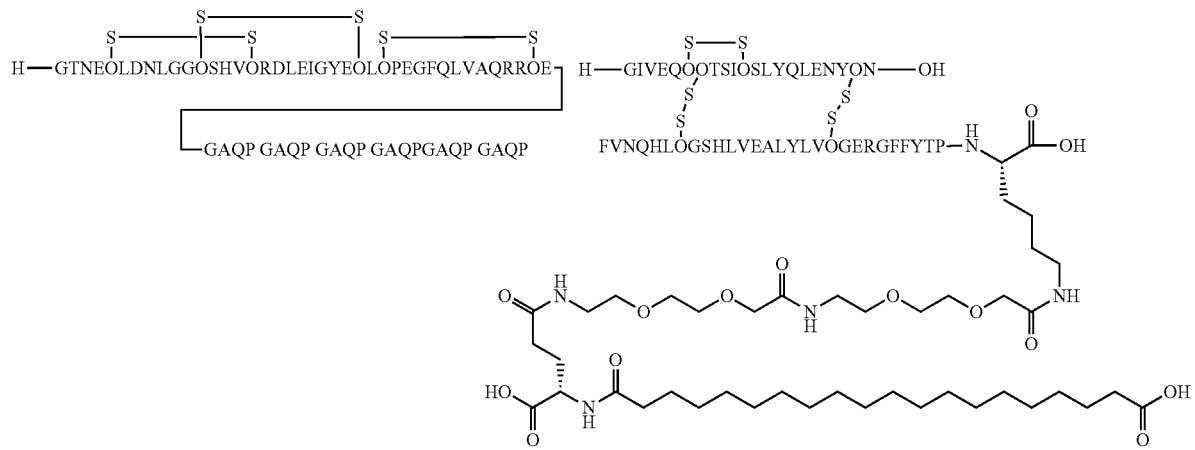
Chem. 16
LC-MS METHOD 2 (electrospray): m/z=1850.16 (M+7)/7. Calc: 1850.21.
Rt=1.98 min
Example 17
EGF(A)(301L, 309R, 312E, 321E)-[GAQP]8-Insulin (B29K(octadecanedioyl-gGlu-2×OEG), desB30) (SEQ ID NO: 23 and 2)
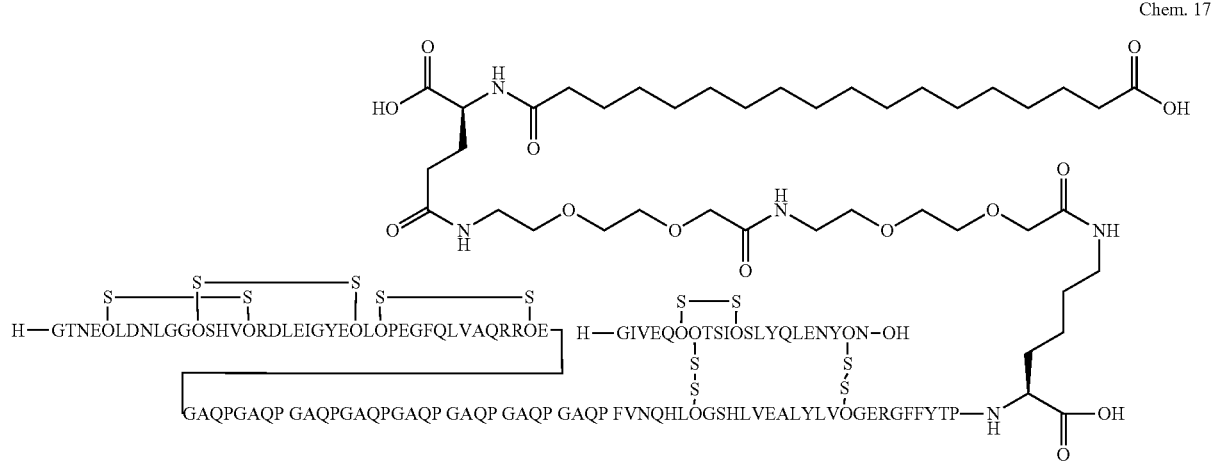
Chem. 17
LC-MS METHOD 2 (electrospray): m/z=1708.15 (M+8)/8. Calc: 1708.15.
Rt=1.74 min

Example 18
EGF(A)(301L, 309R, 312E, 321E)-[GAQP]12-Insulin (B29K(octadecanedioyl-gGlu-2×OEG), desB30) (SEQ ID NO: 24 and 2)
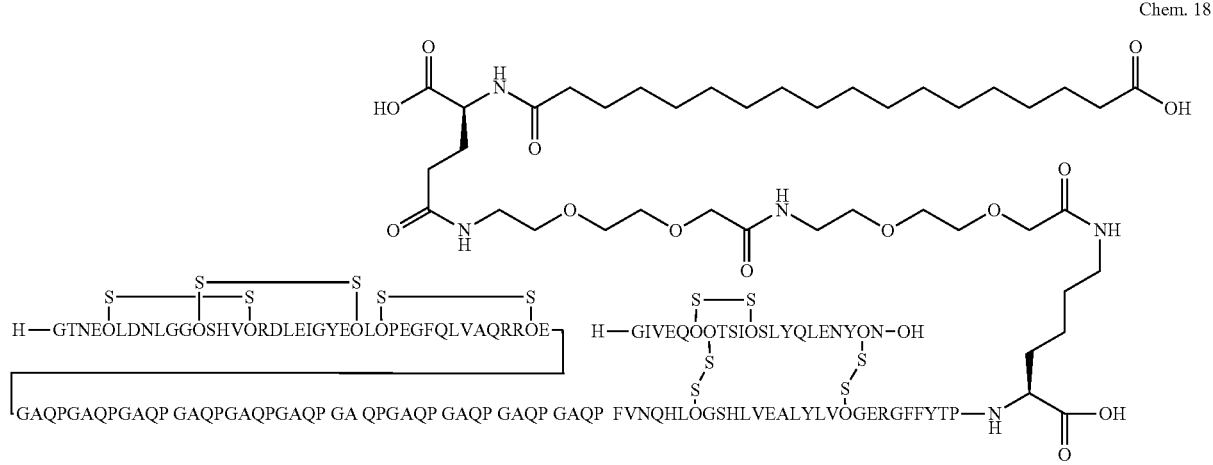
Chem. 18
LC-MS METHOD 1 (electrospray): m/z=1884.76 (M+8)/8. Calc: 1884.84.
Rt=2.04 min
Example 19
EGF(A)(301L, 309R, 312E, 321E)-[GAQP]19-Insulin (B29K(octadecanedioyl-gGlu-2×OEG), desB30) (SEQ ID NO: 25 and 2)
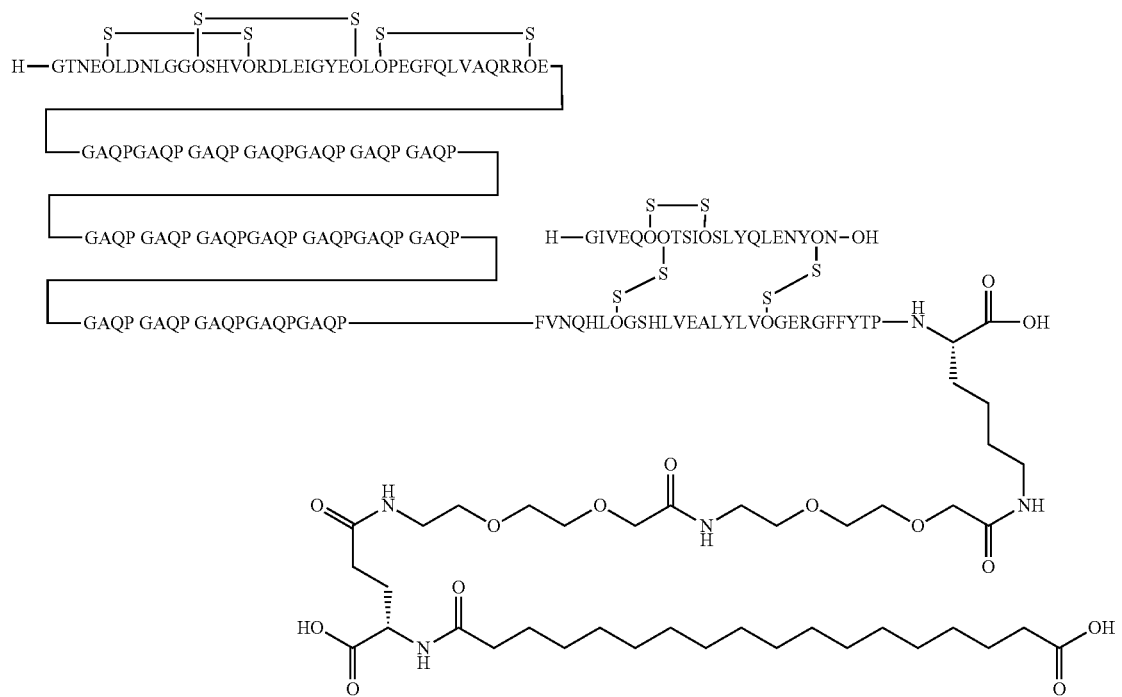
Chem. 17
LC-MS METHOD 3 (TOF): m/z=17545.17; Calc: 17544.34.

Example 20
EGF(A)(301L, 309R, 312E, 321E)-[GAQP]119-Insulin (A14E, B29K(octadecanedioyl-gGlu-2xOEG), desB30) (SEQ ID NO: 25 and 27)
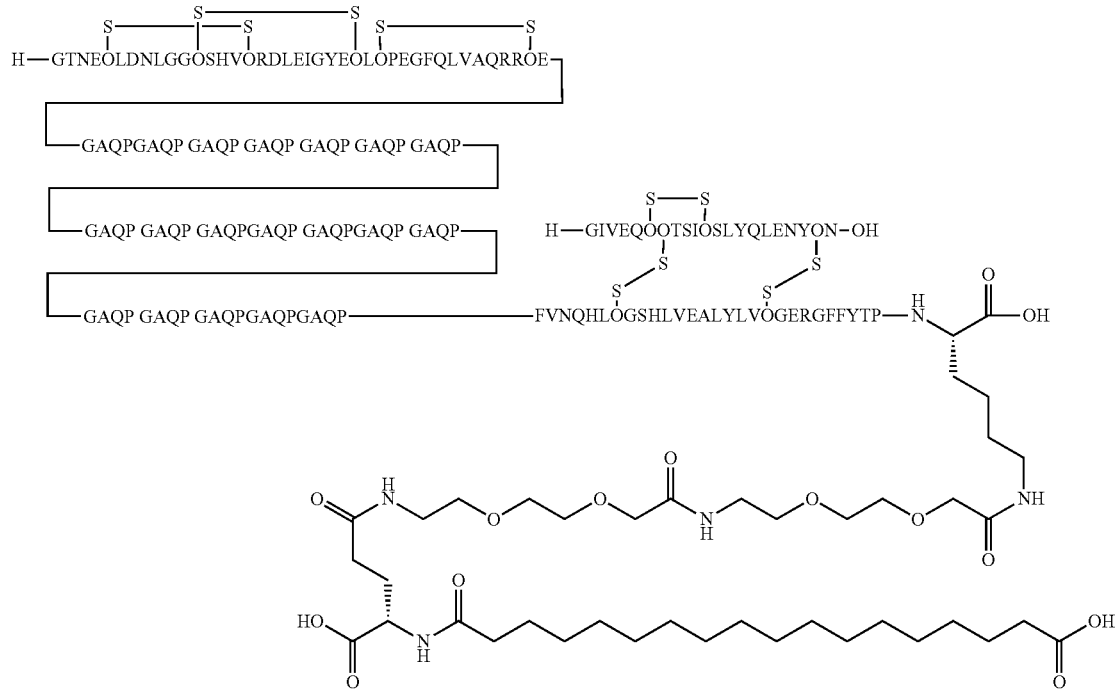
Chem. 20
LC-MS METHOD 1 (electrospray): m/z=1947.0 (M+9)/9. Calc: 1946.6.
Rt=1.73 min
Example 21
EGF(A)(301L, 309R, 312E, 321E)-[GAQP]119-Insulin (B3E, B29K(octadecanedioyl-gGlu-2xOEG), desB30) (SEQ ID NO: 26 and 2)
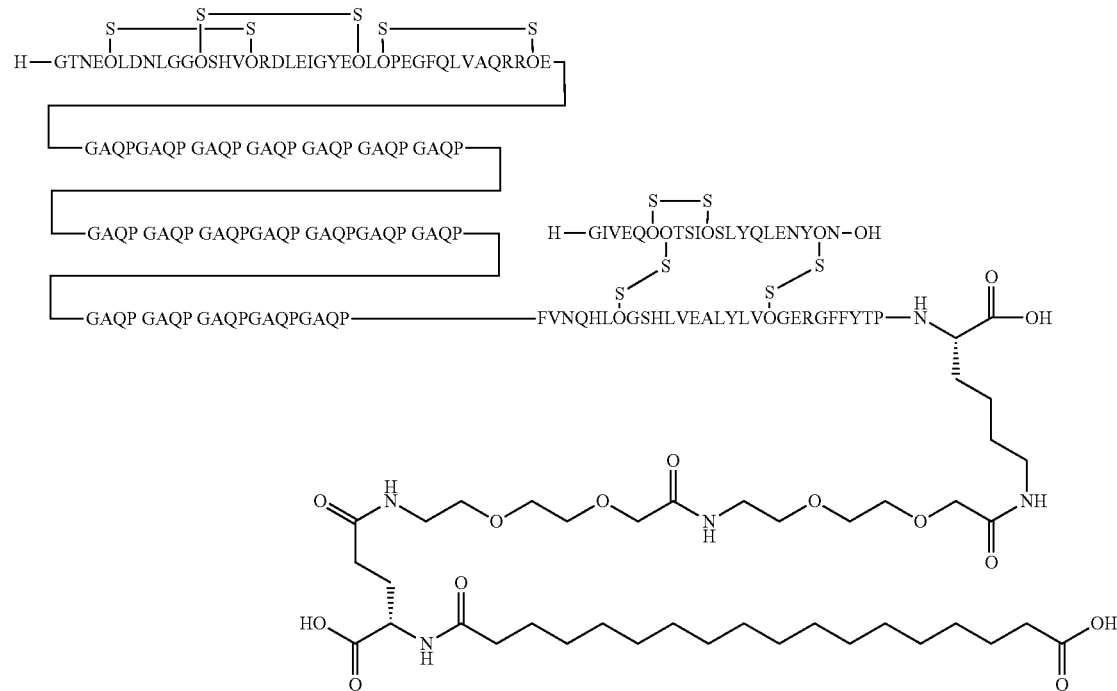
Chem. 21

LC-MS METHOD 3 (TOF): m/z=17559.93; Calc: 17559.35.
Example 22
EGF(A)(301L, 309R, 312E, 321E)-[GAQP]19-Insulin (B29K(eicosanedioyl-gGlu-2×OEG), desB30) (SEQ ID NO: 25 and 2)
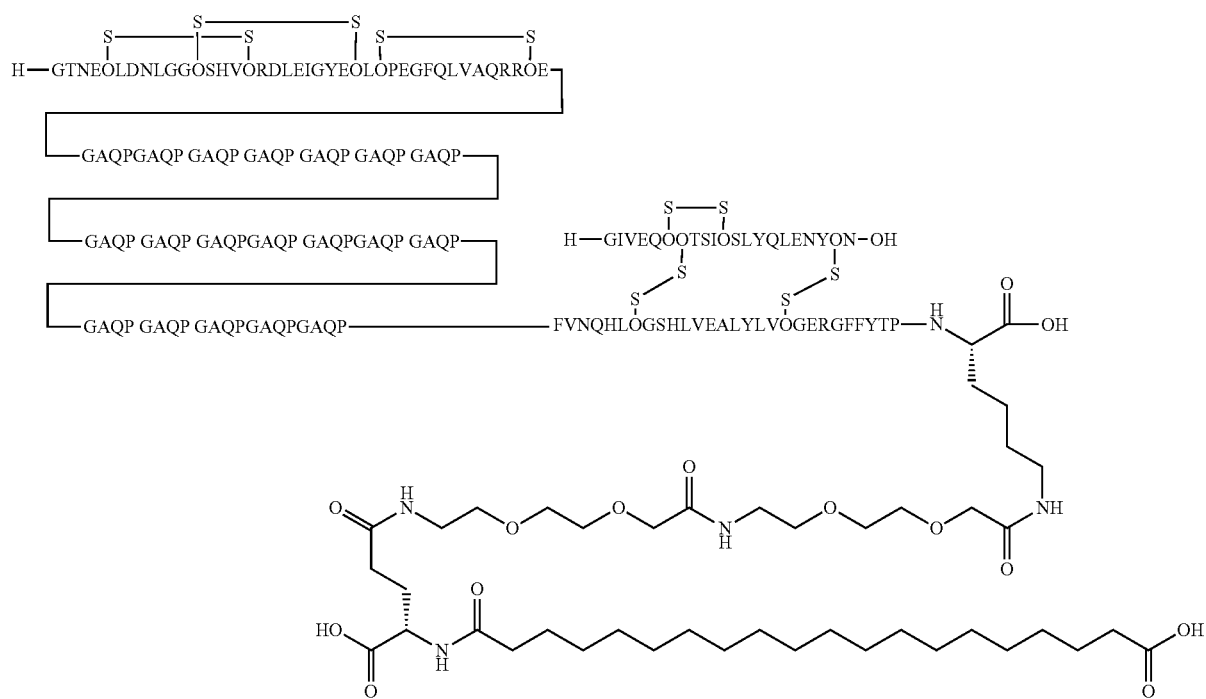
Chem. 22
LC-MS METHOD 3 (TOF): m/z=17573.37; Calc: 17572.39.

Example 23
EGF(A)(301L, 309R, 312E, 321E)-[GAQP]19-Insulin (A14E, B29K(eicosanedioyl-gGlu-2×OEG), desB30) (SEQ ID NO: 25 and 27)
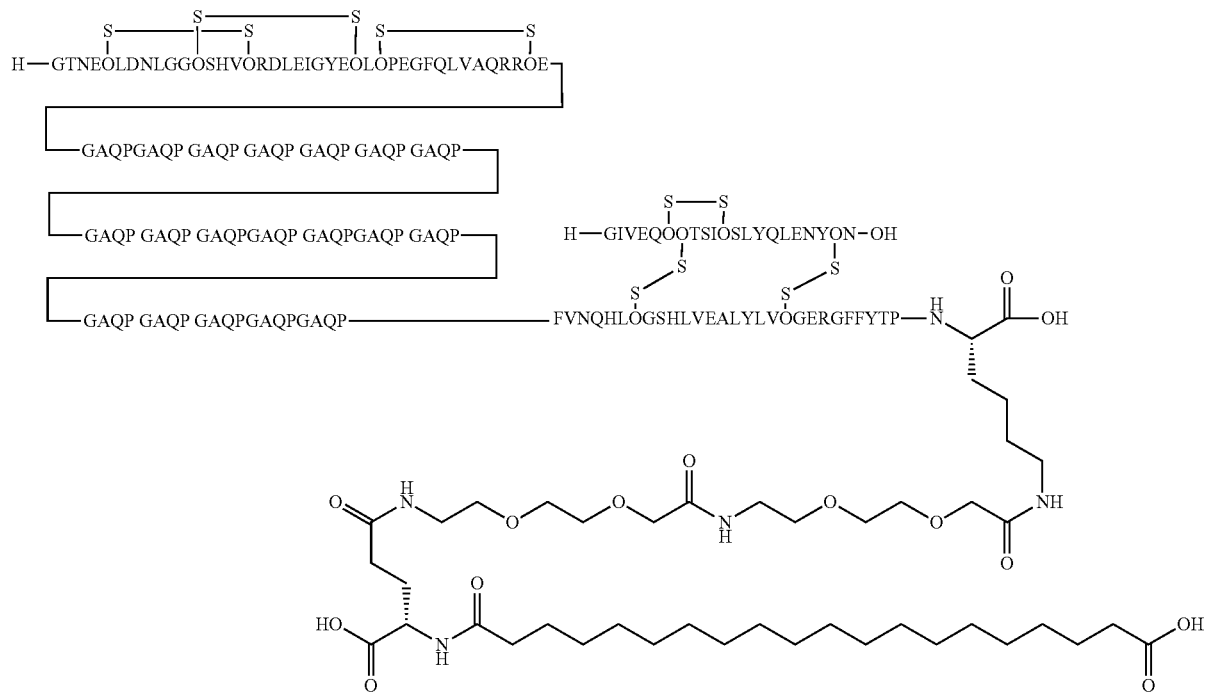
Chem. 22
LC-MS METHOD 1 (electrospray): m/z=1462.45 (M+12)/12. Calc: 1462.53.
Rt=1.84 min
Example 24
EGF(A)(301L, 309R, 312E, 321E)-[GAQP]119-Insulin (B3E, B29K(eicosanedioyl-gGlu-2×OEG), desB30) (SEQ ID NO: 26 and 2)
Chem. 24
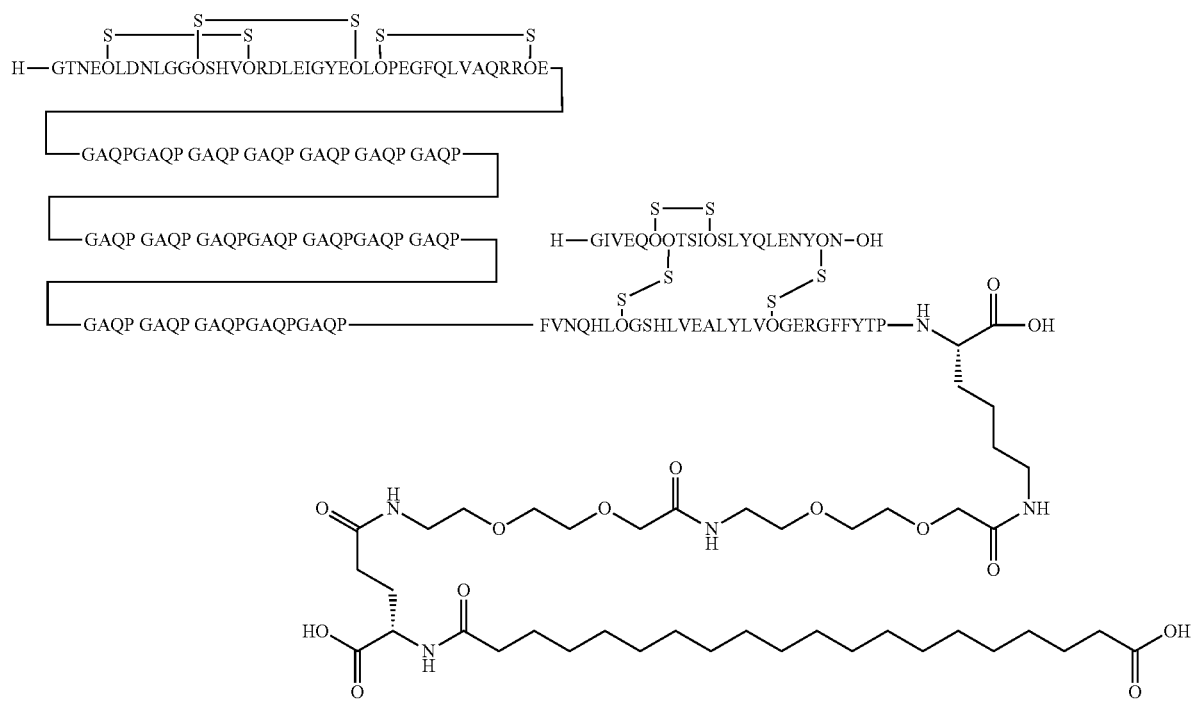

LC-MS METHOD 3 (TOF): m/z=17587.97; Calc: 17587.40.

Comparator Compound 1

EGF(A)(301L, 309R, 312E, 321E)-[GQEP]2-Insulin (B29K(octadecanedioyl-gGlu-2×OEG), desB30) (SEQ ID NO: 29 and 2)

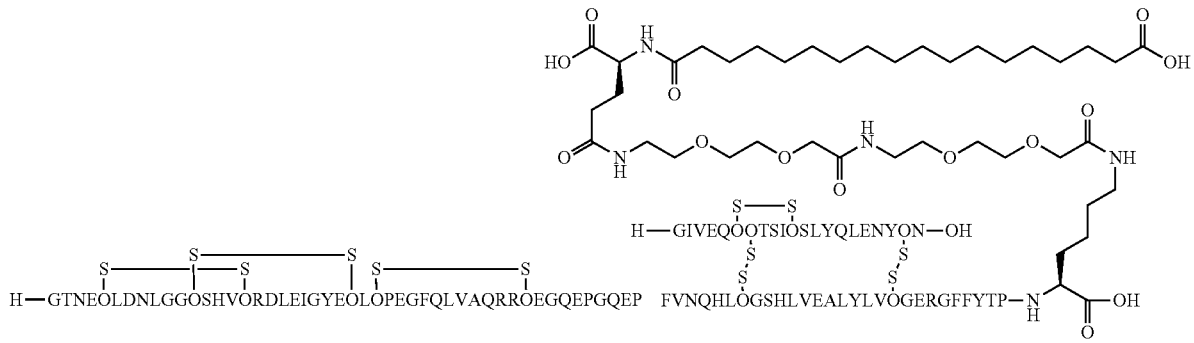

LC-MS METHOD 1 (electrospray): m/z=1943.59 (M+6)/6. Calc: 1943.18.

Rt=2.09 min

Comparator Compound 2

EGF(A)(301L, 309R, 312E, 321E)-[GQEP]8-Insulin (A14E, B29K(octadecanedioyl-gGlu-2×OEG), desB30) (SEQ ID NO: 30 and 27)

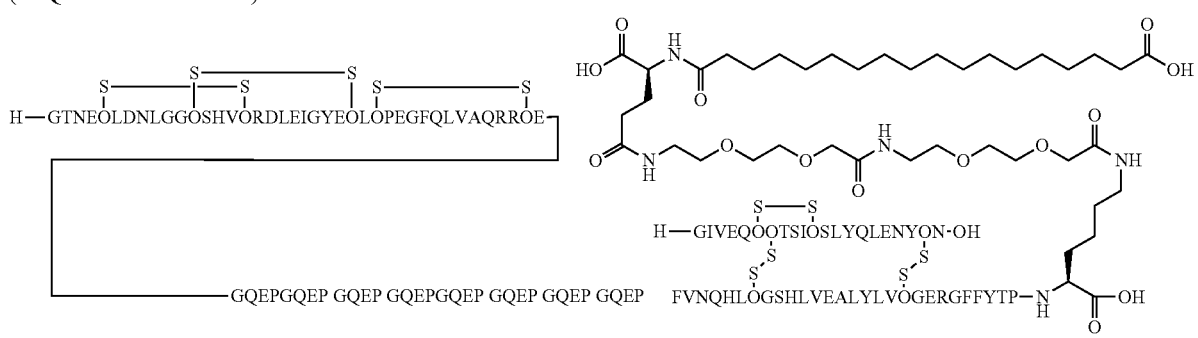

LC-MS METHOD 1 (electrospray): m/z=1566.29 (M+9)/9. Calc: 1566.27.

Rt=1.79 min

Comparator Compound 3

EGF(A)(301L, 309R, 312E, 321E)-[GQEP]4-Insulin (B29K(eicosanedioyl-gGlu-2×OEG), desB30) (SEQ ID NO: 31 and 2)

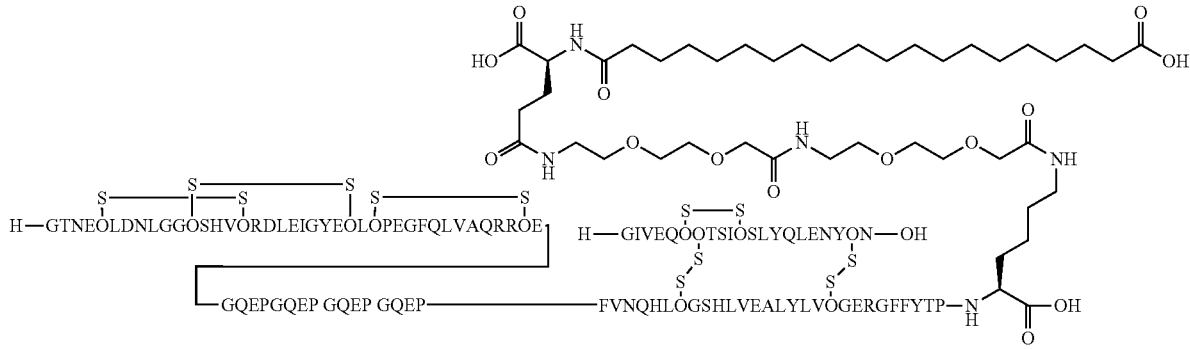

LC-MS METHOD 1 (electrospray): m/z=1787.19 (M+7)/7. Calc: 1787.28.

Rt=2.16 min

Comparator Compound 4

EGF(A)(301L, 309R, 312E, 321E)-[GQEP]4-Insulin (B29K(octadecanedioyl-gGlu-2×OEG), desB30) (SEQ ID NO: 31 and 2)

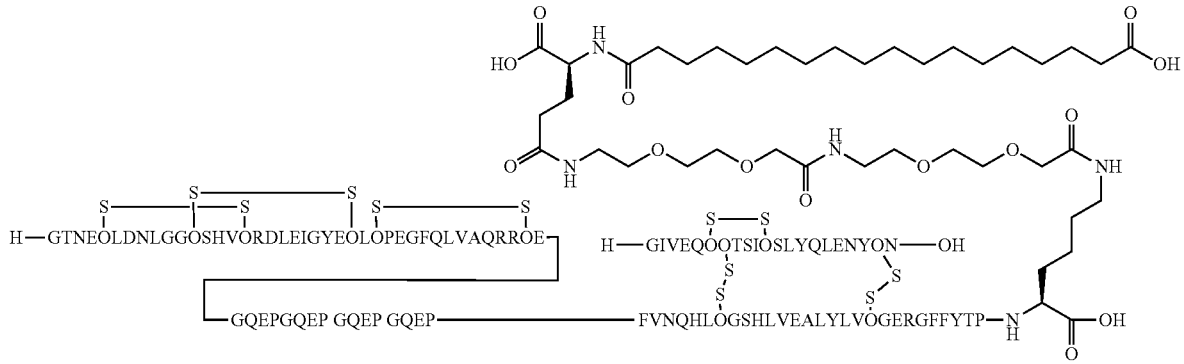

LC-MS METHOD 3 (TOF): m/z=12473; Calc: 12475.

Comparator Compound 5

EGF(A)(301L, 309R, 312E, 321E)-[GQEP]2-Insulin (B29K(hexadecanedioyl-gGlu-2×OEG), desB30) (SEQ ID NO: 29 and 2)

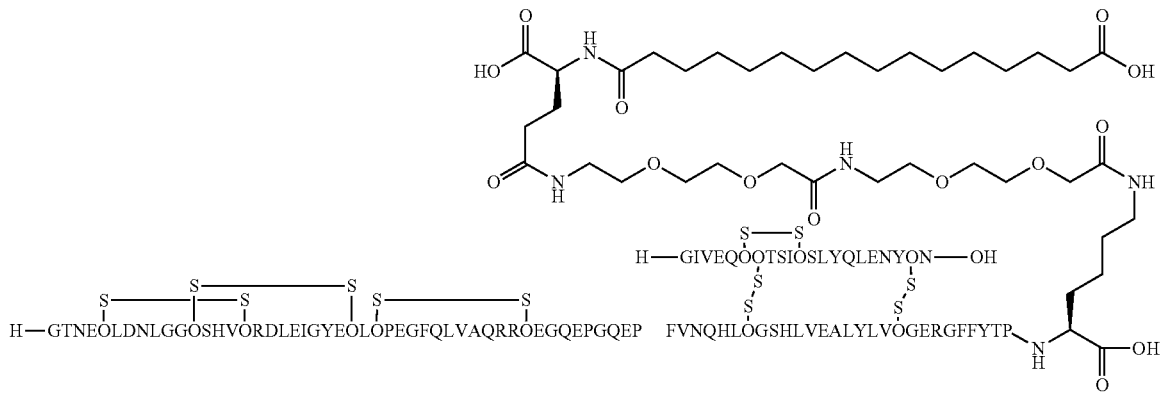

LC-MS METHOD 3 (TOF): m/z=11625.00; Calc: 11625.00.

Comparator Compound 6

EGF(A)(301L, 309R, 312E, 321E)-[GQEP]6-Insulin (B29K(octadecanedioyl-gGlu-2×OEG), desB30) (SEQ ID NO: 32 and 2)

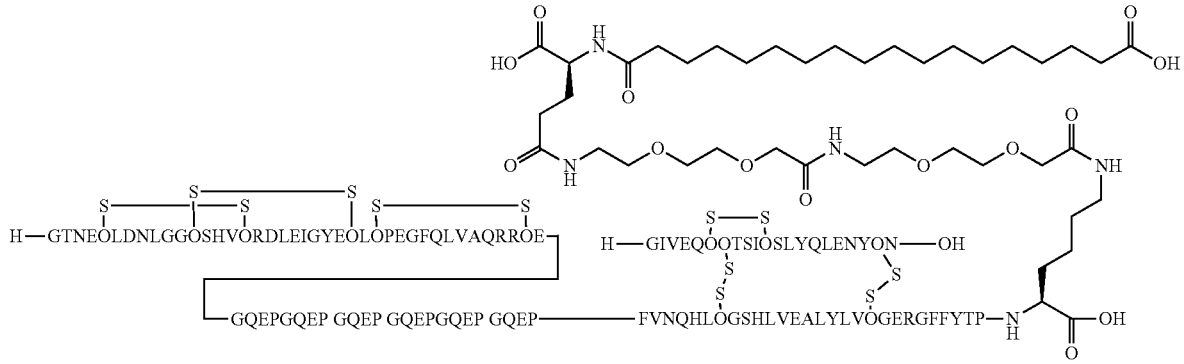

LC-MS METHOD 3 (TOF): m/z=13296; Calc: 13298.

Comparator Compound 7

EGF(A)(301L, 309R, 312E, 321E)-[GQEP]8-Insulin (A14E, B29K(hexadecanedioyl-gGlu-2×OEG), desB30) (SEQ ID NO: 30 and 27)

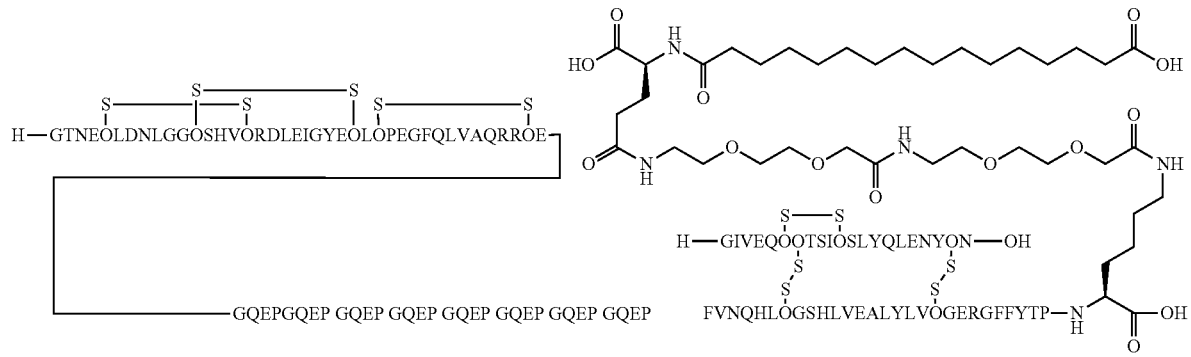

LC-MS METHOD 1 (electrospray): m/z=1758.57 (M+8)/8. Calc: 1758.43.

Rt=1.67 min

Comparator Compound 8

B29K(octadecanedioyl-gGlu-2×OEG), desB30 human insulin (SEQ ID NO: 2 and 33)

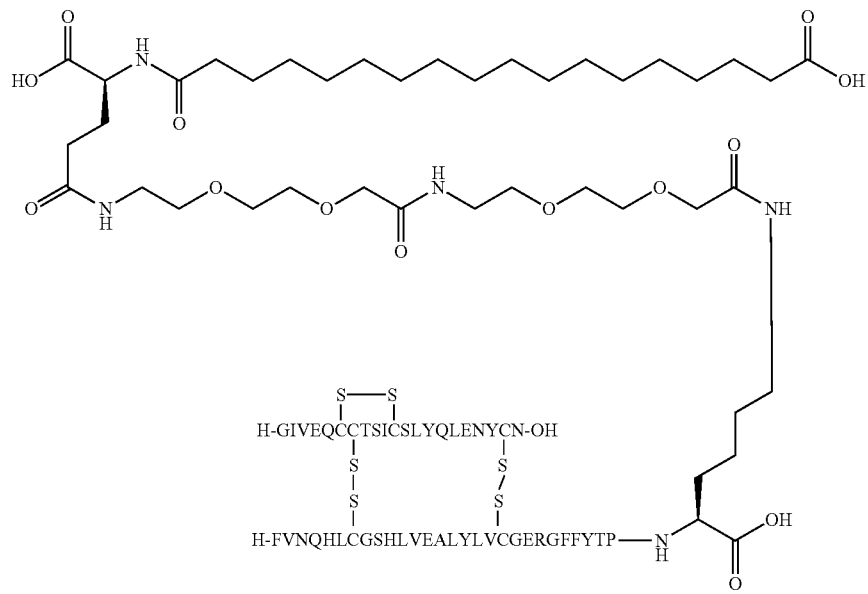

This is a molecule of the prior art, disclosed in WO 2009/022006, example 1.

Comparator Compound 9

EGF(A)(301L, 309R, 312E, 321E) (SEQ ID NO: 34)

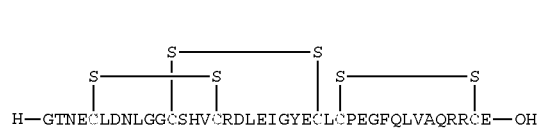

This compound was prepared as described in WO2017121850.

Comparator Compound 10
EGF(A)(301L, 309R, 312E, 321E, 328K(hexadecane-dioyl-gGlu-2×OEG), 330K(hexadecanedioyl-gGlu-2×OEG)) (SEQ ID NO: 34)

Insulin receptor affinities and other in vitro data of selected insulin analogues of the invention are presented in Table 3, below and data on comparator compounds are presented in Table 4 below.

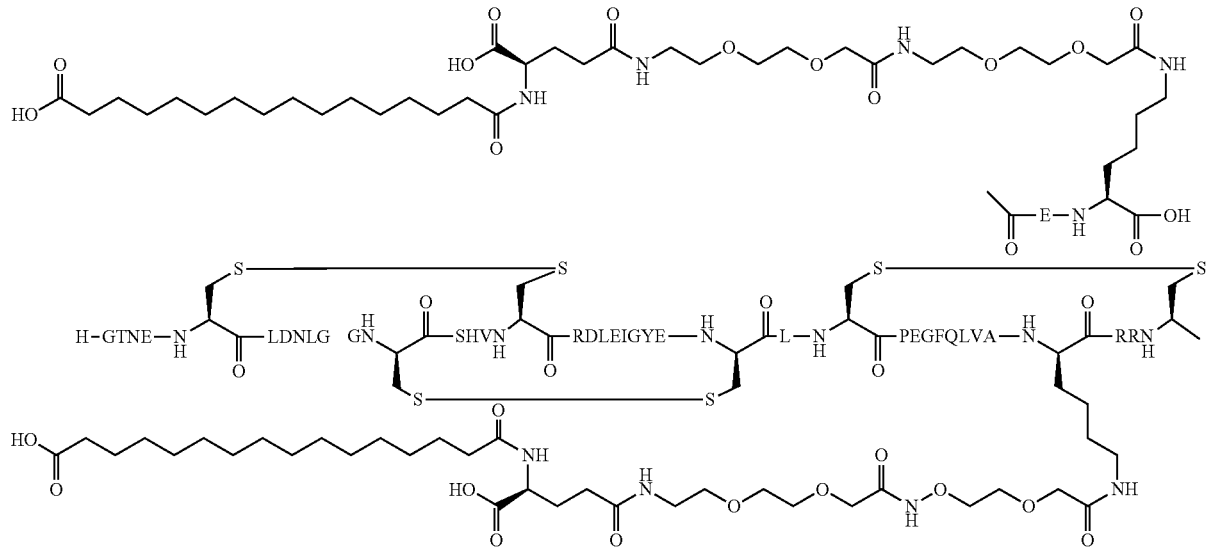

This is a molecule disclosed in WO 2017/121850, example 151.

Example 25

Insulin Receptor Affinity of Selected Insulin Derivatives of the Invention, Measured on Solubilised Receptors The relative binding affinity of the insulin analogues of the invention for the human insulin receptor (IR) is determined by competition binding in a scintillation proximity assay (SPA) (according to Glendorf T et al. (2008) *Biochemistry* 47 4743-4751).

In brief, dilution series of a human insulin standard and the insulin analogue to be tested are performed in 96-well Optiplates (Perkin-Elmer Life Sciences) followed by the addition of [$^{125}$I-A14Y]-human insulin, anti-IR mouse antibody 83-7, solubilised human IR-A (semipurified by wheat germ agglutinin chromatography from baby hamster kidney (BHK) cells overexpressing the IR-A holoreceptor), and SPA beads (Anti-Mouse polyvinyltoluene SPA Beads, GE Healthcare) in binding buffer consisting of 100 mM HEPES (pH 7.8), 100 mM NaCl, 10 mM MgSO$_4$, and 0.025% (v/v) Tween 20. Plates are incubated with gentle shaking for 22-24 h at 22° C., centrifuged at 2000 rpm for 2 minutes and counted on a TopCount NXT (Perkin-Elmer Life Sciences).

Data from the SPA are analysed according to the four-parameter logistic model (Vølund A (1978) *Biometrics* 34 357-365), and the binding affinities of the analogues calculated relative to that of the human insulin standard measured within the same plate.

A related assay is also used wherein the binding buffer contains 1.5% HSA (w/v) (Sigma A1887) in order to mimic more physiological conditions.

Example 26

Lipogenesis in Rat Adipocytes

As a measure of in vitro potency of the insulins of the invention, lipogenesis can be used. Primary rat adipocytes are isolated from the epididymale fat pads and incubated with 3H-glucose in buffer containing e.g. 1% fat free HSA and either standard (human insulin, HI) or insulin of the invention. The labelled glucose is converted into extractable lipids in a concentration dependent way, resulting in full concentration response curves. The result is expressed as relative potency (%) with 95% confidence limits of insulin of the invention compared to standard (HI).

Data are given in Tables 3 and 4, below.

TABLE 3

Insulin receptor binding data in absence and presence of HSA (0 or 1.5%) as well as functional lipogenesis data from rat adipocytes of selected analogues of the invention

| Ex. No. | hIR-A 0% HSA (% rel to HI) Ex. No. 25 | hIR-A 1.5% HSA (% rel to HI) Ex. No. 25 | Lipogenesis 1% HSA (% rel to HI) Ex. No. 26 |
|---|---|---|---|
| 1 | 10.8 | 1.20 | 0.49 |
| 2 | 5.85 | 0.31 | |
| 3 | 10.6 | 0.48 | 0.16 |
| 4 | 9.16 | 0.35 | 0.13 |
| 5 | 7.89 | 0.28 | |
| 6 | 9.99 | 0.40 | 0.06 |
| 7 | | | |
| 8 | 11.6 | 0.51 | 0.14 |
| 9 | 9.04 | 0.44 | 0.12 |
| 10 | 6.61 | 0.48 | 0.12 |
| 11 | 6.85 | 0.36 | 0.12 |
| 12 | 8.47 | 0.62 | 0.14 |
| 13 | 5.53 | 0.35 | 0.11 |
| 14 | 5.98 | 0.30 | 0.10 |
| 15 | 5.70 | 0.23 | 0.08 |
| 16 | 4.77 | 0.26 | 0.08 |
| 17 | 5.82 | 0.34 | |

TABLE 3-continued

Insulin receptor binding data in absence and presence of HSA (0 or 1.5%) as well as functional lipogenesis data from rat adipocytes of selected analogues of the invention

| Ex. No. | hIR-A 0% HSA (% rel to HI) Ex. No. 25 | hIR-A 1.5% HSA (% rel to HI) Ex. No. 25 | Lipogenesis 1% HSA (% rel to HI) Ex. No. 26 |
|---|---|---|---|
| 18 | 4.70 | 0.25 | 0.09 |
| 19 | 4.49 | 0.25 | 0.09 |
| 20 | 2.99 | 0.14 | 0.03 |
| 21 | 4.43 | 0.31 | 0.07 |
| 22 | 4.17 | 0.18 | 0.06 |
| 23 | 2.89 | 0.14 | 0.02 |
| 24 | 4.15 | 0.29 | 0.06 |

TABLE 4

IR (A isoform) receptor binding data in absence and presence of HSA (0 and/or 1.5%) as well as functional lipogenesis data from rat adipocytes of comparator compounds

| Comparator compound No. | hIR-A 0% HSA (% rel to HI) Ex. No. 25 | hIR-A 1.5% HSA (% rel to HI) Ex. No. 25 | Lipogenesis 1% HSA (% rel to HI) Ex. No. 26 |
|---|---|---|---|
| 1 | 8.44 | 0.26 | 0.14 |
| 2 | 3.43 | 0.26 | 0.06 |
| 3 | 6.16 | 0.34 | 0.06 |
| 4 | 7.56 | 0.33 | 0.07 |
| 5 | 11.6 | 0.78 | 0.44 |
| 6 | 6.03 | 0.26 | 0.06 |
| 7 | 3.68 | 0.44 | 0.18 |
| 8 | 14.7 | 0.75 | 0.30 |

It can be seen that the insulin receptor binding (and lipogenic potency) of the compounds of the invention and of comparator compounds are not different, and, thus, independent of the composition (charge) of the linker. This is in striking contrast to the observed differences in in vivo potencies (Example 30) where comparator compounds, containing charged GQEP linkers are significantly less potent compared to compounds of the invention.

It can also be seen that by appending the EGF(A) peptide via a peptidic linker to the N-terminal of the insulin roughly halves the insulin receptor affinity, both in absence and in presence of 1.5% HSA.

Example 27

PCSK9-LDL-R Binding Competitive (ELISA)

The aim of this assay is to measure the apparent binding affinity of EGF(A) compounds to PCSK9.

Due to their ability to inhibit the interaction of PCSK9 with LDL-R, compounds of the invention may also be referred to as PCSK9 inhibitors.

The day before the experiment, recombinant human Low Density Lipoprotein Receptor (rhLDL-R; NSO-derived; R & D systems #2148-LD or in-house production) was dissolved at 1 μg/mL in 50 mM sodium carbonate, pH 9.6, and then 100 μL of the solution was added to each well of the assay plates (Maxisorp 96, NUNC #439454) and coated overnight at 4° C. On the day of the experiments, 8-point concentration curves of the EGF(A) compounds containing Biotinylated PCSK9 (0.5 ug/mL, BioSite/BPSBioscience cat #71304 or in-house production) were made in duplicate. EGF(A) compound and biotinylated PCSK9 mixtures were prepared an incubated for 1 hour at room temperature in assay buffer containing 25 mM Hepes, pH 7.2 (15630-056, 100 ml, 1M), 150 mM NaCl (Emsure 1.06404.1000) 1% HSA (Sigma A1887-25G) 0.05% Tween 20(Calbiochem 655205) 2 mM $CaCl_2$ (Sigma 223506-500G). The coated assay plates were then washed 4× in 200 μl assay buffer, and then 100 μL of the mixture of EGF(A) compounds and biotinylated PCSK9 was added to the plates and incubated 2 h at room temperature. The plates were washed 4× in 200 μL assay buffer and then incubated with Streptevadin-HRP (25 ng/mL; VWR #14-30-00) for 1 h at room temperature. The reaction is detected by adding 50 μL TMB-on (KEM-EN-TEC) and incubated 10 min in the dark. Then the reaction was stopped by adding 50 μL 4 M $H_3PO_4$ to the mixture, added by electronic multi pipetting. The plates were then read in a Spectramax at 450 and 620 nm within 1 h. The 620 nm read was used for background subtraction. 1050 values were calculated using Graphpad Prism, by nonlinear regression log(inhibitor) vs. response-variable slope (four parameters), and converted into Ki values using the following formula: Ki=IC50/(1+(Biotin-PCSK9)/(kd(Biotin-PCSK9))), where Kd of the biotin-PCSK9 is 1.096727714 μg/mL and [Biotin-PCSK9]=0.5 (μg/mL).

The results of compounds of the invention are shown in Table 5 below, and data for comparator compounds in Table 5 below. Higher Ki values reflect lower apparent binding affinities to PCSK9 and vice versa. In general a large number of the tested EGF(A) compounds displayed the ability to inhibit PCSK9 in binding to the hLDL-R in the low nM range.

TABLE 5

Apparent PCSK9 binding affinity (Ki in nM) and LDL uptake in HepG2 cells ($EC_{50}$ in nM) for compounds of the invention

| Example No. | PCSK9 binding Ki (nM) (Ex. No. 27) | LDL uptake $EC_{50}$ (nM) (Ex. No. 28) |
|---|---|---|
| 1 | 2.18 | |
| 2 | 3.28 | |
| 3 | 1.55 | 107 |
| 4 | 1.56 | |
| 5 | 1.68 | |
| 6 | 2.49 | |
| 7 | | |
| 8 | 1.57 | 132 |
| 9 | 1.09 | |
| 10 | 1.47 | |
| 11 | 1.58 | |
| 12 | 2.14 | |
| 13 | 1.92 | 170 |
| 14 | 1.78 | |
| 15 | 2.07 | |
| 16 | 1.75 | |
| 17 | 2.40 | |
| 18 | 1.60 | |
| 19 | 1.65 | |
| 20 | 2.12 | 123 |
| 21 | 2.13 | |
| 22 | 2.05 | |
| 23 | 2.14 | 126 |
| 24 | 1.86 | |

TABLE 6

Apparent PCSK9 binding affinity (Ki in nM) and LDL uptake in HepG2 cells ($EC_{50}$ in nM) for comparator compounds

| Comparator compound No. | PCSK9 binding Ki (nM) (Ex. No. 27) | LDL uptake $EC_{50}$ (nM) (Ex. No. 28) |
|---|---|---|
| 1 | 1.81 | |
| 2 | 1.76 | |
| 3 | 1.41 | |
| 4 | 1.53 | |
| 5 | 1.61 | |
| 6 | 1.09 | |
| 7 | 1.74 | |
| 9 | 3.80 | |
| 10 | 1.90 | 152 |
| wt EGF(A) SEQ ID No. 1 | 618 | 12845 |

It can be seen that the PCSK9 binding of the compounds of the invention and of comparator compounds are not different, and, thus, independent of the composition (charge) of the linker.

It can also be observed that appending a linker and an insulin to the C-terminal of the EGF(A) peptide does not alter the binding to PCSK9.

Example 28

LDL Uptake Assay in HepG2 Cells

An alternative assay to determine the inhibitory potency of the PCSK9 peptides and derivatives thereof measuring uptake of LDL in HepG2 cells is described here below.

Assay Principle: LDL uptake is primarily mediated by the endogenously expressed hLDL-Rs, and thus LDL uptake capacity is an indirect measure of LDL-R expression. The hLDL-Rs can be down-regulated by incubation with exogenous PCSK9 in a dose dependent fashion. Thus PCSK9 incubation will decrease the ability of cells to take up LDL molecules. This down-regulation of LDL uptake can then be antagonized by the addition of compounds neutralizing or inhibiting the PCSK9/LDL-R binding. Consequently PCSK9 inhibitors can be characterized based on their capacity to increase LDL uptake in the presence of PCSK9 and e.g. counter act the PCSK9 mediated hLDL-R down-regulation.

The assay is performed using HepG2 cells (Sigma Aldrich ECACC: Acc no. 85011430) grown in 10% Lipoprotein deficient Foetal Calf Serum (Sigma Aldrich #S5394) and the capacity of the cells to take up BODIPY fluorescently labelled LDL particles (Life technologies Europe BV #L3483) is measured.

Assay protocol: The 96 well plates (Perkin Elmer, ViewPlate-96 Black #60005182) were coated with Poly-D-Lysin (10 mg/L, Sigma Aldrich #P6407 dissolved in PBS Gibco #14190-094) for 1 hour at 37° C. in incubator. Then the plates were washed 2× in 100 μL PBS (Gibco #14190-094). Test compositions for 8 point concentration curves of the EGF(A) compounds were prepared all containing PCSK9 (10 ug/mL; in-house production) diluted in Assay medium (DMEM (Gibco #31966-021), 10% Lipoprotein deficient Foetal Calf Serum (Sigma Aldrich #S5394) and 1% Pen Strep (Cambrex #DE17-602E)), and added on to the plates in a volume of 50 uL/well.

After 30-60 minutes 50.000 HepG2 cells (Sigma-Aldrich: ECACC: Atcc no. 85011430 lot: 136023), diluted in Assay medium were added in a volume of 50 μL/well, and the plates were incubated 20 hours (at 37° C., 5% $CO_2$) in $CO_2$ permeable plastic bags (Antalis Team, LDPE bag 120/35× 300×0,025 mm #281604). Hereafter, the plates were emptied and immediately hereafter 50 μL FL-LDL (Life technologies Europe BV #L3483) in a concentration of 10 μg/mL in Assay Medium was added to each well, and the plates were incubated for 2 hours (at 37° C., 5% $CO_2$) in $CO_2$ permeable plastic bag using the black cover on the lid to protect from light. The plates were emptied and washed 2 times with 100 μL of PBS (Gibco #14190-094). Then 100 μL of PBS (Gibco #14190-094) was added and within 15 min hereafter, the plates were read (bottom read) using the following filters Ex (515 nm)/Em (520 nm) on a SpecktraMax M4 (Molecular Probes, Invitrogen Detection Technologies).

Finally, EC50 values were calculated using GraphPad Prism, nonlinear regression curve fit, sigmoidal dose-response (variable slope).

The results are shown in the table above. Lower EC50 values reflects higher capacity to reverse the PCSK9 mediated down-regulation of LDL uptake, and inversely a high EC50 value is indicative for a compound with low capacity to inhibit the PCSK9 mediated down-regulation of LDL uptake.

As can be seen the tested compounds display an EC50 in the LDL uptake assay of 100-200 nM, which is indicative of compounds with a high capacity to reverse the PCSK9 mediated down-regulation of LDL uptake.

Example 29

Rat Pharmacokinetics, Intravenous Rat PK:

Conscious, non-fasted male Sprague-Dawley rats, ~300 grams are dosed intravenously (i.v.) with insulin analogs at various doses and plasma concentrations of the employed compounds are measured using immunoassays or mass spectrometry at specified intervals for up to 48 hours post-dose. Pharmacokinetic parameters are subsequently calculated using WinNonLin Professional (Pharsight Inc., Mountain View, Calif., USA).

TABLE 7

Rat PK data (mean residence time) following intravenous administration of compounds of the invention

| Example No | Rat iv Mean Residence Time MRT (h) |
|---|---|
| 8 | 6.64 |
| 4 | 7.03 |
| 19 | 9.45 |
| 22 | 10.78 |
| 21 | 9.44 |
| 24 | 11.47 |
| 3 | 7.55 |
| 6 | 9.01 |
| 9 | 7.97 |
| 14 | 7.82 |
| 18 | 7.7 |
| 12 | 7.59 |
| 13 | 13.56 |

TABLE 8

Rat PK data (mean residence time) following intravenous administration of comparator compounds

| Comparator compound No | Rat iv Mean Residence Time MRT (h) |
|---|---|
| 1 | 6.77 |
| 2 | 12.18 |
| 3 | 7.44 |

It is concluded that compounds of the invention possess similar PK profiles as the similar comparator compounds. Thus, the PK data cannot explain the observed surprising differences in in vivo potencies (Example 30) where comparator compounds, containing charged GQEP linkers are significantly less potent compared to compounds of the invention.

Example 30

Subcutaneous PK/PD Profiles of Insulin Analogues of the Invention and the Prior Art in Sprague Dawley Rats The fusion peptide derivatives of the invention may be tested by subcutaneous administration to rats, e.g. comparing with similar B29K acylated insulin analogues of the prior art according to this protocol. The derivatives may be tested for pharmacokinetic and/or pharmacodynamic parameters.

In Vivo Protocol

Conscious, non-fasted, male Sprague-Dawley rats, ~350 grams, are used for these experiments. During the study period (up to 30 hours after dosing), the rats have free access to water and food. Rats are dosed subcutaneously (90 nmol/kg; 600 µM formulation of insulin derivative) in the neck using a NovoPen Echo®. Blood samples are drawn (sublingual vein; 200 µl into Microvette®200 EDTA tubes) and plasma collected at the time points 0 (before dosing) and 15 minutes, 1, 2, 4, 5.5, 7, 24, 29/30 hours and eventually daily up to 30 hours after dosing of the insulin derivative. Plasma concentrations of glucose and eventually insulin derivatives are quantified using a BIOSEN analyser and immuno assays/LCMS analysis, respectively.

It is concluded from FIGS. 1 & 2 that the spacers 2×GAQP, 3×GAQP, 4×GAQP, 6×GAQP, 8×GAQP, and 10×GAQP are conferring equal insulin potency, whereas the longer spacers 12×GAQP and 19×GAQP compromise insulin potency.

Figure 3:
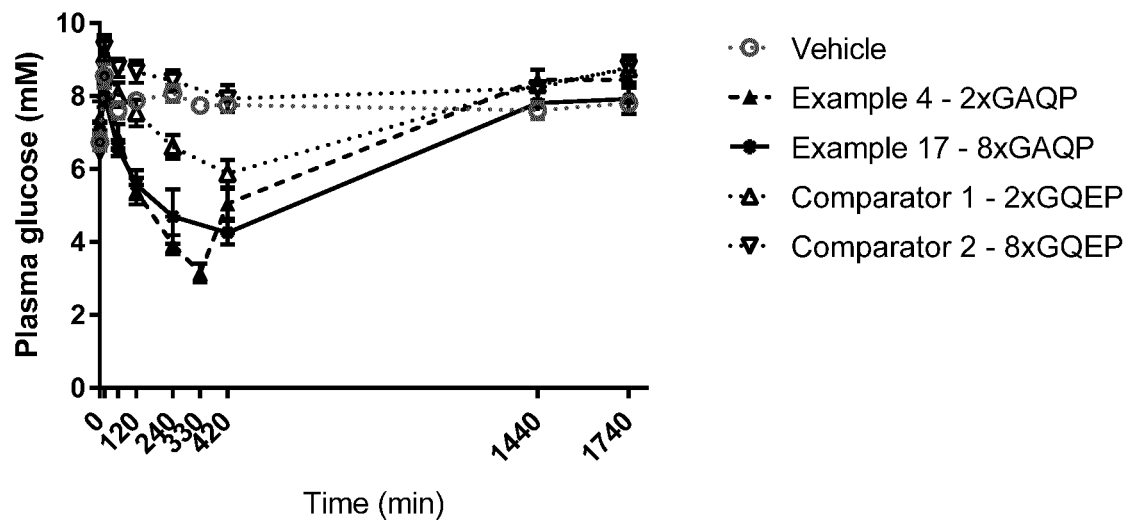
FIG. 3 shows the blood glucose lowering effects of the compounds of examples 4 and 17 of the invention, with different lengths of GQAP/GAQP spacers, relative to the blood glucose lowering effects of the comparator compounds 1 and 2 with GQEP spacers, all with the octadecanedioyl-gGlu-2×OEG side chain and vehicle.

From observing FIG. 3, it is concluded that the spacers 2×GAQP and 8×GAQP are conferring equal insulin potency, whereas the spacers 2×GQEP and 8×GQEP surprisingly and significantly compromises insulin potency.

Figure 4:
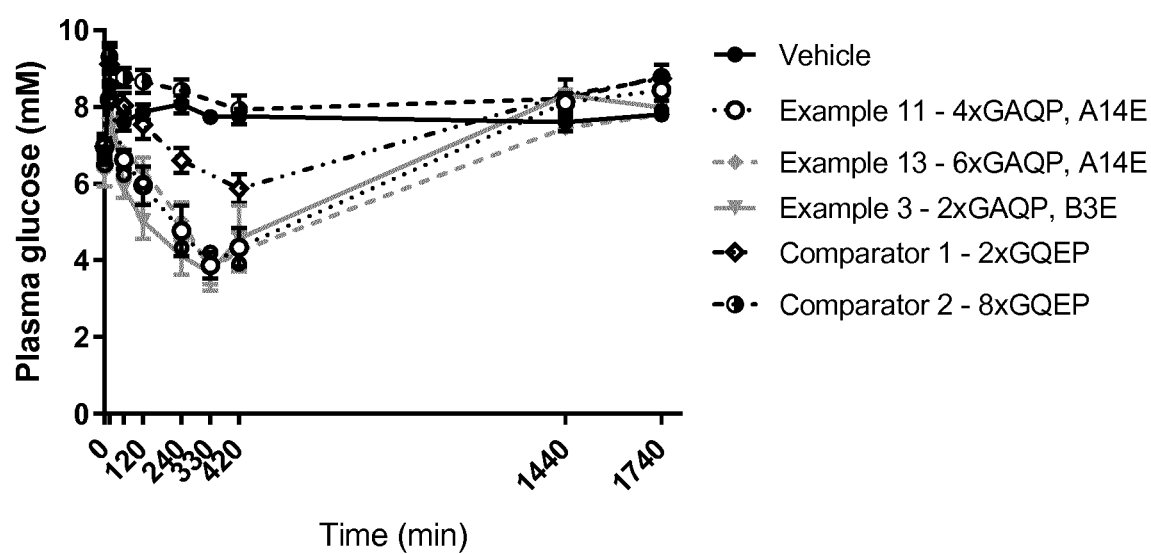
FIG. 4 shows the blood glucose lowering effects of the compounds of examples 3, 11, and 13 of the invention, with different lengths of GQAP/GAQP spacers, relative to the blood glucose lowering effects of the comparator compounds 1 and 2 with GQEP spacers, all with the octadecanedioyl-gGlu-2×OEG side chain and vehicle.

From observing FIG. 4, it is concluded that the blood glucose lowering effects of the compound containing linkers 2×GAQP, 4×GAQP, and 6×GQAP, with insulin substitutions A14E or B3E are equipotent and superior to the blood glucose lowering effects of the comparator compounds 1 and 2, containing the linkers 2×GQEP and 8×GQEP, respectively, and vehicle.

Figure 5:
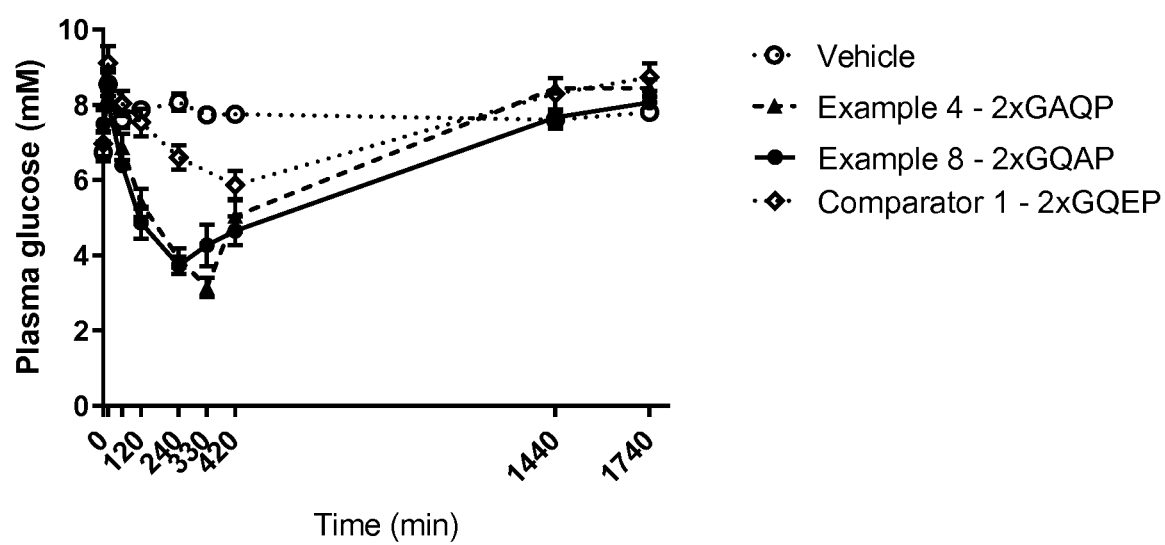
FIG. 5 shows the blood glucose lowering effects of the compounds of examples 4 and 8 of the invention with 2×GQAP/GAQP spacers, relative to the blood glucose lowering effect of the comparator compound 1 with 2×GQEP spacer, all with the octadecanedioyl-gGlu-2×OEG side chain.

From observing FIG. 5 it is concluded that the spacers 2×GAQP and 2×GQAP are conferring equal insulin potency, whereas the spacer 2×GQEP surprisingly compromises insulin potency.

Figure 6:
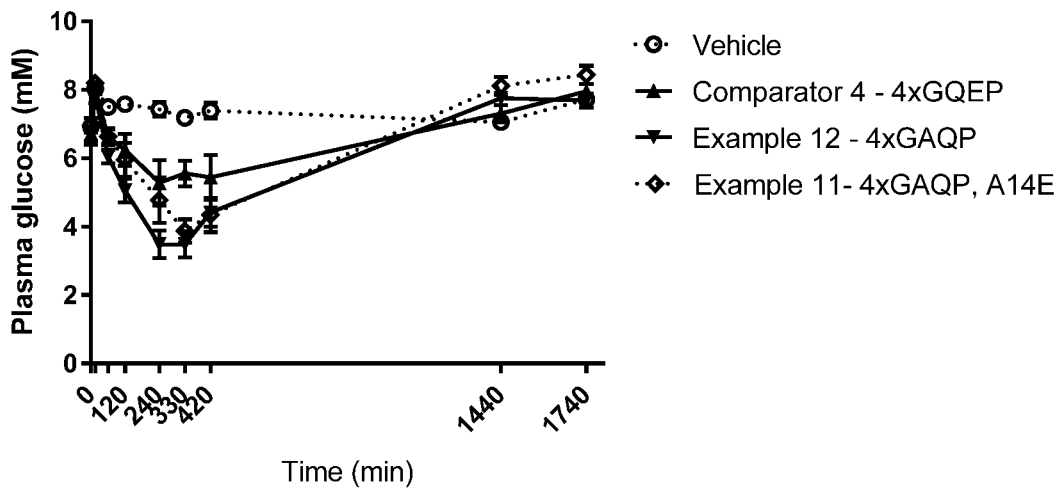
FIG. 6 shows the blood glucose lowering effects of the compounds of examples 11 and 12 of the invention with 4×GAQP spacer, relative to the blood glucose lowering effect of the comparator compound 4 with 4×GQEP spacers, all with the octadecanedioyl-gGlu-2×OEG side chain.

From observing FIG. 6, it is concluded that for the spacer 4×GAQP, the insulin substitutions desB30 and A14E, desB30 are conferring equal insulin potency, whereas the spacer 4×GQEP surprisingly compromises insulin potency.

Figure 7:
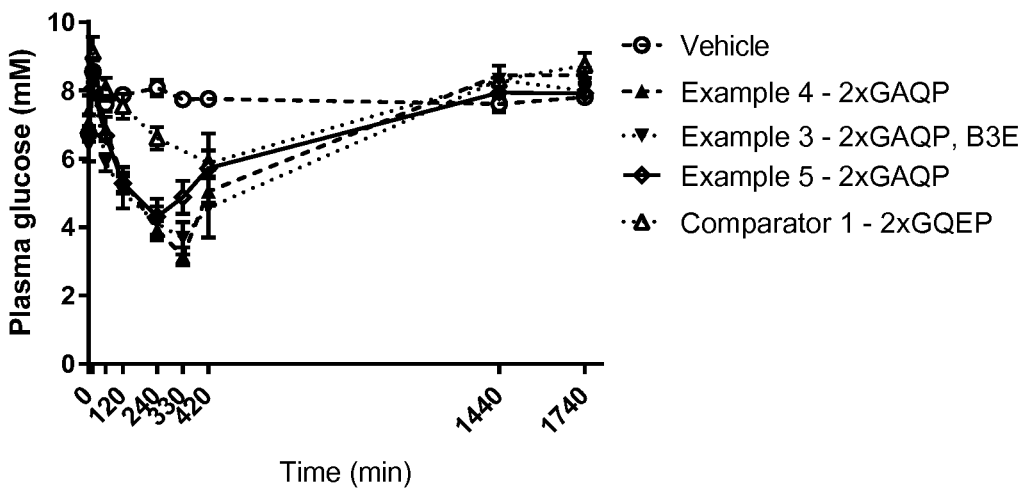
FIG. 7 shows the blood glucose lowering effects of the compounds of examples 3, 4, and 5 of the invention, with 2×GAQP spacer, relative to the blood glucose lowering effect of the comparator compound 1 with 2×GQEP spacer, all compounds with the octadecanedioyl-gGlu-2×OEG side chain.

From observing FIG. 7, it is concluded that the insulin substitutions desB30 and B3E, desB30 are conferring equal insulin potency, and that the side chains containing one and two OEG moieties are conferring equal insulin potency whereas the spacer 2×GQEP surprisingly compromises insulin potency as compared with the similar compounds with the spacer 2×GAQP.

Figure 8:
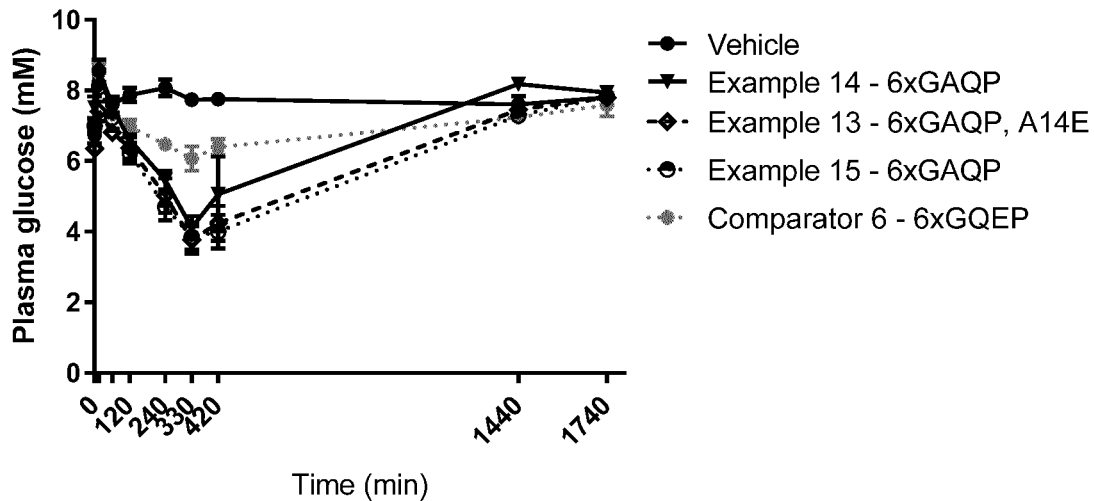
FIG. 8 shows the blood glucose lowering effects of the compounds of examples 13, 14, and 15 of the invention, with 6×GAQP spacer, relative to the blood glucose lowering effect of the comparator compound 6 with 6×GQEP spacer, all with C18 side chain.

From observing FIG. 8, it is concluded that the insulin substitutions desB30 and A14E, desB30 are conferring equal insulin potency, and that the side chains containing one and two OEG moieties are conferring equal insulin potency whereas the spacer 6×GQEP surprisingly compromises insulin potency as compared with the similar compound with the spacer 6×GAQP.

Figure 9:
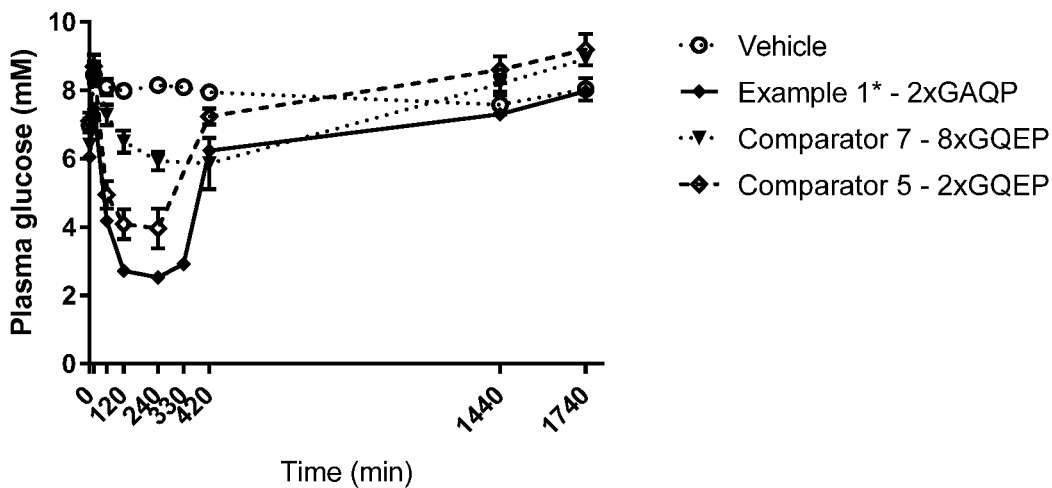
FIG. 9 shows the blood glucose lowering effects of the compound of example 1 of the invention, and with 2×GAQP spacer, relative to the blood glucose lowering effect of the comparator compounds 5 and 7 with 2× or 8×GQEP spacer, all with hexadecanedioyl-gGlu-2×OEG side chain.

From observing FIG. 9, it is concluded that insulins with sidechains hexadecanedioyl-gGlu-2×OEG, the spacer 2×GAQP of example 1 is surprisingly conferring much higher insulin potency than the spacers 2×GQEP and 8×GQEP.

Figure 10:
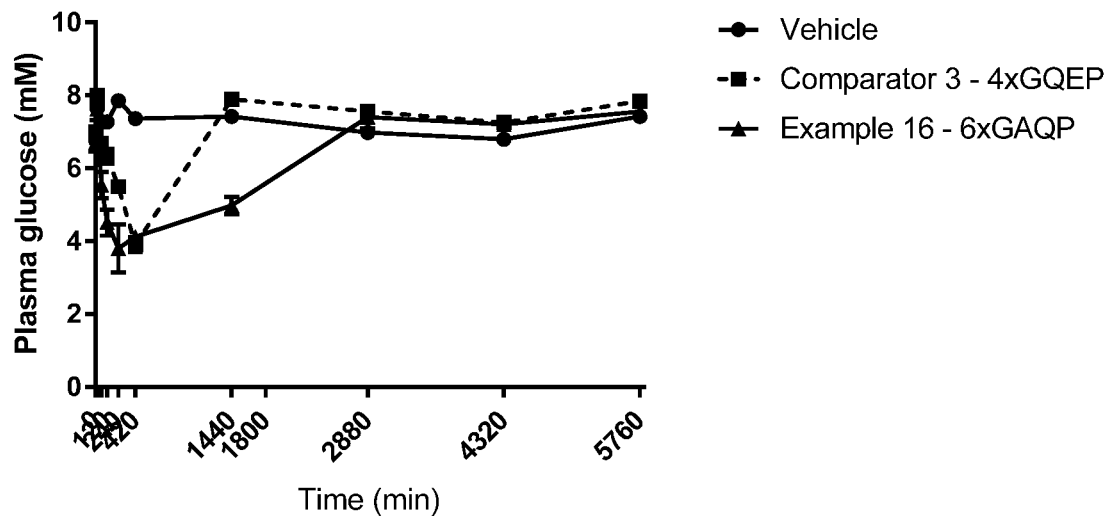
FIG. 10 shows the blood glucose lowering effects of the compound of example 16 of the invention, and with 6×GAQP spacer, relative to the blood glucose lowering effect of the comparator compound 3 with 6×GQEP spacer, both with eicosanedioyl-gGlu-2×OEG side chain.

From observing FIG. 10 it is concluded that insulins with sidechains eicosanedioyl-gGlu-2×OEG, the spacer 6×GAQP is surprisingly conferring much higher insulin potency than the spacer 4×GQEP.

Figure 11:
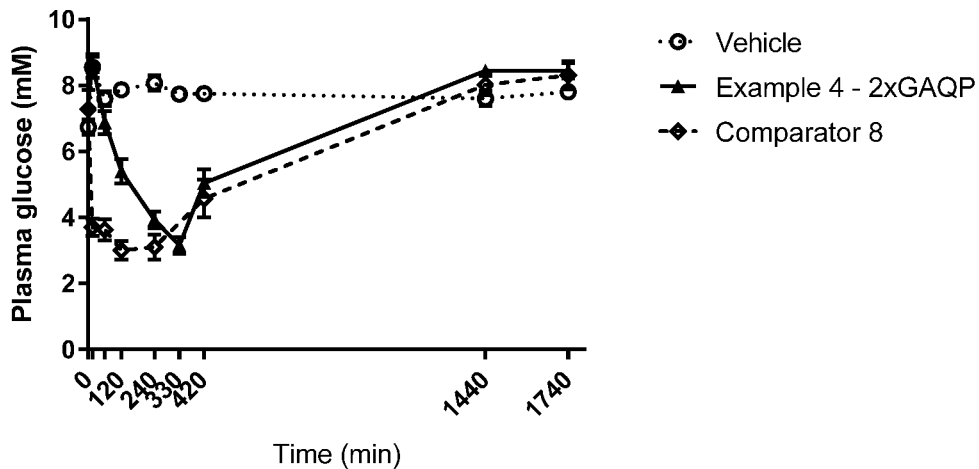
FIG. 11 shows the blood glucose lowering effects of the compound of example 4 of the invention with 2×GAQP, relative to the blood glucose lowering effect of the "insulin alone" comparator compound 8, both with octadecanedioyl-gGlu-2×OEG side chain.

From observing FIG. 11, it is concluded that appending an EGF(A) moiety of the invention via a non-charged linker to an insulin results in a compound with similar glucodynamic potency as compared to the potency of the insulin alone. The fusion protein of the invention has a slower onset of action which is advantageous for a basal insulin.

Example 31

Acute In Vivo Proof of Concept Model: Human PCSK9 (hPCSK9) Challenge Model in Streptozotocin Induced Diabetic Mice The aim of the model is to demonstrate dual-activity of an insulin-EGF(A) fusion protein. Dual-activity meaning an increase in the LDL receptor expression level in mouse liver by inhibiting the action of intravenously injected hPCSK9 with an insulin-EGF(A) based anti-PCSK9 peptide and glucose lowering effect by the insulin part of the molecule.

Method: Healthy male BalBC mice (Charles River, Germany) were rendered diabetic by a single high subcutaneous (s.c.) dose of streptozotocin (230-250 mg/kg). After 5-7 days, diabetic animals were randomized into designated treatment groups. On the day of experimentation animals were intravenously (i.v.) injected at t=0 min ($1^{st}$ dosing on graphs) with vehicle, EGF(A) derivative or insulin-EGF(A) fusion protein. At t=15 min hPCSK9 or vehicle was injected i.v. at a dose of 0.4 mg/kg ($2^{nd}$ dosing on graphs). Blood glucose levels were measured at time=0, 15, 45 and 75 min. Sixty minutes after the injection of hPCSK9 (t=75 min), the animals were anaesthetised in isoflurane and euthanized by cervical dislocation. The liver was quickly excised and frozen in liquid nitrogen. The liver samples were kept at −80 degrees Celsius until analysis. LDL-r protein in the liver samples was quantified by ELISA.

Mouse LDL-R ELISA: A piece of liver (10 mg) was homogenised in 500 uL PBS on a TissueLyser 2.5 min at 30 Hz using a steel bead. Then, the tissue was lysed by adding 500 uL of 2× Lysis Buffer 2 (R&D systems cat no. 895347) and incubated on a shaker (500 rpm) for 1 h. The liver lysate was centrifuged 10 minutes at 20000 g 4° C. Clear supernatant was diluted 50× in calibrator diluent and 50 uL was used for analysis on the mLDL-R ELISA (RD Systems MLDLR0). The value of LDL-R concentration in the liver lysate was normalised with protein concentration in the same sample. The lysate was diluted 20× in PBS and 25 uL was used for protein determination in 2 replicates according to the Pierce BCA Protein Assay Kit (cat.no. 23225).

In vivo dual-activity was demonstrated for the insulin-EGF(A) fusion protein by investigating blood glucose changes and liver LDL-r protein expression following dosing of compounds to streptozotocin-diabetic mice. The insulin-EGF(A) fusion protein of example 3 was dosed at 0, 3, 10, 30 and 100 nmol/kg, n=5-6 animals per group. FIG. 12 shows that hPCSK9 administered to mice resulted in an almost complete down regulation of the hepatic LDL receptor protein. The insulin-EGF(A)fusion protein effectively prevented this PCSK9-mediated down regulation of the LDLr protein in a dose-dependent way. Additionally, the insulin-EGF(A)fusion protein lowered blood glucose dose-dependently (FIG. 13). Furthermore, it was shown that two insulin-EGF(A)fusion proteins were able to prevent the hPCSK9-mediated down regulation of LDLr protein similar to what was seen with the EGF(A) derivative alone (FIG. 14).

The invention claimed is:

1. A fusion protein comprising:
an insulin peptide, an Epidermal Growth Factor-like domain (A) (EGF(A)) peptide, a spacer and a substituent, wherein:
(i) said insulin peptide is human insulin (SEQ ID NOs 2 and 3) or an analogue of human insulin,
(ii) said EGF(A) peptide is an analogue of the EGF(A) domain of LDL-R (293-332) according to SEQ ID NO:1,
(iii) said spacer is a peptide linker comprising segments of (GAQP)n or (GQAP)n, wherein n=1-20, and connecting the N-terminal of the insulin analogue B-chain with the C-terminal of the EGF(A) analogue, and
(iv) said substituent is of formula (I): Acy-AA2$_m$-AA3$_p$-, wherein
Acy is a fatty diacid comprising from about 16 to about 20 carbon atoms,
AA2 is an acidic amino acid residue and m is an integer in the range from 1 to 10, and
AA3 is a neutral, alkyleneglycol-containing amino acid residue and p is an integer in the range from 1 to 10, and
wherein the maximum number of AA2 and AA3 residues is 10, and
wherein the AA2 and AA3 residues may appear in any order,
or a pharmaceutically acceptable salt, amide, or ester thereof.

2. The fusion protein according to claim 1, wherein said EGF(A) analogue comprises the mutation 301L.

3. The fusion protein according to claim 2, wherein said EGF(A) analogue further comprises a mutation selected from 309R, [309R, 312E] or [309R, 312E, 321E].

4. The fusion protein according to claim 1, wherein said EGF(A) analogue sequence comprises a mutation selected from 301L, 309R, 312E and 321E.

5. The fusion protein according to claim 1, wherein the insulin peptide is human insulin or an analogue/derivative of human insulin comprising up to 12 mutations.

6. The fusion protein according to claim 1, wherein said insulin analogue comprises the mutation desB30.

7. The fusion protein according to claim 1, wherein said spacer comprises (GAQP)n, wherein n is 2-10.

8. The fusion protein according to claim 1, wherein said substituent is attached via a Lys/K amino acid residue in the insulin sequence within said fusion protein.

9. The fusion protein according to claim 8, wherein said substituent is attached via a Lys/K amino acid residue B29K in the insulin sequence of said fusion protein.

10. The fusion protein according to claim 1, wherein at least one acyl moiety comprises a fatty diacid group selected from 1,16-hexadecanedioic acid, 1,18-octadecanedioic acid and 1,20-eicosanedioic acid.

11. The fusion protein according to claim 1, wherein said fusion protein is selected from the group consisting of compounds 1-24:
 (i) EGF(A)(301L, 309R, 312E, 321 E)-[GAQP]2-Insulin (B3E, B29K(hexadecanedioyl-gGlu-2×OEG), desB30) (Chem. 1),
 (ii) EGF(A)(301L, 309R, 312E, 321E)-[GAQP]10-Insulin(B29K(octadecanedioyl-gGlu-2×OEG), desB30) (Chem.2),
 (iii) EGF(A)(301L, 309R, 312E, 321 E)-[GAQP]2-Insulin(B3E, B29K(octadecanedioyl-gGlu-2×OEG), desB30) (Chem.3),
 (iv) EGF(A)(301L, 309R, 312E, 321 E)-[GAQP]2-Insulin (B29K(octadecanedioyl-gGlu-2×OEG), desB30) (Chem.4),
 (v) EGF(A)(301L, 309R, 312E, 321 E)-[GAQP]2-Insulin (B3E, B29K(octadecanedioyl-gGlu-OEG), desB30) (Chem.5),
 (vi) EGF(A)(301L, 309R, 312E, 32 1E)-[GAQP]2-Insulin (B3E, B29K(eicosanedioyl-gGlu-2×EG), desB30) (Chem.6),
 (vii) EGF(A)(301L, 309R, 312E, 321 E)-[GAQP]2-Insulin(B29K(eicosanedioyl-gGlu-2×OEG), desB30) (Chem.7),
 (viii) EGF(A)(301L, 309R, 312E, 321 E)-[GQAP]2-Insulin(B29K(octadecanedioyl-gGlu-2×OEG), desB30) (Chem.8),
 (ix) EGF(A)(301L, 309R, 312E, 321 E)-[GAQP]3-Insulin (B29K(octadecanedioyl-gGlu-2×OEG), desB30) (Chem.9),
 (x) EGF(A)(301L, 309R, 312E, 321E)-[GAQP]3-Insulin (A14E, B29K(octadecanedioyl-gGlu-2×OEG), desB30) (Chem. 10),
 (xi) EGF(A)(301L, 309R, 312E, 321E)-[GAQP]4-Insulin (A14E, B29K(octadecanedioyl-gGlu-2×OEG), desB30) (Chem. 11),
 (xii) EGF(A)(301L, 309R, 3 12E, 321 E)-[GAQP]4-Insulin(B29K(octadecanedioyl-gGlu-2×OEG), desB30) (Chem. 12),
 (xiii) EGF(A)(301L, 309R, 312E, 321 E)-[GAQP]6-Insulin(A14E, B29K(octadecanedioyl-gGlu-2×OEG), desB30) (Chem. 13),
 (xiv) EGF(A)(301L, 309R, 312E, 321 E)-[GAQP]6-Insulin(B29K(octadecanedioyl-gGlu-2×OEG), desB30) (Chem. 14),
 (xv) EGF(A)(301L, 309R, 312E, 321 E)-[GAQP]6-Insulin(A14E, B29K(octadecanedioyl-gGlu-OEG), desB30) (Chem. 15),
 (xvi) EGF(A)(301L, 309R, 3 12E, 321E)-[GAQP]6-Insulin(A14E, B29K(eicosanedioyl-gGlu-2×OEG), desB30 (Chem.16),
 (xvii) EGF(A)(301L, 309R, 312E, 321 E)-[GAQP]8-Insulin(B29K(octadecanedioyl-gGlu-2×OEG), desB30) (Chem. 17),
 (xviii) EGF(A)(301L, 309R, 3 12E, 321 E)-[GAQP]12-Insulin(B29K(octadecanedioyl-gGlu-2×OEG), desB30) (Chem. 18),
 (xix) EGF(A)(301L, 309R, 3 12E, 321 E)-[GAQP]19-Insulin(B29K(octadecanedioyl-gGlu-2×OEG), desB30) (Chem. 19),
 (xx) EGF(A)(301L, 309R, 3 12E, 321 E)-[GAQP]19-Insulin(A14E, B29K(octadecanedioyl-gGlu-2×OEG), desB30) (Chem.20),
 (xxi) EGF(A)(301L, 309R, 3 12E, 321E)-[GAQP]19-Insulin(B3E, B29K(octadecanedioyl-gGlu-2×OEG), desB30) (Chem.21),
 (xxii) EGF(A)(301L, 309R, 3 12E, 321 E)-[GAQP]19-Insulin(B29K(eicosanedioyl-gGlu-2×OEG), desB30) (Chem.22),
 (xxiii) EGF(A)(301L, 309R, 312E, 321 E)-[GAQP]19-Insulin(A14E, B29K(eicosanedioyl-gGlu-2×OEG), desB30) (Chem.23), and
 (xxiv) EGF(A)(301L, 309R, 312E, 321 E)-[GAQP]19-Insulin(B3E, B29K(eicosanedioyl-gGlu-2×OEG), desB30) (Chem.24).

12. A pharmaceutical composition, comprising a therapeutically effective amount of a fusion protein according to claim 1, together with a pharmaceutically acceptable excipient.

13. A method of treatment of a disease comprising administering to a subject in need thereof of a pharmaceutically effective amount of the composition of claim 12, wherein the disease is selected from the group consisting of Type 1 diabetes, Type 2 diabetes, impaired glucose tolerance, hyperglycemia or diabetic dyslipidemia.

14. The method according to claim 13, wherein the subject is in need of treatment of a disease selected from the group consisting of Type 1 diabetes, Type 2 diabetes or diabetic dyslipidemia.

* * * * *

UNITED STATES PATENT AND TRADEMARK OFFICE
CERTIFICATE OF CORRECTION

| | | |
|---|---|---|
| PATENT NO. | : 11,649,269 B2 | Page 1 of 1 |
| APPLICATION NO. | : 17/281813 | |
| DATED | : May 16, 2023 | |
| INVENTOR(S) | : Martin Werner Borchsenius Muenzel et al. | |

It is certified that error appears in the above-identified patent and that said Letters Patent is hereby corrected as shown below:

In the Claims

At Column 107, Claim number 11, Line number 45, Please replace "(eicosanedioul-gGlu-2xEG)" with "(eicosanedioul-gGlu-2xOEG)"

At Column 108, Claim number 11, Line number 4, Please replace "3 12E, 321 E" with "312E, 321E"

At Column 108, Claim number 11, Line number 23, Please replace "3 12E, 321 E" with "312E, 321E"

At Column 108, Claim number 11, Line number 26, Please replace "3 12E, 321 E" with "312E, 321E"

At Column 108, Claim number 11, Line number 29, Please replace "3 12E, 321 E" with "312E, 321E"

At Column 108, Claim number 11, Line number 32, Please replace "3 12E, 321 E" with "312E, 321E"

At Column 108, Claim number 11, Line number 34, Please replace "3 12E, 321 E" with "312E, 321E"

Signed and Sealed this
First Day of October, 2024

Katherine Kelly Vidal
*Director of the United States Patent and Trademark Office*